(12) United States Patent
Matsuoka et al.

(10) Patent No.: US 7,741,346 B2
(45) Date of Patent: Jun. 22, 2010

(54) ANGIOGENESIS INHIBITOR

(75) Inventors: Hidehito Matsuoka, Ikoma (JP); Kazuo Nishimura, Osaka (JP); Hisayuki Seike, Ikoma (JP); Hiroyuki Aono, Osaka (JP); Masaaki Murai, Osaka (JP)

(73) Assignee: Santen Pharmaceutical Co., Ltd., Osaka-shi, Osaka (JP)

( * ) Notice: Subject to any disclaimer, the term of this patent is extended or adjusted under 35 U.S.C. 154(b) by 1442 days.

(21) Appl. No.: 10/497,223

(22) PCT Filed: Nov. 29, 2002

(86) PCT No.: PCT/JP02/12481
§ 371 (c)(1),
(2), (4) Date: May 28, 2004

(87) PCT Pub. No.: WO03/045367
PCT Pub. Date: Jun. 5, 2003

(65) Prior Publication Data
US 2005/0014800 A1   Jan. 20, 2005

(30) Foreign Application Priority Data
Nov. 30, 2001   (JP) ............................. 2001-366088

(51) Int. Cl.
*A61K 31/44* (2006.01)
*C07D 213/0025* (2006.01)
(52) U.S. Cl. ...................... 514/357; 546/322
(58) Field of Classification Search ................ 546/332, 546/322; 514/357
See application file for complete search history.

(56) References Cited

U.S. PATENT DOCUMENTS

| 6,420,398 B2 * | 7/2002 | Mita et al. .................. 514/357 |
| 7,345,064 B2 * | 3/2008 | Ban et al. ................... 514/357 |
| 7,491,739 B2 * | 2/2009 | Ban et al. ................... 514/357 |
| 2001/0041725 A1 | 11/2001 | Mita | |
| 2001/0041744 A1 | 11/2001 | Mita | |
| 2008/0161270 A1 * | 7/2008 | Matsuoka et al. ............. 514/63 |

FOREIGN PATENT DOCUMENTS

| EP | 1 103 543 A1 | 5/2001 |
| EP | 02/28831 A1 | 10/2001 |
| JP | 2002-255800 A | 9/2002 |
| JP | 2002-284685 A | 10/2002 |
| WO | WO 0007985 | * 2/2000 |
| WO | WO 0039083 | * 6/2000 |
| WO | WO 00/39083 A1 | 7/2000 |
| WO | WO 01/49288 A1 | 7/2001 |
| WO | WO 01/53262 A1 | 7/2001 |
| WO | WO 01/09222 A1 | 12/2001 |
| WO | WO 02/28831 A1 | 4/2002 |

OTHER PUBLICATIONS

Rak et. al., "Treating cancer by inhibiting angiogenesis: new hopes and potential pitfalls", Cancer and Metastasis Reviews, 15: 231-236, 1996.*
Hcaplus 114:101812.*
Hcaplus 133:144061.*
Hcaplus 1996:95038, "Synthesis and Antihyerptensive Activeity of -N-(alkyl/alkeny/aryl)-N'-heterocyclic Ureas and Thioreas", Vajragupta et. al., 1996.*
Hcaplus 1978:169696, "Reactions with aziridines, XV. Amidoethylation of triarylmethanes and diarylamines with 1-acylaziridines", Stamm et. al., 1978.*
Caplus Abstract 2000:117023, (Feb. 17, 2000).*
Murao et. al., "Histological Changes of the Pancreas in an Elderly Diabetic Patient Positive for GAD Antibody", Internal Medicine, Nol. 39, No. 12, (Dec. 2000).*
*Journal of Clinical and Experimental Medicine*, 170, 536-539 (1994) and a partial English language translation thereof.
Satoshi Murao et al., "Histological Changes of the Pancreas in an Elderly Diabetic Patient Positive for GAD Antibody," vol. 39, No. 12 (Dec. 2000), 1079-1082.

* cited by examiner

*Primary Examiner*—Janet L Andres
*Assistant Examiner*—Binta M Robinson
(74) *Attorney, Agent, or Firm*—Frishauf, Holtz, Goodman & Chick, P.C.

(57) ABSTRACT

An object of the present invention is to find new pharmacological actions of urea compounds having structure represented by the general formula [1]. The urea compounds having the structure represented by the general formula [1] have excellent angiogenesis inhibitory actions.

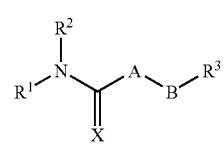

[1]

[wherein "A" is —(NR⁴)—, —(CR⁵R⁶)— or —O—, "B" is alkylene or alkenylene, $R^1$, $R^2$, $R^4$, $R^5$ and $R^6$ are hydrogen, alkyl, alkenyl, adamantylalkyl or the like, $R^3$ is aryl or an unsaturated heterocycle, and X is oxygen or sulfur].

2 Claims, No Drawings

ANGIOGENESIS INHIBITOR

This application is the United States national phase application of International Application PCT/JP02/12481 filed Nov. 29, 2002.

TECHNICAL FIELD

The present invention relates to angiogenesis inhibitors comprising novel urea compounds as active ingredients, particularly drugs which are useful for ophthalmopathy and cancer.

BACKGROUND ART

Homeostasis of blood vessels is maintained by various functions of endothelial cells. The vascular endothelial cells have 1) an effect of mediating transportation of necessary components such as nutrition in blood to tissues and preventing unnecessarily much components from passing, 2) an effect of circulating blood smoothly without coagulation, 3) an effect of stopping hemorrhage when the blood vessels are transected, and 4) a regulatory effect of keeping vasotonia constant.

Angiogenesis occurs stepwise as follows; decomposition of a basement membrane by protease produced by the vascular endothelial cells, migration and proliferation of the vascular endothelial cells, tube formation of the vascular endothelial cells, formation of the basement membrane and encirclement of peripheral cells. The angiogenesis is closely related to various diseases, particularly diabetic retinopathy, retinopathy of prematurity, macular degeneration, neovascular glaucoma, retinal vein occlusion, retinal artery occlusion, pterygium, rubeosis, corneal neovasculature, solid tumors, hemangioma, proliferation and transfer of tumors and the like. Angiogenesis is caused by various proliferation factors, cytokine, arachidonic acid metabolites, monobutyrin and the like. The proliferation factors are considered to be the most important angiogenesis factors among them (Journal of Clinical and Experimental Medicine, 170, 536-539 (1994)).

Thus, it is meaningful to search compounds having angiogenesis inhibitory actions which are useful as therapeutic agents for diabetic retinopathy, retinopathy of prematurity, macular degeneration, neovascular glaucoma, retinal vein occlusion, retinal artery occlusion, pterygium, rubeosis, corneal neovasculature, solid tumors, hemangioma, proliferation and transfer of tumors and the like.

DISCLOSURE OF THE INVENTION

Preparing compounds having various chemical structures and carrying out angiogenesis inhibition tests using human endothelium cells and angiogenesis inhibition tests by an oxygen-induced retinal angiogenesis model, the present inventors found that novel urea compounds having a structure represented by the following general formula [1] exhibit excellent angiogenesis inhibitory actions in both in vitro and in vivo tests and are useful as therapeutic agents for diseases in which angiogenesis participates, particularly ophthalmopathy such as diabetic retinopathy, retinopathy of prematurity, macular degeneration, neovascular glaucoma, retinal vein occlusion, retinal artery occlusion, pterygium, rebeosis or corneal neovasculature and cancer such as solid tumors, hemangioma or proliferation and transfer of tumors to complete the present invention.

The present invention relates to angiogenesis inhibitors comprising compounds represented by the following general formula [1] or salts thereof (hereinafter referred to as "the present compound" as far as there is no proviso) as active ingredients.

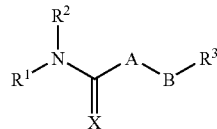

[1]

[wherein "A" is —(NR$^4$)—, —(CR$^5$R$^6$)— or —O—;
"B" is alkylene or alkenylene which can contain —O—, —S—, (NR$^7$)—, —CO—, —N= or the following group in its chain,

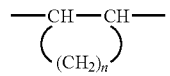

wherein the alkylene and alkenylene can be substituted by hydroxyl, alkoxy, cycloalkyl, aryl, siloxy or a saturated or unsaturated heterocycle and can be bonded to "A" to form a saturated heterocycle;
R$^1$, R$^2$, R$^4$, R$^5$ and R$^6$, the same or different, are hydrogen, alkyl, alkenyl, alkynyl, cycloalkyl, cycloalkenyl, hydroxyl, acyl or amino, wherein the alkyl, alkenyl, alkynyl, cycloalkyl or cycloalkenyl can be substituted by halogen, hydroxyl, amino, cycloalkyl, adamantyl, aryl, carboxyl, alkoxycarbonyl, aryloxycarbonyl, aminocarbonyl, cyano or a saturated or unsaturated heterocycle;
R$^1$ and R$^2$, R$^2$ and R$^4$, R$^2$ and R$^5$, and R$^2$ and R$^6$ each can form a saturated or unsaturated heterocycle;
R$^3$ is aryl or an unsaturated heterocycle;
R$^7$ is hydrogen or alkyl;
X is =O or =S;
n is an integer of 1 to 5.

Hydrogen in each amino, hydroxyl and aminocarbonyl can be substituted by alkyl, cycloalkyl, adamantyl, adamantylalkyl, aryl, arylalkyl, acyl, alkoxyalkyl, alkoxycarbonyl, alkylaminocarbonyl, cycloalkyloxycarbonyl, arylalkoxycarbonyl, alkylsulfonyl, arylsulfonyl, halogenoalkyloxycarbonyl, imidazolylcarbonyl, pyridylcarbonyl, a saturated or unsaturated heterocycle, or alkyl substituted by a saturated or unsaturated heterocycle. The same definitions are applied hereinafter.]

Since the present compounds exhibit excellent angiogenesis inhibitory actions, the present compounds act as active ingredients of therapeutic agents for diseases accompanied by angiogenesis such as diabetic retinopathy, retinopathy of prematurity, macular degeneration, neovascular glaucoma, retinal vein occlusion, retinal artery occlusion, pterygium, rebeosis, corneal neovasculature, solid tumors, hemangioma, and proliferation and transfer of tumors.

The respective groups defined by the general formula [1] are described in detail.

The alkylene is straight-chain or branched alkylene having one to 12 carbon atoms such as methylene, ethylene, trimethylene, propylene, tetramethylene, pentamethylene, hexamethylene, octamethylene, decamethylene, dodecamethylene, methylmethylene, ethylethylene, dimethylethylene, propylethylene, isopropylethylene or methyltrimethylene.

The alkenylene is straight-chain or branched alkenylene having one or more double bond and two to 12 carbon atoms such as vinylene, propenylene, butenylene, pentenylene, hexenylene, octenylene, butanediylidene or methylpropenylene.

The alkyl is straight-chain or branched alkyl having one to 12 carbon atoms such as methyl, ethyl, propyl, butyl, hexyl, octyl, decyl, dodecyl, isopropyl, isobutyl, isopentyl, isohexyl, isooctyl, t-butyl or 3,3-dimethylbutyl.

The alkoxy is straight-chain or branched alkoxy having one to 12 carbon atoms such as methoxy, ethoxy, propoxy, butoxy, hexyloxy, octyloxy, decyloxy, dodecyloxy, isopropoxy or t-butoxy.

The alkenyl is straight-chain or branched alkenyl having two to 12 carbon atoms such as vinyl, allyl, 3-butenyl, 5-hexenyl or isopropenyl.

The alkynyl is straight-chain or branched alkynyl having two to 12 carbon atoms such as ethynyl, propynyl or butynyl.

The cycloalkyl is cycloalkyl having three to 20 carbon atoms such as cyclopropyl, cyclobutyl, cyclopentyl, cyclohexyl, cycloheptyl, cyclooctyl, cyclodecyl or cyclododecyl.

The cycloalkenyl is cycloalkenyl having five to 20 carbon atoms such as cyclopentenyl, cyclohexenyl or cycloheptenyl.

The aryl is an aromatic hydrocarbon ring such as phenyl or naphthyl and can have one or more substituent. Examples of the substituents are alkyl, cycloalkyl, carboxyl, amino, hydroxyl, aminoalkyl, hydroxyalkyl, nitro, cyano, halogen and alkyloxy.

The siloxy is an organic silicon-containing group such as trialkylsilyloxy, dialkyl(aryl)silyloxy, alkyl(diaryl)oxy or triarylsilyloxy.

The halogen is fluorine, chlorine, bromine or iodine.

The heterocycle is, for example, a five to 20-membered saturated or unsaturated monocyclic or bicyclic heterocycle having one to four nitrogen atom(s), oxygen atom(s) and/or sulfur atom(s) and can have one or more substituent. Examples of the substituents are alkyl, cycloalkyl, carboxyl, amino, hydroxyl, aminoalkyl, hydroxyalkyl, nitro, cyano, halogen, alkyloxy, aryl, arylalkyl and saturated or unsaturated heterocycles. When the heterocycles have nitrogen atom(s) or sulfur atom(s) in their ring, these atoms can be oxidized to be in the form of N-oxide, S-oxide or the like.

Specific examples of saturated heterocycles are monocyclic heterocycles such as pyrrolidine, piperidine, homopiperidine and piperazine having nitrogen atom(s) in their ring, morpholine having a nitrogen atom and an oxygen atom in its ring, and thiomorpholine having a nitrogen atom and a sulfur atom in its ring, and they can be condensed with a benzene ring and the like to form bicyclic heterocycles such as tetrahydroquinoline and tetrahydroisoquinoline.

Specific examples of unsaturated heterocycles are monocyclic heterocycles such as pyrrol, pyridine, pyrazole, imidazole, pyrazine, pyridazine and pyrimidine or bicyclic heterocycles such as indole, quinoline, isoquinoline, benzimidazole, naphthylidine, pyrropyridine and imidazopyridine having nitrogen atom(s) in their ring, monocyclic heterocycles such as furan or bicyclic heterocycles such as benzofuran having an oxygen atom in their ring, monocyclic heterocycles such as thiophene or bicyclic heterocycles such as benzothiophene having a sulfur atom in their ring, and monocyclic heterocycles such as oxazole, isoxazole, thiazole and isothiazole or bicyclic heterocycles such as benzoxazole, benzothiazole, thienopyridine, oxazolopyridine, thiazolopyridine and furopyridine having a nitrogen atom and an oxygen atom or a sulfur atom in their ring. Further, the above-mentioned unsaturated heterocycles can be in the form of containing saturated bond(s) partly.

The salts in the present invention can be any pharmaceutically acceptable salts and are exemplified by salts with an inorganic acid such as hydrochloric acid, nitric acid, sulfuric acid or phosphoric acid, salts with an organic acid such as acetic acid, fumaric acid, maleic acid, succinic acid or tartaric acid, salts with an alkali metal or an alkaline earth metal such as sodium, potassium or calcium, and the like. Quaternery ammonium salts of the present compounds are also included in the salts in the present invention. Further, when there are geometric isomers or optical isomers in the present compounds, these isomers are also included in the present invention. The present compounds can be in the form of hydrates and solvates.

Preferred examples of the present invention are the following compounds (1) to (3).

(1) Compounds or salts thereof wherein the group(s) defined in the general formula [1] are specified by selecting one from the followings, i.e. 1) to 4), and combinations thereof,
1) $R^3$ is a pyridine ring,
2) at least one of $R^1$, $R^2$, $R^4$, $R^5$ and $R^6$ is adamantylalkyl, adamantyloxyalkyl, adamantylaminoalkyl or adamantylaminocarbonylalkyl,
3) at least one of $R^1$ and $R^2$ is adamantylalkyl, adamantyloxyalkyl, adamantylaminoalkyl or adamantylaminocarbonylalkyl, and
4) at least one of $R^1$ and $R^2$ is adamantylalkyl.

(2) Compounds or salts thereof wherein the respective groups defined in the general formula [1] are the following groups,
"A" is —(NR$^4$)—, —(CR$^5$R$^6$)— or —O—,
"B" is alkylene or alkenylene which can contain in its chain —O—, —S—, —(NR$^7$)—, —CO—, —N= or the following group,

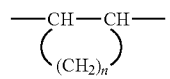

wherein the alkylene can be substituted by hydroxyl, alkoxy, aryl, siloxy or a saturated or unsaturated heterocycle and can be bonded to "A" to form a saturated heterocycle,
$R^1$ is hydrogen, alkyl, alkenyl, alkynyl, cycloalkyl, cycloalkenyl, hydroxyl or amino, wherein the alkyl, alkenyl, alkynyl, cycloalkyl or cycloalkenyl can be substituted by halogen, hydroxyl, amino, cycloalkyl, aryl, carboxyl, alkoxycarbonyl, alkylaminocarbonyl, adamantyl, aryloxycarbonyl, cyano or a saturated or unsaturated heterocycle, and hydrogen in each amino, hydroxyl and aminocarbonyl in $R^1$ can be substituted by alkyl, cycloalkyl, aryl, arylalkyl, acyl, alkoxycarbonyl, cycloalkyloxycarbonyl, arylalkoxycarbonyl, halogenoalkyloxycarbonyl, imidazolylcarbonyl, an unsaturated heterocycle or alkyl substituted by an unsaturated heterocycle,
$R^2$ is adamantylalkyl, adamantyloxyalkyl, adamantylaminoalkyl or adamantylaminocarbonylalkyl,
$R^3$ is an unsaturated heterocycle,
$R^4$ is hydrogen, alkyl, adamantylalkyl, carboxyalkyl, alkoxycarbonyl, alkoxycarbonylalkyl, amino, alkylamino, acylamino or alkoxycarbonylamino,
$R^5$ and $R^6$, the same or different, are hydrogen, alkyl, amino or alkoxycarbonylamino,
$R^7$ is hydrogen or alkyl,
X is =O or =S, and
n is an integer of 1 to 5.

Compounds wherein $R^2$ is adamantylalkyl, and $R^3$ is a pyridine ring are more preferable among them.

Further, compounds or salts thereof wherein the respective groups defined in the general formula [1] are the following groups are particularly preferable.

"A" is —(NR$^4$)—, —(CR$^5$R$^6$)— or —O—,
"B" is alkylene or alkenylene which can contain in its chain —S— or the following group,

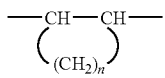

R$^1$ is alkyl or alkenyl, wherein the alkyl can be substituted by halogen or amino, and further the amino can be substituted by alkyl, acyl, arylalkyloxycarbonyl, cycloalkyloxycarbonyl or alkoxycarbonyl,
R$^2$ is adamantylalkyl,
R$^3$ is a pyridine ring,
R$^4$ is hydrogen,
R$^5$ and R$^6$ are hydrogen,
X is =O, and
n is an integer of 1 to 5.

(3) Compounds or salts thereof wherein the respective groups defined in the general formula [1] are the following groups,
"A" is —(NR$^4$)—, —(CR$^5$R$^6$)— or —O—,
"B" is alkylene or alkenylene which can contain in its chain —O—, —S—, —(NR$^7$)—, —N= or the following group,

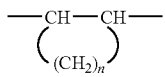

wherein the alkylene can be substituted by hydroxyl, alkoxy, aryl or a saturated or unsaturated heterocycle and can be bonded to "A" to form a saturated heterocycle,
R$^1$ is hydrogen, alkyl, alkenyl, alkynyl, cycloalkyl, cycloalkenyl, hydroxyl or amino, wherein the alkyl, alkenyl, alkynyl, cycloalkyl or cycloalkenyl can be substituted by halogen, hydroxyl, amino, cycloalkyl, aryl, carboxyl, alkoxycarbonyl, aryloxycarbonyl, aminocarbonyl, cyano or a saturated or unsaturated heterocycle, and hydrogen in each amino, hydroxyl and aminocarbonyl in R$^1$ can be substituted by alkyl, cycloalkyl, aryl, arylalkyl, acyl, alkoxycarbonyl, cycloalkyloxycarbonyl, arylalkoxycarbonyl, an unsaturated heterocycle or alkyl substituted by an unsaturated heterocycle,
R$^2$ is alkyl, alkenyl, cycloalkyl, cycloalkylalkyl or arylalkyl,
R$^3$ is a pyridine ring,
R$^4$ is hydrogen, alkyl, adamantylalkyl, carboxyalkyl, alkoxycarbonylalkyl, amino, alkylamino, acylamino or alkoxycarbonylamino,
R$^5$ and R$^6$, the same or different, are hydrogen or alkyl,
R$^7$ is hydrogen or alkyl,
X is =O or =S, and
n is an integer of 1 to 5.

Compounds and salts thereof wherein the respective groups defined in the general formula [1] are the following groups are more preferable among them.
"A" is —(NR$^4$)— or —(CR$^5$R$^6$)—,
"B" is alkylene or alkenylene,
R$^1$ is alkyl or alkenyl, wherein the alkyl can be substituted by halogen, amino, cycloalkyl, aryl, imidazole or a pyridine ring, and further the amino can be substituted by alkyl, acyl, alkoxycarbonyl, cycloalkyloxycarbonyl or arylalkoxycarbonyl,
R$^2$ is alkyl, alkenyl or arylalkyl,
R$^3$ is a pyridine ring,
R$^4$ is hydrogen,
R$^5$ and R$^6$ are hydrogen, and
X is =O.

Further, compounds wherein R$^1$ is alkyl having three or more carbon atoms, and R$^2$ is alkyl or arylalkyl are particularly preferable among them.

Compounds or salts thereof wherein the respective groups defined in the general formula [1] are the following groups are more preferable.
"A" is —(NR$^4$)— or —(CR$^5$R$^6$)—
"B" is alkylene or alkenylene,
R$^1$ is alkyl, alkenyl or cycloalkyl, wherein the alkyl can be substituted by halogen, hydroxyl, amino, cycloalkyl, aryl, carboxyl, alkoxycarbonyl, aryloxycarbonyl, aminocarbonyl, a pyridine ring or a thiophene ring, and further hydrogen in each amino, hydroxyl and aminocarbonyl in R$^1$ can be substituted by alkyl, aryl, arylalkyl, acyl, alkoxycarbonyl, cycloalkyloxycarbonyl or arylalkoxycarbonyl,
R$^2$ is cycloalkyl or cycloalkylalkyl,
R$^3$ is a pyridine ring,
R$^4$ is hydrogen,
R$^5$ and R$^6$ are hydrogen, and
X is =O.

The most preferred specific examples of the present compound are the following compounds and salts thereof.

1-[2-(1-Adamantyl)ethyl]-1-pentyl-3-[3-(4-pyridyl)propyl]urea

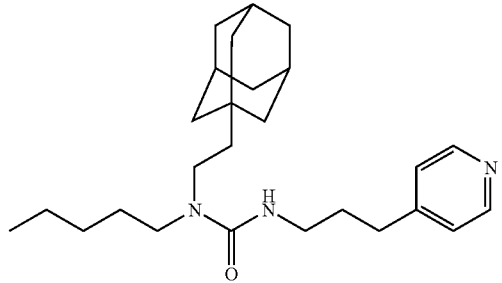

1-[2-(1-Adamantyl)ethyl]-3-[3-(4-pyridyl)propyl]-1-(3,3,3-trifluoropropyl)urea

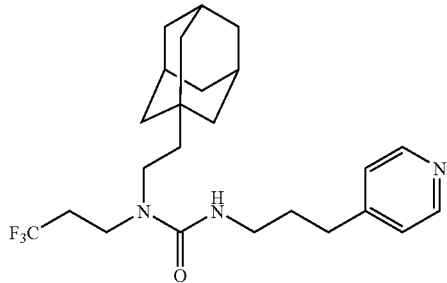

7
1-[2-(1-Adamantyl)ethyl]-1-(2-butenyl)-3-[3-(4-pyridyl)propyl]urea
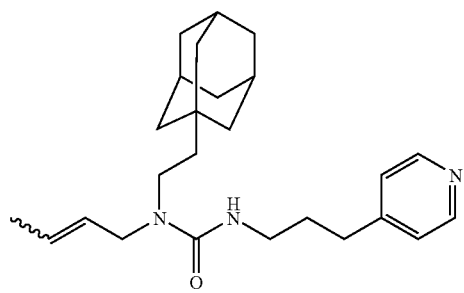
1-[2-(1-Adamantyl)ethyl]-1-[2-[N-(t-butoxycarbonyl)-N-methylamino]ethyl]-3-[3-(4-pyridyl)propyl]urea
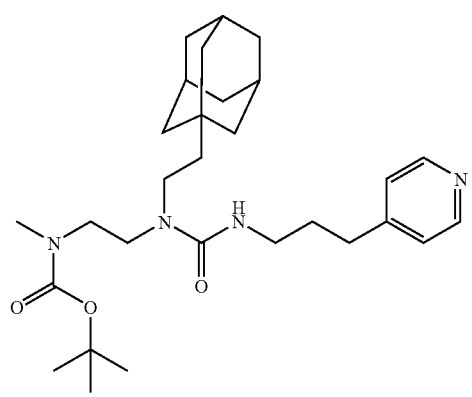
1-[3-(1-Adamantyl)propyl]-1-propyl-3-[3-(4-pyridyl)propyl]urea
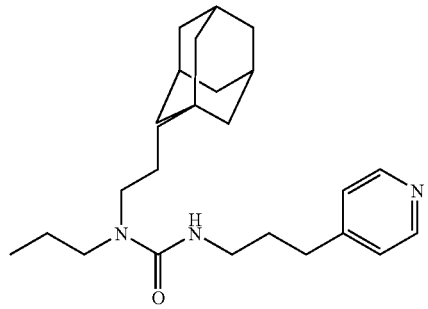
8
(Z)-1-[2-(1-Adamantyl)ethyl]-1-pentyl-3-[3-(4-pyridyl)-2-propenyl]urea
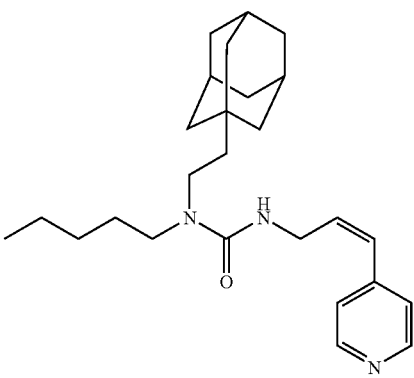
(−)-1-[2-(1-Adamantyl)ethyl]-3-[2-methyl-3-(4-pyridyl)propyl]-1-pentylurea
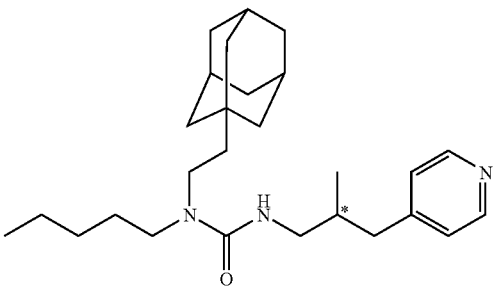
1-[2-(1-Adamantyl)ethyl]-3-[1-methyl-3-(4-pyridyl)propyl]-1-pentylurea
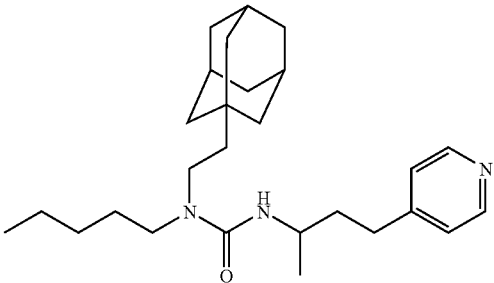

9

(+)-1-[2-(1-Adamantyl)ethyl]-1-[2-[N-(t-butoxycarbonyl)-N-methylamino]ethyl]-3-[2-methyl-3-(4-pyridy)propyl]urea

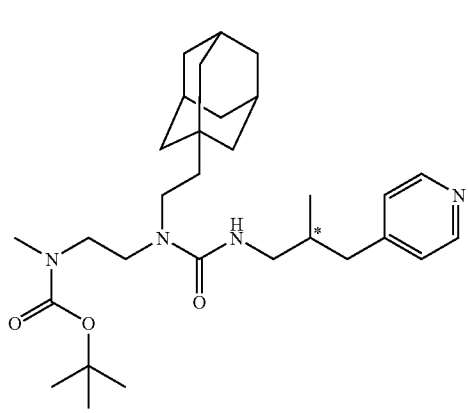

5-(4-Pyridyl)valeric acid N-[2-(1-adamantyl)ethyl]-N-pentylamide

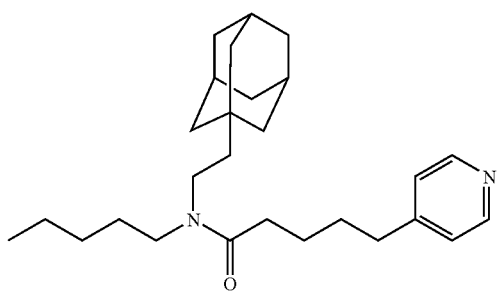

3-(4-Pyridylmethylthio)propionic acid N-[2-(1-adamantyl)ethyl]-N-pentylamide

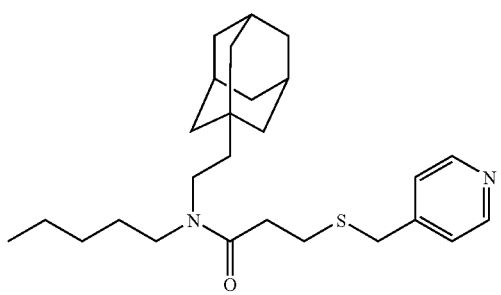

10

2-[2-(4-Pyridyl)ethylthiol]acetic acid N-[2-(1-adamantyl)ethyl]-N-pentylamide

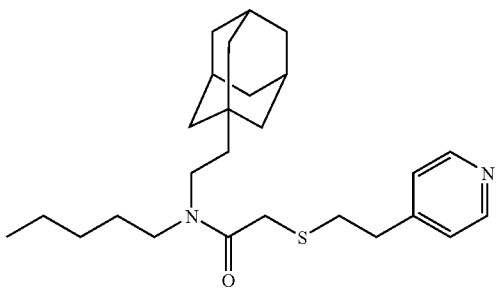

6-(4-Pyridyl)caproic acid N-[2-(1-adamantyl)ethyl]-N-pentylamide

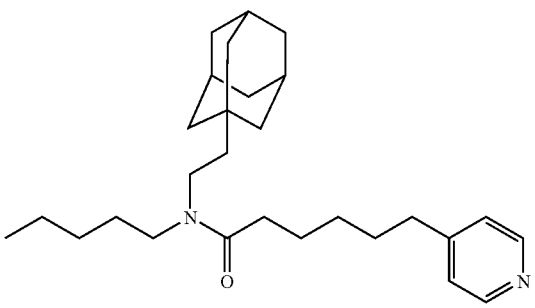

cis-1-[2-(1-Adamantyl)ethyl]-1-pentyl-3-[2-(4-pyridyl)cyclopropylmethyl]urea

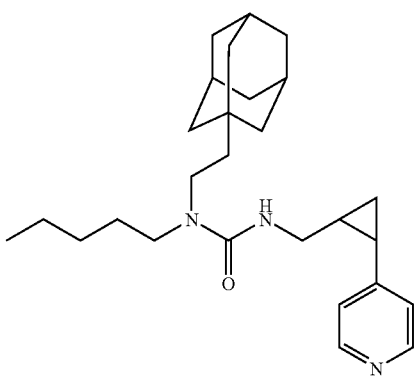

11
1-[2-(1-Adamantyl)ethyl]-3-[2-methyl-3-(4-pyridyl)propyl]-1-pentylurea
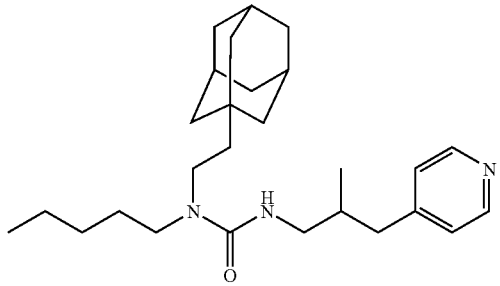
1-[2-(1-Adamantyl)ethyl]-1-[2-[N-(t-butoxycarbonyl)-N-methylamino]ethyl]-3-[2-methyl-3-(4-pyridyl)propyl]urea
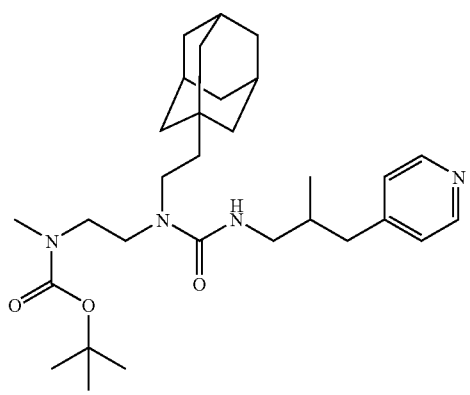
(E)-1-[2-(1-Adamantyl)ethyl]-1-pentyl-3-[3-(4-pyridyl)-2-propenyl]urea
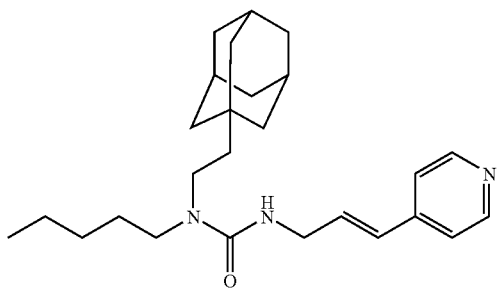
12
(+)-1-[2-(1-Adamantyl)ethyl]-3-[2-methyl-3-(4-pyridyl)propyl]-1-pentylurea
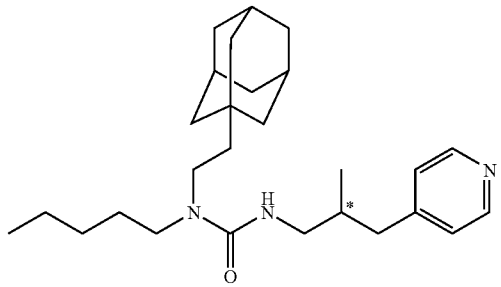
1,1-Dibutyl-3-[3-(4-pyridyl)propyl]urea
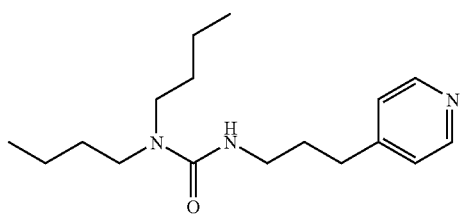
3-[2-Methyl-3-(4-pyridyl)propyl]-1-pentyl-1-phenethylurea
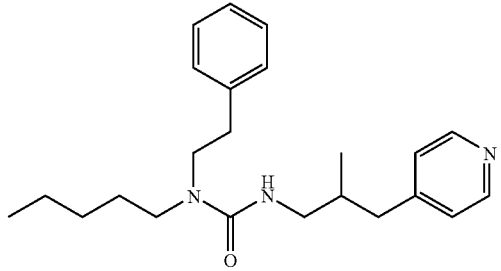
5-(4-Pyridyl)valeric acid N-pentyl-N-phenethylamide
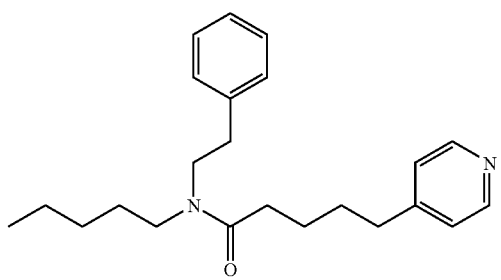

1-(2-Cyclohexylethyl)-3-[2-methyl-3-(4-pyridyl)propyl]-1-pentylurea

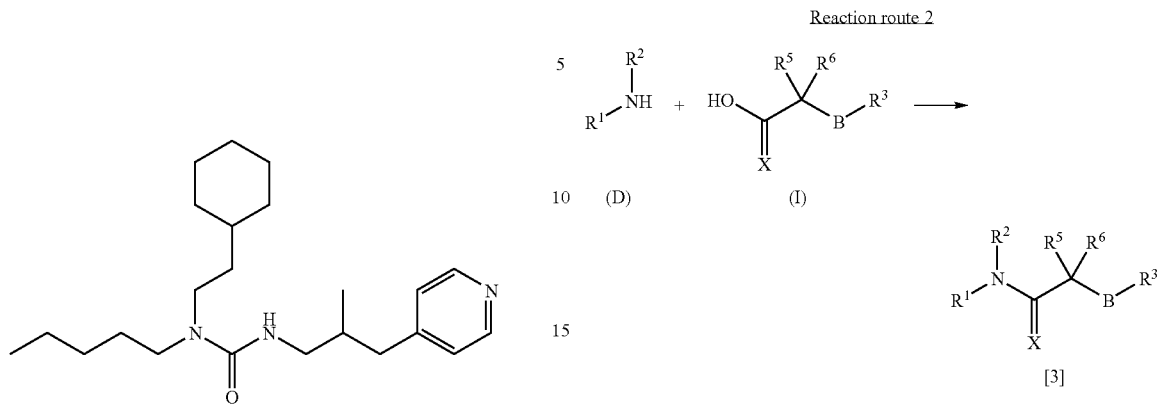

Reaction route 2

Next, the present compounds can be prepared according to, for example, the following reaction routes 1 to 3 but can be prepared by various reaction routes other than these reaction routes. Detailed synthetic methods will be described later in Examples.

The present compound [3] is obtained by reacting primary amine (B) or secondary amine (D) synthesized by the reaction route 1 with carboxylic acid (I) in the presence of a condensing agent [for example, 1-ethyl-3-(3-dimethylaminopropyl)carbodiimide hydrochloride].

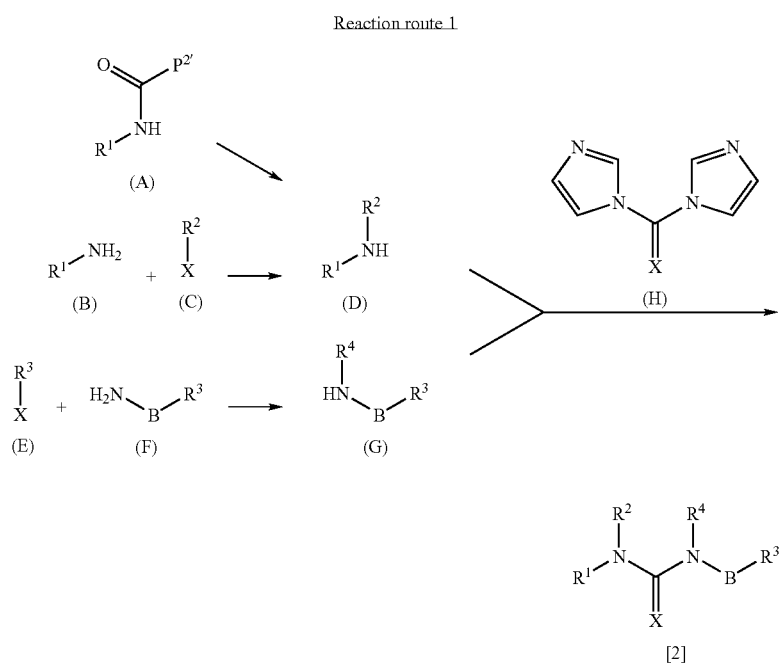

Reaction route 1

Secondary amine (D) can be obtained by reducing amide (A) or by reacting primary amine (B) with compound (C) having a leaving group. ($R^1$ and $R^2$ can be exchanged each other in the above chemical reaction formulae.) Similarly, secondary amine (G) can be obtained by reacting compound (E) having a leaving group with primary amine (F). The present compound [2] is obtained by reacting primary amine (B) or secondary amine (D) with primary amine (F) or secondary amine (G) in the presence of condensing agent (H) [for example, 1,1'-carbonyldiimidazole].

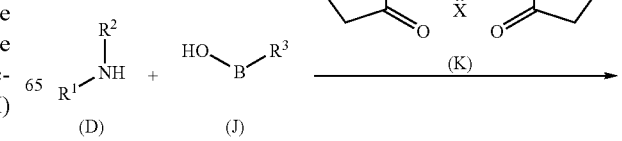

Reaction route 3

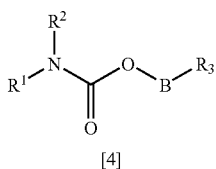

[4]

The present compound [4] is obtained by reacting primary amine (B) or secondary amine (D) synthesized by the reaction route 1 with alcohol (J) in the presence of condensing agent (K) [for example, N,N'-disuccinimidyl carbonate].

When the reactants have thiol group(s), hydroxyl group(s) or amino group(s) in their molecule in the above-mentioned synthetic methods, these groups can be protected with suitable protecting groups, if necessary, and these protecting groups can be removed after the reactions by conventional methods. When the reactants have carboxyl group(s) in their molecule, the carboxyl group(s) can be esterified, if necessary, and the ester can be converted into the carboxylic acid by general methods such as hydrolysis.

The compounds obtained by the above-mentioned synthetic methods can be converted into the above-mentioned salts by conventional methods.

Angiogenesis inhibition tests were carried out in order to study utility of the present compounds obtained by the above-mentioned synthetic methods. Details will be described later in the section of pharmacological tests. The present compounds were found to have strong inhibitory actions on in vitro angiogenesis evaluation models using human endothelial cells, and in vivo angiogenesis induced by high oxygen exposure in the retina. The present compounds are useful as angiogenesis inhibitors, and preventives, therapeutic agents and inhibitors for diseases in which angiogenesis participates, particularly diabetic retinopathy, retinopathy of prematurity, macular degeneration, neovascular glaucoma, retinal vein occlusion, retinal artery occlusion, pterygium, rubeosis, corneal neovasculature, solid tumors, hemangioma, proliferation and transfer of tumors, and the like.

The present compounds can be administered parenterally or orally. Examples of dosage forms are ophthalmic solutions, eye ointments, ophthalmic tissue injections such as subconjunctival injections, conjunctival depots, implants, cul-de-suc inserts, intravenous injections, tablets, capsules, powders, granules and percutaneous absorption preparations. These (including DDS preparations) can be prepared using known techniques. For example, the ophthalmic solutions can be prepared by optionally adding an isotonic agent, a buffer, a pH adjustor, a solubilizer, a thickener, a stabilizer, a preservative or a soothing agent as an additive. Stable ophthalmic solutions can be obtained by adding the pH adjustor, the thickener, a dispersant or the like and suspending the drugs. It is desirable to adjust pH of the ophthalmic solutions to 4.0 to 8.0, and it is desirable to adjust an osmotic pressure ratio to about 1.0.

Examples of isotonic agents are glycerin, propylene glycol, sodium chloride, potassium chloride, sorbitol and mannitol.

Examples of buffers are phosphoric acid, phosphates, citric acid, acetic acid, ε-aminocaproic acid and trometamol.

Examples of pH adjustors are hydrochloric acid, citric acid, phosphoric acid, acetic acid, sodium hydroxide, potassium hydroxide, sodium carbonate and sodium hydrogencarbonate.

Examples of solubilizers and dispersants are polysorbate 80, polyoxyethylene hydrogenated castor oil 60, macrogol 4000, purified soybean lecithin and polyoxyethylene (160) polyoxypropylene (30) glycol.

Examples of thickeners are cellulosic polymers such as hydroxypropylmethylcellulose and hydroxypropylcellulose, polyvinyl alcohol and polyvinylpyrrolidone. Examples of stabilizers are edetic acid and disodium edetate.

Examples of preservatives are widely-used sorbic acid, potassium sorbate, benzalkonium chloride, benzethonium chloride, methyl p-hydroxybenzoate, propyl p-hydroxybenzoate and chlorobutanol, and these preservatives can be used in combination.

Examples of soothing agents are chlorobutanol, benzyl alcohol and lidocaine.

The dosage of the present compound can be appropriately selected depending on symptoms, age, dosage form and the like. For example, the ophthalmic solutions can be instilled once to several times per day with a usual concentration of 0.001 to 10% (w/v), preferably 0.01 to 5% (w/v).

Preparation examples of intermediates, preparation examples of the present compounds, formulation examples and results of pharmacological tests are shown below. These examples do not limit the scope of the present invention, but are intended to make the present invention more clearly understandable.

BEST MODE FOR CARRYING OUT THE INVENTION

[A] Preparation Examples of Intermediates

Intermediate Preparation Example 1

2-(1-Adamantyl)-N-pentylethylamine hydrochloride (Intermediate No. 1-1)

Pentylamine (2.69 ml, 23.2 mmol), potassium carbonate (2.14 g, 15.5 mmol) and sodium iodide (2.30 g, 15.3 mmol) were added to a solution of 2-(1-adamantyl)ethyl methanesulfonate (2.07 g, 8.01 mmol) in ethanol (45.8 ml), and the mixture was refluxed for 17 hours. The reaction mixture was concentrated under reduced pressure, and the concentrate was diluted with chloroform (100 ml). The whole was washed with a 1 N aqueous sodium hydroxide solution (100 ml) and a saturated aqueous sodium chloride solution (100 ml) successively, and the organic layer was dried over magnesium sulfate. The solvent was evaporated under reduced pressure, and the obtained residue was purified by silica gel column chromatography. A 4 N solution of hydrogen chloride in ethyl acetate (3.1 ml) was added to the solution of the obtained free body (1.52 g, 6.10 mmol) of the target compound in ethyl acetate (0.50 ml). The precipitated solid was washed with ethyl acetate and filtered off to give the target compound (1.33 g, 60%).

IR (KBr): 2924, 2850, 2519, 1456 cm$^{-1}$ mp: 263.0-264.5° C.

The following compounds were obtained in a manner similar to Intermediate Preparation Example 1. Some target compounds were not isolated in the form of hydrochlorides.

N'-[2-(1-Adamantyl)ethyl]-N-(benzyloxycarbonyl)-N-methylethylenediamine (Intermediate No. 1-2)

IR (neat): 2901, 2844, 1704 cm$^{-1}$ 2-(1-Adamantyl)-N-(cyclopentylmethyl)ethylamine hydrochloride (Intermediate No. 1-3)

IR (KBr): 2907, 2847, 1452 cm$^{-1}$
mp: 300.0-310.0° C.

N'-[2-(1-Adamantyl)ethyl]-N-(t-butoxycarbonyl)-N-methylethylenediamine (Intermediate No. 1-4)

IR (neat): 3307, 2902, 2846, 1698 cm$^{-1}$ 2,2'-Di(1-adamentyl)diethylamine hydrochloride (Intermediate No. 1-5)

IR (KBr): 2900, 2845, 2735, 2453 cm$^{-1}$
mp: 325° C.

2-(1-Adamantyl)-N-propylethylamine (Intermediate No. 1-6)

IR (neat): 3276, 2903, 2846, 1450 cm$^{-1}$

N'-[2-(1-Adamantyl)ethyl]-N,N-dimethylethylenediamine dihydrochloride (Intermediate No. 1-7)

IR (KBr): 3424, 2901, 2846, 2445 cm$^{-1}$
mp: 254.5-259.0° C.

2-(1-Adamantyl)-N-cyclopentylethylamine hydrochloride (Intermediate No. 1-8)

IR (KBr): 2910, 2846, 2771, 2450 cm$^{-1}$
mp: 300-312° C.

2-(1-Adamantyl)-N-cyclopropylethylamine (Intermediate No. 1-9)

IR (neat): 3272, 2901, 2845 cm$^{-1}$ 2-(1-Adamantyl)-N-(2-methoxyethyl)ethylamine hydrochloride (Intermediate No. 1-10)

IR (KBr): 2909, 2846, 2792, 1451 cm$^{-1}$
mp: 278.5-281.5° C.

(1-Adamantyl)-N-(2-propynyl)ethylamine (Intermediate No. 1-11)

IR (neat): 2900, 2845, 1450 cm$^{-1}$

N-Pentyl-2-(2-pyridyl)ethylamine (Intermediate No. 1-12)

IR (neat): 3305, 2927, 2857, 1591 cm$^{-1}$ 2-(1-Adamantyl)-N-benzylethylamine hydrochloride (Intermediate No. 1-13)

IR (KBr): 2900, 2846, 2750, 2528, 2468, 2372, 1585 cm$^{-1}$
mp: 264.0-265.0° C.

2-(1-Adamantyl)-N-furfurylethylamine hydrochloride (Intermediate No. 1-14)

IR (KBr): 3456, 2903, 2846, 2741, 2426 cm$^{-1}$
mp: 225.0-233.0° C.

2-(1-Adamantyl)-N-butylethylamine (Intermediate No. 1-15)

IR (neat): 2903, 1683, 1450 cm$^{-1}$

2-Cyclohexyl-N-(2-thienyl)methylethylamine hydrochloride (Intermediate No. 1-16)

N-Pentylphenethylamine hydrochloride (Intermediate No. 1-17)

IR (KBr): 3028, 2957, 2786, 1456 cm$^{-1}$
mp: 260.0-285.0° C.

2-Cyclohexyl-N-butylethylamine hydrochloride (Intermediate No. 1-18)

IR (KBr): 2921, 2853, 2794, 2739, 2442, 1590, 1484, 1451 cm$^{-1}$
mp: ≦250° C.

2-Cyclohexyl-N-pentylethylamine hydrochloride (Intermediate No. 1-19)

IR (KBr): 2924, 2793, 1451 cm$^{-1}$
mp: ≦250° C.

N-(t-Butoxycarbonyl)-N'-(2-cyclohexylethyl)-N-methylethylenediamine (Intermediate No. 1-20)

IR (neat): 3350, 2923, 2850, 1697, 1481, 1449 cm$^{-1}$

N'-(2-Cyclohexylethyl)-N,N'-dimethylethylenediamine (Intermediate No. 1-21)

IR (neat): 3310, 2921, 2850, 2815, 1448 cm$^{-1}$

N-[2-(1-Adamantyl)ethyl]-3-(4-pyridyl)propylamine (Intermediate No. 1-22)

IR (neat): 3291, 2902, 2845, 1602, 1450 cm$^{-1}$ 2-(1-Adamantyl)-N-isopropylethylamine hydrochloride (Intermediate No. 1-23)

IR (KBr): 2909, 2846, 2754, 2464, 1588, 1476, 1451 cm$^{-1}$
mp: 266.0-269.5° C.

N-(2-Piperidinoethyl)pentylamine (Intermediate No. 1-24)

IR (neat): 2932, 2854, 1466 cm$^{-1}$ 2-(1-Adamantyl)-N-[(2-methylthiazol-4-yl)methyl]ethylamine (Intermediate No. 1-25)

IR (neat): 2901, 2844, 1449 cm$^{-1}$

N-[2-(1-Adamantyl)ethyl]cinnamylamine (Intermediate No. 1-26)

IR(neat): 2901, 2845, 1449 cm$^{-1}$

N-[2-(1-Adamantyl)ethyl]-2-methyl-2-propenylamine (Intermediate No. 1-27)

IR (neat): 2902, 2845, 1450 cm$^{-1}$

N-[2-(1-Adamantyl)ethyl]-3-methyl-2-butenylamine (Intermediate No. 1-28)

IR (neat): 2903, 2846, 1450 cm$^{-1}$

N-[2-(1-Adamantyl)ethyl]decylamine hydrochloride (Intermediate No. 1-29)

IR (KBr): 2926, 2849, 2778, 2469 cm$^{-1}$
mp: 204.0-208.5° C.

N-[2-(1-Adamantyl)ethyl]hexylamine hydrochloride (Intermediate No. 1-30)

IR (KBr): 2909, 2848, 2766, 2446 cm$^{-1}$
mp: 230.0-243.0° C.

2-(1-Adamantyl)-N-(benzyloxy)ethylamine (Intermediate No. 1-31)

IR (neat): 2901, 2846, 1452 cm$^{-}$ 2-(1-Adamantyl)-N-[(2-thienyl)methyl]ethylamine hydrochloride (Intermediate No. 1-32)

IR (KBr): 2908, 2846, 2757, 2426 cm$^{-1}$
mp: 257.0-260.0° C.

N-[2-(1-Adamantyl)ethyl]-2-butenylamine (Intermediate No. 1-33)

IR (neat): 2901, 1450 cm$^{-1}$

N-[2-(1-Adamantyl)ethyl]allylamine (Intermediate No. 1-34)

IR (neat): 2902, 1450 cm$^{-1}$

N-[2-(1-Adamantyl)ethyl)cycopropylmethylamine (Intermediate No. 1-35)

IR (neat): 2901, 1450 cm$^{-1}$

N-[2-(1-Adamantyl)ethyl]-3,3,3-trifluoropropylamine hydrochloride (Intermediate No. 1-36)

IR (KBr): 2910, 2849, 2767, 2598, 2457 cm$^{-}$
mp: 300.0-310.0° C.

1-[2-(1-Adamantyl)ethyl]-2-(t-butoxycarbonyl)hydrazine (Intermediate No. 1-37)

IR (KBr): 3288, 2899, 1705 cm$^{-1}$
mp: 73.5-81.0° C.

N-(t-Butoxycarbonyl)-N-methyl-N'-phenethylethylene diamine (Intermediate No. 1-38)

IR (neat): 3326, 3025, 2975, 2930, 1694, 1454 cm$^{-1}$

N-(t-Butoxycarbonyl)-N-methyl-N-pentylethylenediamine (Intermediate No. 1-39)

IR (neat): 2958, 2929, 1694, 1457 cm$^{-1}$

N-(Benzyloxycarbonyl)-N-methyl-N'-phenethylethylene diamine (Intermediate No. 1-40)

IR (neat): 3309, 3027, 2936, 2824, 1698, 1454 cm$^{-1}$

N-(Benzyloxycarbonyl)N-methyl-N'-pentylethylenediamine (Intermediate No. 1-41)

IR (neat): 2928, 2858, 1703, 1455 cm$^{-1}$

2-Cyclohexyl-N-(2-methoxyethyl)ethylamine hydrochloride (Intermediate No. 1-42)

IR (KBr): 2923, 2855, 2784, 2478, 2444 cm$^{-1}$
mp: 205.0-208.0° C.

N-Ethyl-3,4,5-trimethoxyphenethylamine (Intermediate No. 1-43)

IR (neat): 3300, 2936, 2828, 1588, 1508, 1457, 1419, 1331, 1236, 1126, 1008 cm$^{-1}$ 5-[2-(Isopentylamino)ethyl]imidazole dihydrochloride (Intermediate No. 1-44)

IR (KBr): 2806, 2467, 1619, 1604, 1446, 1347, 1089, 914, 827, 735, 627, 622 cm$^{-1}$
mp: 235.2-238.0° C.

N-Cyclohexyl-3,4-dimethoxyphenethylamine (Intermediate No. 1-45)

IR (neat): 2928, 2852, 1591, 1515, 1463, 1449, 1416, 1261, 1236, 1155, 1139, 1029, 802, 761 cm$^{-1}$
bp: 170° C./210 Pa N-Cyclopropyl-3,4,5-trimethoxyphenethylamine (Intermediate No. 1-46)

IR (neat): 3304, 2932, 2832, 1588, 1505, 1459, 1418, 1332, 1236, 1126, 1009 cm$^{-1}$ N'-[2-(1-Adamantyl)ethyl]-N-(t-butoxycarbonyl)-N-methyl-1,3-propanediamine (Intermediate No. 1-47)

IR (neat): 3308, 2902, 2845, 1698, 1480 cm$^{-1}$

N-Cyclohexyl(phenyl)methyl-3-(4-methoxyphenyl)propylamine hydrochloride (Intermediate No. 1-48)

IR (KBr): 2928, 2857, 2765, 1592, 1510, 1455, 1230, 1064, 1033, 817 cm$^{-1}$
mp: 187.5-189.5° C.

N-Diphenylmethyl-3-phenylpropylamine (Intermediate No. 1-49)

IR (neat): 3024, 2931, 1601, 1493, 1452 cm$^{-1}$

N-Pentyl-3-phenylpropylamine hydrochloride (Intermediate No. 1-50)

IR (KBr): 3027, 2955, 2870, 2780, 2492, 2413 cm$^{-1}$
mp: 230.0-238.0° C.

N-Acetyl-N'-[2-(1-adamantyl)ethyl]ethylenediamine hydrochloride (Intermediate No. 1-51)

IR (neat): 2897, 2845, 2361, 1826, 1707, 1567 m$^{-1}$
mp: 245.0-247.0° C.

N-Isopentyl-3,3,3-trifluoropropylamine hydrochloride (Intermediate No. 1-52)

IR (KBr): 2961, 2800, 1253, 1173 m$^{-1}$
mp: ≦288° C.

N-[2-(1-Adamantyl)ethyl]-2,2,2-trifluoroethylamine hydrochloride (Intermediate No. 1-53)

IR (KBr): 2904, 2849, 1273, 1233, 1176, 1145 m$^{-1}$
mp: ≦263.0-265.0° C.

3-Cyclohexyl-N-propylpropylamine hydrochloride (Intermediate No. 1-54)

IR (KBr): 2924, 2854, 2779 m$^{-1}$
mp: 234.6-235.4° C.

N'-[3-(1-Adamantyl)propyl]-N-(t-butoxycarbonyl)-N-methylethylenediamine (Intermediate No. 1-55)

$^1$H-NMR (400 MHz, CDCl$_3$) δ 0.99-1.10 (m, 2H), 1.32-1.52 (m, 17H), 1.55-1.65 (m, 4H), 1.70 (d, J=11.8 Hz, 3H), 1.93 (s, 3H), 2.58 (t, J=7.2 Hz, 2H), 2.77 (br, 2H), 2.91 (s, 3H), 3.33 (br, 2H)

Intermediate Preparation Example 2

4-(3-Aminopropyl)pyridine (Intermediate No. 2-1)

N-[3-(4-pyridyl)propyl]phthalimide (67.1 g, 252 mmol) was mixed with methanol (504 ml) and hydrazine monohydrate (18.3 ml, 378 mmol), and the mixture was refluxed for three hours. The reaction mixture was allowed to stand, then the resulting insoluble matter was filtered out, and the filtrate was concentrated under reduced pressure. Chloroform (1 L) and a 4 N aqueous sodium hydroxide solution (500 ml) were added to the resulting residue. After separation, the organic layer was dried over sodium sulfate and concentrated under reduced pressure. Then the obtained concentrate was distilled under reduced pressure to give the target compound (20.5 g, 60%) as a colorless oily matter.
IR (neat): 3362, 2933, 1603 cm$^{-1}$
bp: 76.0-79.0° C./40 Pa
The following compounds were obtained in a manner similar to Intermediate Preparation Example 2.

3-(4-Pyridyl)-2-propenylamine (Intermediate No. 2-2)

IR (neat): 3280, 3024, 1599 cm$^{-1}$

2-(4-Pyridyloxy)ethylamine (Intermediate No. 2-3)

IR (KBr): 3298, 3102, 1610, 1216, 1049 cm$^{-1}$
mp: 108.0-111.5° C.

3-(4-Quinolyl)-2-propenylamine (Intermediate No. 2-4)

IR (neat): 3270, 2944, 1585, 1568, 1508 cm$^{-1}$

Intermediate Preparation Example 3

2-(1-Adamantyl)-N-methylethylamine (Intermediate No. 3-1)

A solution of 1-adamantaneacetic acid N-methylamide (1.54 g, 7.45 mmol) in tetrahydrofuran (15.0 ml) was added dropwise to a solution of lithium aluminum hydride (569 mg, 15.0 mmol) in diethyl ether (34.0 ml) under ice-cooling over five minutes. The mixture was refluxed for six hours and then stirred under ice-cooling again, ethyl acetate was added to the reaction mixture to treat excessive lithium aluminum hydride, and then the whole was extracted with 1 N hydrochloric acid (50 ml) twice. A 4 N aqueous sodium hydroxide solution was added to the extract to basify it, and the whole was extracted with diethyl ether (80 ml). The organic layer was washed with a saturated aqueous sodium chloride solution (60 ml) and dried over magnesium sulfate. The solvent was evaporated under reduced pressure to give the target compound (890 mg, 66%).
IR (neat): 2902, 2845, 1449 cm$^{-1}$
The following compounds were obtained in a manner similar to Intermediate Preparation Example 3. The compounds could be converted into hydrochlorides with a 4 N solution of hydrogen chloride in ethyl acetate.

2-(1-Adamantyl)-N-ethylethylamine hydrochloride (Intermediate No. 3-2)

IR (KBr): 2896, 2847, 2753, 2468, 1610 cm$^{-1}$
mp: 230-245° C.

N-Methyl-3-(4-pyridyl)propylamine (Intermediate No. 3-3)

IR(neat): 3292, 2934, 1602 cm$^{-1}$

1-Adamantyl-N-propylmethylamine hydrochloride (Intermediate No. 3-4)

IR (KBr): 2905, 1584, 1451 cm$^{-1}$
mp: 340° C.

2-(1-Adamantyl)-N-methylethylamine hydrochloride (Intermediate No. 3-5)

IR (KBr): 3422, 2900, 2846, 2676, 2450, 1630 cm$^{-1}$
mp: 200-220° C.

3-(1-Adamantyl)-N-propylpropylamine hydrochloride (Intermediate No. 3-6)

IR (KBr): 2899, 2467, 1449 cm$^{-1}$
mp: 159.5-162.0° C.

1-Adamantyl-N-pentylmethylamine hydrochloride (Intermediate No. 3-7)

IR (KBr): 2916, 2603, 2509, 2418, 1477 cm$^{-1}$
mp: 170-235° C.

N-[3-(1-Adamantyl)propyl]pentylamine hydrochloride (Intermediate No. 3-8)

IR (KBr): 2901, 2847, 1466, 1453 cm$^{-1}$
mp: 199-224° C.

N-[2-(1-Adamantyl)ethyl]-4,4,4-trifluorobutylamine hydrochloride (Intermediate No. 3-9)

IR (KBr): 3422, 2908, 2852, 2770, 2518, 1452, 1255, 1148 cm$^{-1}$
mp: 243-274° C.

N-[2-(1-Adamantyl)ethyl]-5,5,5-trifluoropentylamine (Intermediate No. 3-10)

IR (neat): 2903, 2846, 1450, 1255, 1142 cm$^{-1}$

N-[3-(1-Adamantyl)propyl]butylamine hydrochloride (Intermediate No. 3-11)

IR (KBr): 2904, 2847, 2756, 1453 cm$^{-1}$
mp: 275.0-276.8° C.

3-(1-Adamantyl)-N-(2,2,2-trifluoroethyl)propylamine hydrochloride (Intermediate No. 3-12)

IR (KBr): 2902, 2850, 2739, 1274, 1258, 1176, 1139 cm$^{-1}$
mp: 262.0-268.0° C.

4-(1-Adamantyl)-N-ethylbutylamine hydrochloride (Intermediate No. 3-13)

IR (KBr): 2901, 2847, 2457, 1451 cm$^{-1}$
mp: 224-230° C.

4-(1-Adamantyl)-N-propylbutylamine hydrochloride (Intermediate No. 3-14)

IR (KBr): 2899, 2848, 2751, 2410, 1451 cm$^{-1}$
mp: 234-249° C.

N-(1-Adamantyl)-N'-propylethylenediamine dihydrochloride (Intermediate No. 3-15)

IR (KBr): 2927, 2719, 2508, 2429, 1471 cm$^{-1}$
mp: 288.5-289.5° C.

Intermediate Preparation Example 4 t-Butyl 3-[N-[2-(1-adamantyl)ethyl]amino]propionate hydrochloride (Intermediate No. 4-1)

2-(1-Adamantyl)ethylamine hydrochloride (1.0 g, 4.6 mmol) was dissolved in ethanol (10 ml), triethylamine (0.65 ml, 4.6 mmol) and t-butyl acrylate (0.75 ml, 5.1 mmol) were added to the solution under ice-cooling, and then the mixture was stirred at room temperature overnight. The reaction mixture was concentrated under reduced pressure, and a 1 N aqueous sodium hydroxide solution (30 ml) and ethyl acetate (50 ml) were added to the resulting residue. After separation, the ethyl acetate layer was washed with water (50 ml) and a saturated aqueous sodium chloride solution (50 ml) successively, dried over anhydrous magnesium sulfate and concentrated under reduced pressure. Then the obtained concentrate was purified by silica gel column chromatography. The obtained oily matter (0.50 g, 1.6 mmol) was dissolved in diethyl ether (20 ml), and a 4 N solution of hydrogen chloride in ethyl acetate (1.0 ml, 4.0 mmol) was added thereto under ice-cooling to precipitate solids. These solids were filtered off with diethyl ether to give the target compound (0.33 g, 23%).

IR (KBr): 2902, 2846, 1733, 1166 cm$^{-1}$
mp: 210° C.

The following compounds were obtained in a manner similar to Intermediate Preparation Example 4. Some target compounds were not isolated in the form of hydrochlorides.

Methyl 3-[N-(2-cyclohexylethyl)amino]propionate hydrochloride (Intermediate No. 4-2)

IR (KBr): 2924, 2853, 2792, 1736, 1455, 1439 cm$^{-1}$
mp: 185.0-187.5° C.

t-Butyl 3-[N-(2-cyclohexylethyl)amino]propionate (Intermediate No. 4-3)

IR (neat): 2977, 2922, 2850, 1728, 1449 cm$^{-1}$ t-Butyl 3-[N-[3-(4-pyridyl)propyl]amino]propionate hydrochloride (Intermediate No. 4-4)

IR (neat): 3322, 2977, 2933, 1724, 1602, 1367, 1153 cm$^{-1}$

Intermediate Preparation Example 5

5-(4-Pyridyl)valeric acid (Intermediate No. 5-1)

N,N-Dimethylformamide (17 ml) was added to a mixture of (benzyloxycarbonylmethyl)triphenylphosphonium bromide (4.60 g, 9.36 mmol) and 6-(4-pyridyl)acrolein oxalate (1.90 g, 8.51 mmol), and the whole was stirred under ice-cooling. Potassium carbonate (4.70 g, 34.0 mmol) was added thereto, and the temperature was raised to room temperature. The whole was stirred overnight, then the reaction mixture was diluted with ethyl acetate (100 ml), and the whole was washed with water (100 ml) twice and saturated brine (50 ml) successively. The organic layer was dried over sodium sulfate, and ethyl acetate was evaporated under reduced pressure. The obtained residue was purified by silica gel column chromatography to give 5-(4-pyridyl)valeric acid-2,4-diene benzyl ester (2.29 g, quantitatively) as a pale yellow oily matter.

Next, methanol (42 ml) and acetic acid (1.0 ml, 18 mmol) were added to 5-(4-pyridyl)valeric acid-2,4-diene benzyl ester (2.25 g, 8.48 mmol), and a nitrogen gas was bubbled through the mixture for 10 minutes. Palladium hydroxide on carbon (catalytic amount) was added thereto, and the whole was stirred at room temperature under a hydrogen atmosphere overnight. The reaction mixture was filtered with Celite to remove the resulting insoluble matter, and the filtrate was concentrated under reduced pressure. Ethyl acetate (50 ml) was added to the solidified residue, and the mixture was stirred at room temperature for three hours. The resulting crystals were filtered off to give the target compound (1.00 g, 66%) as pale yellow crystals.

IR (KBr): 2943, 1719, 1636, 1605 cm$^{-1}$
mp: 155.0-180.0° C.

Intermediate Preparation Example 6

3-[N-(2-Cyclohexylethyl)amino]propionamide hydrochloride (Intermediate No. 6-1)

Trifluoroacetic acid (6 ml) was added to t-butyl 3-[N-(2-cyclohexylethyl)amino]propionate (Intermediate No. 4-3) (2.0 g, 7.8 mmol) under ice-cooling. The mixture was stirred overnight, and then the reaction mixture was concentrated under reduced pressure. A 4 N solution of hydrogen chloride in ethyl acetate was added to the residue, the whole was concentrated under reduced pressure, and the resulting crystals were filtered off with diethyl ether to give 3-[N-(2-cyclohexylethyl)amino]propionic acid hydrochloride (1.5 g, 96%).

Next, tetrahydrofuran (8 ml) was added to 3-[N-(2-cyclohexylethyl)amino]propionic acid hydrochloride (1.0 g, 4.2 mmol), and the mixture was stirred at room temperature. Di-t-butyl carbonate (1.1 g, 5.1 mmol) and triethylamine (1.3 ml, 9.3 mmol) were added to the mixture, the whole was stirred overnight, and then a 5% aqueous citric acid solution (10 ml) was added to the reaction mixture. The whole was extracted with chloroform (60 ml), and the obtained organic layer was washed with saturated brine (20 ml), dried over magnesium sulfate and concentrated under reduced pressure. The residue was purified by silica gel column chromatography to give 3-[N-(t-butoxycarbonyl)-N-(2-cyclohexylethyl) amino]propionic acid (0.79 g, 62%) as a colorless oily matter.

Next, anhydrous tetrahydrofuran (7 ml) was added to 3-[N-(t-butoxycarbonyl)-N-(2-cyclohexylethyl)amino]propionic acid (0.59 g, 2.0 mmol), and the mixture was stirred at −78° C. N-Methylmorpholine (0.22 ml, 2.0 mmol) and a solution of isobutyl chloroformate (0.38 ml, 2.9 mmol) in tetrahydrofuran (3 ml) were added successively to the mixture. After one hour, a 28% aqueous ammonia solution (6.0 ml, 9.8 mmol) was added to the reaction mixture, and the whole was stirred for 1.5 hours. Chloroform (50 ml) was added thereto, the temperature was raised to room temperature, and the whole was washed with a saturated aqueous sodium hydrogencarbonate solution (20 ml) and saturated brine (20 ml) successively. The organic layer was dried over magnesium sulfate and concentrated under reduced pressure, and the resulting residue was purified by silica gel column chromatography to give 3-[N-(t-butoxycarbonyl)-N-(2-cyclohexylethyl)amino] propionamide (0.34 g, 58%) as colorless crystals.

Next, a 4 N solution of hydrogen chloride in 1,4-dioxane (3.1 ml) was added to 3-[N-(t-butoxycarbonyl)-N-(2-cyclohexylethyl)amino]propionamide (0.37 g, 1.2 mmol), and the mixture was stirred at room temperature overnight. The reaction mixture was concentrated under reduced pressure, then diisopropyl ether was added to the resulting solid, and the solid was filtered off to give the target compound (0.30 g, quantitatively) as colorless crystals.

IR (KBr): 3386, 3196, 2921, 2852, 2808, 1705, 1656, 1452 cm$^{-1}$ mp: 165.0° C.

Intermediate Preparation Example 7

Di-5-hexenylamine (Intermediate No. 7-1)

N,N-Dimethylformamide (28 ml) was added to 3-aminopropionitrile (0.98 g, 14 mmol), and the mixture was stirred at room temperature. 6-Bromo-1-hexene (5.0 g, 31 mmol), sodium iodide (11 g, 73 mmol) and potassium carbonate (5.8 g, 42 mmol) were added to the mixture, and the whole was stirred overnight. The reaction mixture was diluted with diethyl ether (100 ml), and the whole was washed with water (100 ml, twice) and saturated brine (50 ml) successively. The organic layer was dried over sodium sulfate and concentrated under reduced pressure. The resulting residue was purified by silica gel column chromatography to give 3-(di-5-hexenyl) aminopropionitrile (2.2 g, 66%) as a colorless oily matter.

Next, ethanol (8.6 ml) and potassium hydroxide (0.85 g, 13 mmol) were added to 3-(di-5-hexenyl)aminopropionitrile (2.0 g, 8.6 mmol), and the obtained mixture was refluxed for 7.5 hours. The reaction mixture was allowed to stand, then water (150 ml) and chloroform (150 ml) were added to the reaction mixture. After separation, the organic layer was dried over sodium sulfate and concentrated under reduced pressure, and the resulting residue was purified by basic silica gel column chromatography to give the target compound (0.32 g, 21%) as a pale yellow oily matter.

IR (neat): 3076, 2976, 2928, 2856, 1679, 1640 cm$^{-1}$

The following compound was obtained in a manner similar to Intermediate Preparation Example 7.

Di-7-octenylamine (Intermediate No. 7-2)

IR (neat): 3075, 2976, 2926, 2854, 1640 cm$^{-1}$

Intermediate Preparation Example 8

N-[2-(1-Adamantyloxy)ethyl]propylamine hydrochloride (Intermediate No. 8-1)

2-(Propylamino)ethanol (2.4 g, 23 mmol) was mixed with 1-bromoadamantane (0.50 g, 2.3 mmol) and triethylamine (0.32 ml, 2.3 mmol), and the mixture was stirred at an external temperature of 100° C. for two hours, at 130° C. for five hours and at 150° C. for three hours. The reaction mixture was allowed to stand, then ethyl acetate (50 ml) was added to the reaction mixture, and the whole was washed with water (50 ml) twice and saturated brine (30 ml) successively. The organic layer was dried over sodium sulfate and concentrated under reduced pressure. The residue was separated by silica gel column chromatography, and then a 4 N solution of hydrogen chloride in ethyl acetate (2 ml) was added to the separated matter. The whole was concentrated under reduced pressure, and the resulting crystals were filtered off with ethyl acetate to give the target compound (0.16 g, 25%) as colorless crystals.

IR (KBr): 3544, 2907, 2502, 1584 cm$^{-1}$ mp: 232.0-232.7° C.

Intermediate Preparation Example 9

2-Propylaminoacetic acid N-(1-adamantyl)amide (Intermediate No. 9-1)

Ethanol (36 ml) was added to bromoacetic acid (5.00 g, 36.0 mmol), and the mixture was stirred under ice-cold water-cooling. Propylamine (14.8 ml, 180 mmol) was added to the mixture over one minute, and then the whole was stirred at an external temperature of 80° C. for 2.5 hours. A 4 N aqueous sodium hydroxide solution (27 ml) was added to the reaction mixture, the whole was concentrated under reduced pressure, then water (27 ml) and tetrahydrofuran (30 ml) were added to the concentrate, and the whole was stirred at room temperature. A solution of di-t-butyl carbonate (9.43 g, 43.2 mmol) in tetrahydrofuran (6 ml) was added thereto, and after 15 minutes, citric acid monohydrate was added thereto to weakly acidify the whole. The whole was extracted with ethyl acetate (150 ml). The organic layer was washed with water (100 ml) and saturated brine (50 ml) successively, dried over sodium sulfate and concentrated under reduced pressure. The resulting residue was separated by silica gel column chromatography to give 2-[N-(t-butoxycarbonyl)-N-propylamino]acetic acid (5.06 g, 65%) as a colorless solid.

Next, methylene chloride (208 ml) was added to a mixture of 2-[N-(t-butoxycarbonyl)-N-propylamino]acetic acid (4.52 g, 20.8 mmol) and 1-adamantaneamine (3.46 g, 22.9 mmol), and the whole was stirred at room temperature. N,N-Diisopropylethylamine (7.25 ml, 41.6 mmol) and O-(7-azabenzotriazol-1-yl)-N,N,N',N'-tetramethyluronium hexafluorophosphate (8.71 g, 22.9 mmol) were added thereto successively, and the whole was stirred overnight. The reaction mixture was concentrated under reduced pressure, and the residue was separated by silica gel column chromatography to give 2-[N'-(t-butoxycarbonyl)-N'-propylamino]acetic acid N-(1-adamantyl)amide (7.88 g, quantitatively) as a colorless oily matter. The obtained oily matter solidified at room temperature.

Next, a 4 N solution of hydrogen chloride in ethyl acetate (55 ml, 0.22 mol) was added to 2-[N-(t-butoxycarbonyl)-N'-propylamino]acetic acid N-(1-adamantyl)amide (7.68 g, 21.9 mmol), and the mixture was stirred at room temperature for one hour. The resulting crystals were filtered off with ethyl acetate and washed with ethyl acetate to give the target compound (5.97 g, 95%) as colorless crystals.

IR (KBr): 3272, 2906, 2848, 2589, 1676, 1562 cm$^{-1}$
mp: 278.0-.279.2° C.

Intermediate Preparation Example 10

N-(t-Butoxycarbonyl)-2-(4-pyridyloxy)ethylamine (Intermediate No. 10-1)

Di-t-butyl dicarbonate (380 mg, 1.74 mmol) and triethylamine (240 µl, 1.74 mmol) were added to a solution of the Intermediate No. 2-4 (200 g, 1.45 mmol) in tetrahydrofuran (5 ml) under ice-cooling, and the mixture was stirred at room temperature for 25 minutes. The reaction mixture was concentrated under reduced pressure, and the obtained concentrate was distributed between ethyl acetate (50 ml) and a saturated aqueous sodium hydrogencarbonate solution (50 ml). The aqueous layer was further extracted with chloroform (50 ml), and the combined organic layer was dried over anhydrous magnesium sulfate. The solvent was evaporated under reduced pressure, and the obtained residue was purified by silica gel column chromatography to give the target compound (70 mg, 20.2%).

IR (neat): 3230, 2976, 1706, 1596 cm$^{-1}$

Intermediate Preparation Example 11

(RS)-2-Methyl-3-(4-pyridyl)propylamine (Intermediate No. 11-1)

N,N-Dimethylformamide (143 ml) was added to sodium hydride (5.36 g, 134 mmol) under a nitrogen atmosphere, and the mixture was stirred under ice-cooling. A solution of diethyl methylmalonate (11.7 g, 67.1 mmol) in N,N-dimethylformamide (40 ml) was added dropwise to the mixture over five minutes, after 10 minutes, 4-chloropicolyl hydrochloride (10.0 g, 61.0 mmol) was added thereto little by little over five minutes, and the temperature was raised to room temperature. After one hour, a saturated aqueous sodium hydrogencarbonate solution (500 ml) was added to the reaction mixture, and the whole was extracted with diethyl ether (400 ml). The organic layer was washed with water (100 ml) and saturated brine (50 ml) successively, dried over magnesium sulfate and concentrated under reduced pressure to give diethyl 2-methyl-2-(4-pyridylmethyl)malonate (17.2 g, quantitatively, containing sodium hydride oil) as a brown oily matter.

Next, 6 N hydrochloric acid (96.8 ml, 581 mmol) was added to diethyl 2-methyl-2-(4-pyridylmethyl)malonate (17.2 g, 64.6 mmol), and the mixture was refluxed overnight. The reaction mixture was allowed to stand, then washed with hexane (100 ml) to remove sodium hydride oil contained in diethyl 2-methyl-2-(4-pyridylmethyl)malonate and concentrated under reduced pressure. The resulting crystals were filtered off with ethyl acetate to give 2-methyl-3-(4-pyridyl) propionic acid (10.7 g, 82%) as pale pink crystals.

Next, chloroform (8 ml), thionyl chloride (2.2 ml, 30.6 mmol) and N,N-dimethylformamide (one drop) were added to 2-methyl-3-(4-pyridyl)propionic acid (1.69 g, 10.2 mmol), and the mixture was refluxed with stirring for one hour. The reaction mixture was concentrated under reduced pressure, then chloroform (8 ml) was added to the concentrate, and the whole was added slowly to a 28% aqueous ammonia solution stirred under ice-cooling. After 10 minutes, the temperature was raised to room temperature, and the whole was stirred overnight. The mixture was concentrated under reduced pressure, ethyl acetate (100 ml) was added to the concentrate, and the resulting insoluble matter was filtered out. The filtrate was concentrated under reduced pressure, the residue was purified by silica gel column chromatography, and the resulting crystals were filtered off with diethyl ether to give 2-methyl-3-(4-pyridyl)propionamide (0.72 g, 43%) as pale yellow crystals.

Next, anhydrous diethyl ether (20 ml) was added to lithium aluminum hydride (0.45 g, 12 mmol) under a nitrogen atmosphere, and the mixture was stirred under ice-cooling. A solution of 2-methyl-3-(4-pyridyl)propionamide (0.68 g, 4.1 mmol) in anhydrous methylene chloride (20 ml) was added dropwise to the mixture over five minutes, and the whole was stirred at room temperature overnight. The reaction mixture was stirred under ice-cooling again, ethyl acetate (5 ml) was added slowly. Then a 1 N aqueous sodium hydroxide solution was added slowly thereto at first, and the aqueous sodium hydroxide solution was added in a total amount of 100 ml. The whole was extracted with chloroform (100 ml), and the organic layer was dried over sodium sulfate and concentrated under reduced pressure to give the target compound (0.56 g, 90%) as a pale yellow oily matter.

IR (neat): 3293, 2957, 2925, 1602 cm$^{-1}$

The following compounds were obtained in a manner similar to Intermediate Preparation Example 11. Optically active substances could be obtained by carrying out optical resolution with an optically active acid.

2-(4-Pyridylmethyl)butylamine (Intermediate No. 11-2)

IR (neat): 3296, 3025, 2960, 2874, 1602 cm$^{-1}$

2-Benzyl-3-(4-pyridyl)propylamine (Intermediate No. 11-3)

IR (neat): 3296, 3062, 3025, 1602 cm$^{-1}$ 2,2-Bis(4-pyridylmethyl)ethylamine (Intermediate No. 11-4)

IR (neat): 3290, 3026, 2924, 1602, 1557 cm$^{-1}$ (−)-2-Methyl-3-(4-pyridyl)propylamine (Intermediate No. 11-5)

IR (neat): 3362, 3301, 2958, 1603 cm$^{-1}$
$[\alpha]^{20}_D$: −10.6° (MeOH, C1.0)

(+)-2-Methyl-3-(4-pyridyl)propylamine (Intermediate No. 11-6)

IR (neat): 3362, 3294, 2958, 1603 cm$^{-1}$
$[\alpha]^{20}_D$: +9.9° (MeOH, C1.0)

Intermediate Preparation Example 12

3-(4-Quinolyl)propylamine (Intermediate No. 12-1)

Under a nitrogen atmosphere, 10% palladium on carbon (catalytic amount) was added to a solution of 3-(4-quinolyl)-2-propenylamine (Intermediate No. 2-4) (188 mg, 1.02 mmol) in methanol (3 ml) at room temperature, and the mixture was stirred under a hydrogen atmosphere overnight. The reaction mixture was filtered with Celite, the solvent was evaporated under reduced pressure, and the obtained residue was distributed between ethyl acetate (30 ml) and a saturated aqueous ammonium chloride solution (30 ml). A 4 N aqueous sodium hydroxide solution (30 ml) was added to the aqueous layer, the whole was extracted with chloroform (100 ml), and the obtained organic layer was dried over anhydrous magnesium sulfate. The solvent was evaporated under reduced pressure to give the target compound (145 mg, 76.3%).

IR (neat): 3350, 2938, 1591, 1510 $cm^{-1}$

Intermediate Preparation Example 13

3-(4-Pyridyl)butylamine (Intermediate No. 13-1)

N,N-Dimethylformamide (33 ml) was added to a mixture of 4-acetylpyridine (2.00 g, 16.5 mmol) and (benzyloxycarbonyl)triphenylphosphonium bromide (8.94 g, 18.2 mmol), and the whole was stirred under ice-cooling. Potassium carbonate (9.12 g, 66.0 mmol) was added thereto, and the whole was stirred at an external temperature of 70° C. overnight. The reaction mixture was diluted with diethyl ether (100 ml), and the whole was washed with water (100 ml, twice) and saturated brine (50 ml) successively. The organic layer was dried over magnesium sulfate and concentrated under reduced pressure. The residue was purified by silica gel column chromatography to give benzyl 3-(4-pyridyl)-2-butenate (1.77 g, 42%: mixture of E body and Z body) as a pale yellow oily matter.

Next, methanol (31 ml) and acetic acid (0.71 ml, 12.4 mmol) were added to benzyl 3-(4-pyridyl)-2-butenate (1.75 g, 6.20 mmol), and a nitrogen gas was bubbled through the mixture at room temperature for 10 minutes. A catalytic amount of 10%-palladium on carbon was added to the mixture, and the whole was stirred under a hydrogen atmosphere at room temperature overnight. The resulting insoluble matter was filtered out, and the filtrate was concentrated under reduced pressure. The resulting crystals were filtered off with acetone to give 3-(4-pyridyl)butyric acid (0.61 g, 60%) as pale yellow crystals.

Next, chloroform (5 ml), thionyl chloride (0.80 ml, 11 mmol) and N,N-dimethylformamide (one drop) were added to 3-(4-pyridyl)butyric acid (0.60 g, 3.6 mmol), and the mixture was refluxed with stirring for one hour. The reaction mixture was concentrated under reduced pressure, then chloroform (5 ml) was added to the concentrate, and the whole was added slowly to a saturated ammonia/tetrahydrofuran solution (5 ml) stirred under ice-cooling. After 2.5 hours, the resulting insoluble matter was filtered out, and the filtrate was concentrated under reduced pressure. The residue was purified by silica gel column chromatograpy to give a mixture of 3-(4-pyridyl)butyramide and its oxidized olefin (0.34 g) as pale yellow crystals.

Next, anhydrous ether (8 ml) was added to lithium aluminum hydride (0.16 g, 4.2 mmol) under a nitrogen atmosphere, and the mixture was stirred under ice-cooling. A solution of 3-(4-pyridyl)butyramide (0.22 g, 1.4 mmol) in anhydrous methylene chloride (8 ml) was added dropwise to the mixture over two minutes, and then the whole was stirred at room temperature overnight. Ethyl acetate (1 ml) and a 1 N aqueous sodium hydroxide solution (20 ml) were added to the reaction mixture, and the whole was extracted with chloroform (50 ml). The organic layer was dried over anhydrous sodium sulfate and concentrated under reduced pressure. The residue was purified by silica gel column chromatography to give the target compound (0.15 g, 75%) as a pale yellow oily matter.

IR (neat): 3350, 2963, 2873, 1601 $cm^{-1}$

Intermediate Preparation Example 14

N-(4-Pyridyl)ethylenediamine (Intermediate No. 14-1)

Ethylenediamine (10.4 ml, 155 mmol) was added to 4-bromopyridine hydrochloride (3.00 g, 15.5 mmol) under a nitrogen atmosphere, and the mixture was refluxed for 1.5 hours. The temperature was cooled to room temperature, potassium carbonate (8.57 g, 62.0 mmol) was added to the reaction mixture, the whole was stirred for 10 minutes, and then the resulting solid was filtered out and washed with toluene and 2-propanol successively. The filtrate was concentrated under reduced pressure, the residue was purified by basic silica gel column chromatography, and the resulting solid was filtered off with diisopropyl ether to give the target compound (1.63 g, 77%) as a pale yellow solid.

IR (KBr): 3320, 3240, 3028, 2930, 1615 $cm^{-1}$ mp: 114.0-116.5° C.

Intermediate Preparation Example 15

4-(3-Aminobutyl)pyridine (Intermediate No. 15-1)

Anhydrous N,N-dimethylformamide (41 ml) was added to sodium hydride (2.81 g, 70.3 mmol) under a nitrogen atmosphere, and the mixture was stirred under ice-cold water-cooling. A solution of t-butyl acetoacetate (6.33 g, 40.0 mmol) in N,N-dimethylformamide (20 ml) was added dropwise to the mixture over 10 minutes, further after 10 minutes, 4-(chloromethyl)pyridine hydrochloride (5.00 g, 30.5 mmol) was added thereto little by little over three minutes under a nitrogen stream, and the temperature was raised to room temperature. After two hours, a saturated aqueous sodium hydrogencarbonate solution (150 ml) was added to the reaction mixture, and the whole was extracted with ethyl acetate (100 ml). The organic layer was washed with water (100 ml) and saturated brine (50 ml) successively, dried over anhydrous sodium sulfate and concentrated under reduced pressure. The residue was purified by silica gel column chromatography to give ethyl 2-acetyl-3-(4-pyridyl)propionate (1.34 g, 18%) as a pale yellow oily matter.

Next, 6 N hydrochloric acid (8 ml) was added to ethyl 2-acetyl-3-(4-pyridyl)propionate (1.20 g, 4.81 mmol), and the mixture was refluxed for 1.5 hours. The reaction mixture was concentrated under reduced pressure, 2-propanol (10 ml) was added to the concentrate, and the whole was concentrated under reduced pressure again. Ethyl acetate was added to the resulting solid, and the solid was filtered off to give 4-(4-pyridyl)-2-butanone (0.79 g, 89%) as a pale yellow solid.

Next, water (12 ml) and tetrahydrofuran (1.2 ml) were added to 4-(4-pyridyl)-2-butanone (736 mg, 3.96 mmol), and the mixture was stirred at room temperature. Sodium carbonate (483 mg, 4.56 mmol) and hydroxylamine hydrochloride (358 mg, 5.15 mmol) were added to the mixture, the whole was stirred for 1.5 hours, and then ethyl acetate (50 ml) was added to the reaction mixture to dilute it. Sodium hydrogencarbonate was added thereto. After separation, the organic layer was washed with saturated brine (10 ml), dried over anhydrous sodium sulfate and concentrated under reduced pressure. Cyclohexane was added to the resulting crystals, and the crystals were filtered off to give 4-(4-pyridyl)-2-butanone oxime (584 mg, 90%) as pale yellow crystals.

Next, anhydrous ether (19 ml) was added to lithium aluminum hydride (257 mg, 6.77 mmol) under a nitrogen atmosphere, and the mixture was stirred under ice-cooling. A solution of 4-(4-pyridyl)-2-butanone oxime (556 mg, 3.38 mmol) in ether (15 ml) was added dropwise to the mixture over seven minutes, and the whole was stirred at room temperature overnight. Further, the mixture was refluxed for two days and then stirred under ice-cooling. Ethyl acetate was slowly added to the reaction mixture, and then a 1 N aqueous sodium hydroxide solution (slowly at first, total: 20 ml) was added thereto. Chloroform (80 ml) was added thereto, and the resulting insoluble matter was filtered out with Celite. After separation, chloroform in the organic layer was evaporated under reduced pressure. The residue was combined with the aqueous layer, tetrahydrofuran (20 ml) was added thereto, and the whole was stirred at room temperature. Di-t-butyl carbonate (1.48 g, 6.78 mmol) was added thereto. The whole was stirred overnight and extracted with chloroform (50 ml). The organic layer was dried over anhydrous magnesium sulfate and concentrated under reduced pressure. The residue was purified by silica gel column chromatography. A 4 N solution of hydrogen chloride in ethyl acetate (3 ml) and ethanol (1 ml) were added to the residue, and the whole was stirred at room temperature. After three hours, the reaction mixture was concentrated under reduced pressure, chloroform (5 ml), methanol (5 ml) and triethylamine (1 ml) were added to the residue, the whole was concentrated under reduced pressure, and the residue was purified by basic silica gel column chromatography to give the target compound (161 mg, 32%) as a brown oily matter.

IR (neat): 3354, 3280, 2958, 2925, 2866, 1602 cm$^{-1}$

The following compounds were obtained in a manner similar to Intermediate Preparation Example 15.

1,2-Dimethyl-3-(4-pyridyl)propylamine (Intermediate No. 15-2)

IR (neat): 3360, 3287, 2963, 2930, 2876, 1602 cm$^{-1}$

1-Ethyl-3-(4-pyridyl)propylamine (Intermediate No. 15-3)

IR (neat): 3357, 2963, 2934, 2875, 1605 cm$^{-1}$

Intermediate Preparation Example 16

2,2-Dimethyl-3-(4-pyridyl)propylamine (Intermediate No. 16-1)

A solution of diisopropylamine (10.0 ml, 71.5 mmol) in tetrahydrofuran (150 ml) was cooled to −78° C. under a nitrogen atmosphere, and a solution of butyllithium in hexane (1.6 N) was added dropwise thereto over 10 minutes. The mixture was cooled with ice-cold water for 20 minutes and then cooled to −78° C. again, and isobutylonitrile (3.03 ml, 33.3 mmol) was added dropwise to the mixture over five minutes. Further, 4-pyridinecarboxyaldehyde (3.18 ml, 33.3 mmol) was added dropwise thereto over five minutes, and the whole was stirred for one hour and 20 minutes. Water (100 ml) was added thereto, and the reaction mixture was introduced into a continuous extraction apparatus for three days and extracted with ethyl acetate (200 ml). The obtained organic layer was dried over anhydrous magnesium sulfate and concentrated under reduced pressure, and the obtained solid was filtered off with diethyl ether to give 3-hydroxy-2,2-dimethyl-3-(4-pyridyl)propionitrile (4.20 g, 71.6%) as a colorless solid.

Triethylamine (1.57 ml, 11.3 mmol) was added to a solution of 3-hydroxy-2,2-dimethyl-3-(4-pyridyl)propionitrile (1.00 g, 5.67 mmol) in dichloromethane (20 ml) at room temperature. Further, p-toluenesulfonyl (1.30 g, 6.80 mmol) was added to the mixture, and the whole was heated with stirring at 50° C. for three days. The reaction mixture was allowed to stand and then concentrated under reduced pressure, and the concentrate was purified by silica gel column chromatography to give 2,2-dimethyl-3-(4-pyridyl)-3-(p-tolylsulfonyloxy)propionitrile (699 mg, 37.4%) as a pale yellow solid.

Lithium aluminum hydride (345 mg, 9.10 mmol) was put under a nitrogen atmosphere, and anhydrous diethyl ether (10 ml) was added dropwise thereto under ice-cold water-cooling. Next, a solution of 2,2-dimethyl-3-(4-pyridyl)-3-(p-tolylsulfonyloxy)propionitrile (600 mg, 1.82 mmol) in tetrahydrofuran (10 ml) was added dropwise to the mixture. The whole was stirred at room temperature overnight, and water (324 μl), a 15% aqueous sodium hydroxide solution (324 μl) and water (972 μl) were added successively to the reaction mixture under ice-cold water-cooling while stirring it vigorously. The organic layer was dried over anhydrous magnesium sulfate and concentrated under reduced pressure, and the obtained concentrate was purified by silica gel column chromatography to give the target compound (83.0 mg, 0.505 mmol, 28%) as a pale yellow oily matter.

IR (neat): 3290, 3074, 2960, 1652, 1602, 1417 cm$^{-1}$

Intermediate Preparation Example 17

(RS)-2-Methyl-3-(4-pyridyl)propanol (Intermediate No. 17-1)

2-Methyl-3-(4-pyridyl)propionic acid (136 g, 0.676 mol) obtained by the synthetic process in Intermediate Preparation Example 11 was dissolved in tetrahydrofuran (1,500 ml), and sodium borohydride (56.2 g, 1.49 mol) was added to the solution under ice-cold water-cooling. After 30 minutes, a solution of iodine (85.8 g, 0.338 mol) in tetrahydrofuran (500 ml) was added dropwise to the mixture under ice-cold water-cooling, and the temperature was raised to room temperature. After two hours, the reaction mixture was cooled with ice-cold water, and a saturated aqueous sodium hydrogencarbonate solution (100 ml) was added dropwise to the reaction mixture. A saturated aqueous sodium chloride solution (900 ml) and water (400 ml) were added thereto, and the whole was extracted with chloroform (1 L×2). The organic layer was washed with a 0.01% aqueous sodium thiosulfate (1 L) and a saturated aqueous sodium chloride solution (500 ml) successively, dried over anhydrous magnesium sulfate and concentrated under reduced pressure to give the target compound (127.1 g, quantitatively) as a yellow oily matter.

IR (neat): 3292, 2928, 1606, 1558, 1419 cm$^{-1}$

Intermediate Preparation Example 18

3-(t-Butyldiphenylsilyloxy)-3-(4-pyridyl)propylamine (Intermediate No. 18-1)

Diisopropylamine (1.98 g, 19.6 mmol) was added dropwise to a solution of butyllithium/hexane (10.5 ml, 16.8 mmol) in anhydrous tetrahydrofuran (20 ml) at −80° C. over five minutes, the temperature was raised to 0° C., and the mixture was stirred for 30 minutes. The mixture was cooled to −80° C., then acetonitrile (573 mg, 14.0 mmol) was added dropwise to the mixture over seven minutes, and further after 20 minutes, 4-pyridinecarboxyaldehyde (758 mg, 7.08 mmol) was added dropwise thereto over 10 minutes. After 50 minutes, a saturated aqueous ammonium chloride solution (20 ml) was added to the reaction mixture, and the temperature was raised to room temperature. The whole was continuously extracted (ethyl acetate and water) for four days. The organic layer was dried over anhydrous magnesium sulfate, the solvent was evaporated under reduced pressure, and the residue was purified by silica gel column chromatography to give 3-hydroxy-3-(4-pyridyl)propionitrile (666 mg, colorless crystals, 63.5%).

Next, imidazole (4.60 g, 67.5 mmol) and N,N-dimethylformamide (30 ml) were added to the obtained 3-hydroxy-3-(4-pyridyl)propionitrile (1.00 g, 6.75 mmol), and the mixture was stirred at room temperature. t-Butyldiphenylchlorosilane (2.23 g, 8.10 mmol) was added to the mixture, and the whole was stirred for one day and then stirred further at an external temperature of 50° C. for three hours. Ethyl acetate (50 ml) and ether (50 ml) were added thereto, and the whole was washed with water (20 ml) three times and saturated brine (30 ml) successively. The organic layer was dried over anhydrous magnesium sulfate and concentrated under reduced pressure. The residue was purified by silica gel column chromatography to give 3-(t-butyldiphenylsiloxy)-3-(4-pyridyl)propionitrile (2.58 g, 98.9%) as a colorless oily matter.

Lithium aluminum hydride (299 mg, 7.87 mmol) was suspended in anhydrous diethyl ether (10 ml) under a nitrogen atmosphere, a solution of the obtained 3-(t-butyldiphenylsiloxy)-3-(4-pyridyl)propionitrile (1.00 g, 2.59 mmol) in anhydrous diethyl ether (15 ml) was added dropwise to the suspension under ice-cooling with stirring over eight minutes, and the mixture was stirred at room temperature for 75 minutes. Ethyl acetate (15 ml) was added to the reaction mixture under ice-cooling, water (0.28 ml), a 15% aqueous sodium hydroxide solution (0.28 ml) and water (0.85 ml) were added thereto successively, and the whole was stirred at room temperature for 10 minutes. The reaction mixture was dried over anhydrous magnesium sulfate, the solvent was evaporated under reduced pressure, and the residue was purified by silica gel column chromatography to give the target compound (180.0 mg, yellow oily matter, 17.8%).

IR (neat): 3286, 3071, 2932, 2858, 1601, 1428 cm$^{-1}$

The following compound was obtained in a manner similar to Intermediate Preparation Example 18.

3-(t-Butyldimethylsilyloxy)-3-(4-pyridyl)propylamine (Intermediate No. 18-2)

Intermediate Preparation Example 19

N-[2-(1-Adamantyl)ethyl]-2-butynylamine (Intermediate No. 19-1)

Dimethyl sulfoxide (60 ml) and triethylamine (8.4 ml, 60 mmol) were added to 2-butyn-1-ol (3.0 ml, 40 mmol), and the mixture was stirred under ice-cold water-cooling. A sulfur trioxide-pyridine complex (4.2 g, 26 mmol) was added to the mixture, after 15 minutes, the sulfur trioxide-pyridine complex (5.1 g, 32 mmol) was further added thereto, and the whole was stirred for 1.5 hours. Water (40 ml) was added to the reaction mixture, the whole was extracted with methylene chloride (40 ml) twice, and the organic layer was washed with 1 N hydrochloric acid (30 ml) twice and water (40 ml) twice successively and dried over anhydrous magnesium sulfate. The solvent was evaporated under reduced pressure to give 2-butynal (1.0 g, 37%) as a brown oily matter.

Next, 2-(1-adamantyl)ethylamine hydrochloride (2.0 g, 9.3 mmol) was distributed between chloroform (30 ml) and a 1 N aqueous sodium hydroxide solution (40 ml), and the organic layer was dried over anhydrous magnesium sulfate and concentrated under reduced pressure. Methanol (15 ml) and triethylamine (2.6 ml, 19 mmol) were added to the obtained 2-(1-adamantyl)ethylamine, and the mixture was stirred at room temperature. Then a solution of 2-butynal (0.80 g, 12 mmol) obtained by the previous reaction in methanol (10 ml) was added to the mixture, and after three hours, sodium borohydride (1.9 g, 50 mmol) was added thereto under ice-cold water-cooling. After one hour, water (40 ml) was added thereto, and the whole was extracted with chloroform (60 ml). The organic layer was washed with saturated brine (40 ml), dried over anhydrous magnesium sulfate and concentrated under reduced pressure. The residue was purified by silica gel column chromatography to give the target compound (0.48 g, 22%) as a brown oily matter.

IR (neat): 3302, 2902, 2846, 2279, 2244 cm$^{-1}$

[B] PREPARATION EXAMPLES TO THE PRESENT COMPOUNDS

Present Compound Preparation Example 1

1-[2-(1-Adamantyl)ethyl]-1-pentyl-3-[3-(4-pyridyl)propyl]urea (Compound No. 1-1)

1,1'-Carbonyldiimidazole (427 mg, 2.63 mmol) was added to a solution of 4-(3-aminopropyl)pyridine (Intermediate No. 2-1, 285 mg, 2.09 mmol) in tetrahydrofuran (10 ml), and the mixture was stirred at room temperature for 20 minutes. 2-(1-Adamantyl)-N-pentylethylamine hydrochloride (Intermediate No. 1-1, 571 mg, 2.00 mmol) was added to the mixture, and the whole was refluxed for one hour. The reaction mixture was diluted with ethyl acetate (50 ml), the whole was washed with a saturated aqueous sodium hydrogencarbonate solution (50 ml) and a saturated aqueous sodium chloride solution (50 ml) successively, and the organic layer was dried over magnesium sulfate. The solvent was evaporated under reduced pressure, and the precipitated solid was washed with diisopropyl ether and filtered off to give the target compound (606 mg, 73%).

IR (KBr): 2900, 2845, 1618, 1534 cm$^{-1}$
mp: 124.0-124.7° C.

The following compounds were obtained in a manner similar to Present Compound Preparation Example 1.

1-[2-(1-Adamantyl)ethyl]-1-pentyl-3-[3-(4-pyridyl)-2-propenyl]urea (Compound No. 1-2)

IR (neat): 3339, 2902, 2846, 1626, 1530 cm$^{-1}$

N-[3-(4-Pyridyl)propyl]-1-piperidinecarboxamide (Compound No. 1-3)

IR (neat): 3339, 2934, 2854, 1621, 1538 cm$^{-1}$

N-[3-(4-Pyridyl)propyl]-1,2,3,6-tetrahydropyridine-1-carboxamide (Compound No. 1-4)

IR (neat): 3337, 2922, 2858, 1624, 1537, 1414 cm$^{-1}$

N-[3-(4-Pyridyl)propyl]-1,2,3,4-tetrahydroisoquinoline-2-carboxamide (Compound No. 1-5)

IR (KBr): 3342, 2925, 1614, 1543, 1489 cm$^{-1}$
mp: 76.0-79.0° C.

N-[3-(4-Pyridyl)propyl]-4-morpholinecarboxamide (Compound No. 1-6)

IR (KBr): 3347, 2968, 1626, 1546, 1115 cm$^{-1}$
mp: 94.0-98.0° C.

N-[3-(4-Pyridyl)propyl]-1-homopiperidinecarboxamide (Compound No. 1-7)

IR (neat): 3343, 2927, 1625, 1537 cm$^{-1}$ 1,1-Diallyl-3-[3-(4-pyridyl)propyl]urea (Compound No. 1-8)

IR (neat): 3350, 2928, 1628, 1603, 1535 cm$^{-1}$

N-[3-(4-Pyridyl)propyl]-2-decahydroisoquinolinecarboxamide (Compound No. 1-9)

IR (neat): 3343, 2855, 2622, 1621, 1539 cm$^{-1}$ 1,1-Dibutyl-3-[3-(4-pyridyl)propyl]urea (Compound No. 1-10)

IR (neat): 3347, 2957, 2872, 1626, 1537 cm$^{-1}$ 1,1-Dihexyl-3-[3-(4-pyridyl)propyl]urea (Compound No. 1-11)

IR (neat): 3348, 2928, 2857, 1626, 1532 cm$^{-1}$ 1,1-Diisopentyl-3-[3-(4-pyridyl)propyl]urea (Compound No. 1-12)

IR (neat): 3344, 2955, 2869, 1626, 1533 cm$^{-1}$ 1,1-Didecyl-3-[3-(4-pyridyl)propyl]urea (Compound No. 1-13)

IR (neat): 3346, 2925, 2854, 1626, 1537 cm$^{-1}$

1-[2-(1-Adamantyl)ethyl]-1-[2-(N-benzyloxycarbonyl-N-methylamino)ethyl]-3-[3-(4-pyridyl)propyl]urea (Compound No. 1-14)

IR (neat): 3360, 2902, 2846, 1772, 1699, 1634, 1532 cm$^{-1}$

1-[2-(1-Adamantyl)ethyl]-1-[2-(dimethylamino)ethyl]-3-[3-(4-pyridyl)propyl]urea (Compound No. 1-15)

IR (KBr): 3322, 2900, 2845, 1621, 1526 cm$^{-1}$
mp: 104.0-106.5° C.

1-[2-(1-Adamantyl)ethyl]-1-propyl-3-[3-(4-pyridyl)propyl]urea (Compound No. 1-16)

IR (KBr): 3331, 2901, 2846, 1622, 1602, 1534 cm$^{-1}$
mp: 99.0-103.0° C.

1-[2-(1-Adamantyl)ethyl]-1-(2-propynyl)-3-[3-(4-pridyl)propyl]urea (Compound No. 1-17)

IR (KBr): 3322, 3204, 2899, 2845, 2112, 1626, 1605, 1543, 1444 cm$^{-1}$
mp: 152.0-154.0° C.

1-[2-(1-Adamantyl)ethyl]-1-(2-methoxyethyl)-3-[3-(4-pyridyl)propyl]urea (Compound No. 1-18)

IR (KBr): 3321, 2900, 2846, 1625, 1602, 1534, 1451 cm$^{-1}$
mp: 101.5-104.5° C.

1-[2-(1-Adamantyl)ethyl]-1-cyclopropyl-3-[3-(4-pyridyl)propyl]urea (Compound No. 1-19)

IR (KBr): 3365, 2900, 1633 cm$^{-1}$
mp: 108.0-115.5° C.

1-[2-(1-Adamantyl)ethyl]-1-cyanomethyl-3-[3-(4-pyridyl)propyl]urea (Compound No. 1-20)

IR (neat): 3350, 2903, 2247, 1644 cm$^{-1}$

1-[2-(1-Adamantyl)ethyl]-1-cyclopentylmethyl-3-[3-(4-pyridyl)propyl]urea (Compound No. 1-21)

IR (KBr): 3328, 2906, 2845, 1615, 1450 cm$^{-1}$
mp: 155.0-158.0° C.

1-[2-(1-Adamantyl)ethyl]-1-cyclopropylmethyl-3-[3-(4-pyridyl)propyl]urea (Compound No. 1-22)

IR (KBr): 3328, 2900, 2845, 1618, 1534 cm$^{-1}$
mp: 123.0-125.0° C.

1-[2-(1-Adamantyl)ethyl]-1-allyl-3-[3-(4-pyridyl)propyl]urea (Compound No. 1-23)

IR (KBr): 3329, 2900, 1625, 1538 cm$^{-1}$
mp: 99.0-102.0° C.

1-[2-(1-Adamantyl)ethyl]-3-[3-(4-pyridyl)propyl]-1-(3,3,3-trifluoropropyl)urea (Compound No. 1-24)

IR (KBr): 3310, 2900, 2847, 1622, 1543 cm$^{-1}$
mp: 107.5-109.0° C.

1-[2-(1-Adamantyl)ethyl]-1-(2-butenyl)-3-[3-(4-pyridyl)propyl]urea (Compound No. 1-25)

IR (KBr): 3328, 2900, 1619 cm$^{-1}$
mp: 89.5-93.5° C.

1-[2-(1-Adamantyl)ethyl]-[2-[N-(t-butoxycarbonyl)-N-methylamino]ethyl]-3-[3-(4-pyridyl)propyl]urea (Compound No. 1-26)

IR (neat): 3350, 2903, 2846, 1694, 1633, 1537 cm$^{-1}$

1-[2-(1-Adamantyl)ethyl]-3-[3-(4-pyridyl)propyl]-1-(2-thienyl)methylurea (Compound No. 1-27)

IR (KBr): 3328, 2900, 2845, 1626, 1544 cm$^{-1}$
mp: 142.5-144.5° C.

1-[2-(1-Adamantyl)ethyl]-1-benzyloxy-3-[3-(4-pyridyl)propyl]urea (Compound No. 1-28)

IR (neat): 3444, 3350, 2902, 2846, 1666, 1517 cm$^{-1}$

1-[2-(1-Adamantyl)ethyl]-1-hexyl-3-[3-(4-pyridyl)propyl]urea (Compound No. 1-29)

IR (KBr): 3354, 2901, 2845, 1619, 1538 cm$^{-1}$
mp: 119.5-121.5° C.

1-(1-Adamantyl)methyl-1-propyl-3-[3-(4-pyridyl)propyl]urea (Compound No. 1-30)

IR (neat): 3350, 2902, 1626 cm$^{-1}$

1-[2-(1-Adamantyl)ethyl]-1-(3-methyl-2-butenyl)-3-[3-(4-pyridyl)propyl]urea (Compound No. 1-31)

IR (KBr): 3358, 2900, 2845, 1622, 1526 cm$^{-1}$
mp: 93.0-96.0° C.

1-[2-(1-Adamantyl)ethyl]-1-decyl-3-[3-(4-pyridyl)propyl]urea (Compound No. 1-32)

IR (KBr): 3340, 2924, 2846, 1626, 1602, 1534 cm$^{-1}$
mp: 75.0-76.0° C.

1-[2-(1-Adamantyl)ethyl]-1-(2-methyl-2-propenyl)-3-[3-(4-pyridyl)propyl]urea (Compound No. 1-33)

IR (KBr): 3336, 2905, 2846, 1624, 1544 cm$^{-1}$
mp: 108.0-109.0° C.

1-[2-(1-Adamantyl)ethyl]-1-cinnamyl-3-[3-(4-pyridyl)propyl]urea (Compound No. 1-34)

IR (KBr): 3374, 2899, 2844, 1619, 1534 cm$^{-1}$
mp: 130.0-134.5° C.

1-[3-(1-Adamantyl)propyl]-1-propyl-3-[3-(4-pyridyl)propyl]urea (Compound No. 1-35)

IR (neat): 3349, 2901, 1626, 1536 cm$^{-1}$ 1-(1-Adamantyl)methyl-1-pentyl-3-[3-(4-pyridyl)propyl]urea (Compound No. 1-36)

IR (neat): 3349, 2903, 1625, 1531 cm$^{-1}$

1-[2-(1-Adamantyl)ethyl]-1-(2-methylthiazol-4-yl)methyl-3-[3-(4-pyridyl)propyl]urea (Compound No. 1-37)

IR (neat): 3337, 2901, 1632, 1536 cm$^{-1}$ 01,1-Dipentyl-3-[3-(4-pyridyl)propyl]urea (Compound No. 1-38)

IR (neat): 3347, 2929, 2859, 1626, 1537 cm$^{-1}$

1-Pentyl-1-(2-piperidinoethyl)-3-[3-(4-pyridyl)propyl]urea (Compound No. 1-39)

IR (neat): 3350, 2933, 2856, 1640, 1533 cm$^{-1}$

1-[2-(1-Adamantyl)ethyl]-1-methyl-3-[3-(4-pyridyl)propyl)urea (Compound No. 1-40)

IR (KBr): 3334, 2901, 2846, 1626, 1604, 1534 cm$^{-1}$
mp: 99.0-109.0° C.

1-[2-(1-Adamantyl)ethyl]-1-ethyl-3-[3-(4-pyridyl)propyl]urea (Compound No. 1-41)

IR (KBr): 3324, 2901, 2845, 1622, 1540 cm$^{-1}$
mp: 106.0-115.0° C.

1-[2-(1-Adamantyl)ethyl]-1-furfuryl-3-[3-(4-pyridyl)propyl]urea (Compound No. 1-42)

IR (KBr): 3331, 2900, 2846, 1618, 1538 cm$^{-1}$
mp: 128.0-130.0° C.

1-[2-(1-Adamantyl)ethyl]-1-benzyl-3-[3-(4-pyridyl)propyl]urea (Compound No. 1-43)

IR (KBr): 3335, 2901, 2847, 1619, 1538 cm$^{-1}$
mp: 130.5-135.0° C.

1-(2-Cyclohexylethyl)-1-pentyl-3-[3-(4-pyridyl)propyl]urea (Compound No. 1-44)

IR (neat): 3345, 2923, 1625, 1603, 1531 cm$^{-1}$

1-Pentyl-1-phenethyl-3-[3-(4-pyridyl)propyl]urea (Compound No. 1-45)

IR (neat): 3345, 3063, 2929, 1625, 1533 cm$^{-1}$

1-Butyl-1-(2-cyclohexylethyl)-3-(4-pyridyl)methylurea (Compound No. 1-46)

IR (neat): 3342, 2922, 2851, 1629, 1602, 1563, 1530, 1448 cm$^{-1}$ 1-(2-Cyclohexylethyl)-1,3-bis[(4-pyridyl)methyl]urea (Compound No. 1-47)

IR (neat): 3337, 3029, 2922, 2850, 1633, 1602, 1534, 1445 cm$^{-1}$ 1-(2-Cyclohexylethyl)-3-(4-pyridyl)methyl-1-(2-thienyl)methylurea (Compound No. 1-48)

IR (neat): 3342, 2921, 2850, 1631, 1602, 1562, 1536, 1415, 1267, 1227 cm$^{-1}$

1-[2-(t-Butoxycarbonyl)ethyl]-1-(2-cyclohexylethyl)-3-(4-pyridyl)methylurea (Compound No. 1-49)

IR (neat): 3347, 2977, 2923, 2851, 1727, 1633, 1602, 1563, 1531, 1449 cm$^{-1}$ 1-(2-Cyclohexylethyl)-1-[2-(methoxycarbonyl)ethyl]-3-(4-pyridyl)methylurea (Compound No. 1-50)

IR (neat): 3348, 2923, 2850, 1737, 1633, 1603, 1563, 1532, 1437 cm$^{-1}$ 1-(2-Carbamoylethyl)-1-(2-cyclohexylethyl)-3-(4-pyridyl)methylurea (Compound No. 1-51)

IR (neat): 3324, 2922, 2850, 1673, 1632, 1606, 1563, 1530, 1448 cm$^{-1}$ 1-(2-Cyclohexylethyl)-1-pentyl-3-(4-pyridyl)methylurea (Compound No. 1-52)

IR (KBr): 3313, 2925, 1627, 1602, 1527, 1410 cm$^{-1}$
mp: 64.7-65.8° C.

1-(2-Cyclohexylethyl)-1-(2-dimethylaminoethyl)-3-(4-pyridyl)methylurea (Compound No. 1-53)

IR (KBr): 3346, 2922, 2850, 2778, 1635, 1562, 1533, 1448 cm$^{-1}$

1-[2-[N-(t-Butoxycarbonyl)-N-methylamino]ethyl]-(2-cyclohexylethyl)-3-(4-pyridyl)methylurea (Compound No. 1-54)

IR (neat): 3338, 2976, 2924, 2851, 1694, 1633, 1602, 1563, 1531, 1484, 1450 cm$^{-1}$ 1-Pentyl-1-[2-(2-pyridyl)ethyl]-3-[3-(4-pyridyl)propyl]urea (Compound No. 1-55)

IR (neat): 3350, 2929, 2859, 1633, 1602, 1537 cm$^{-1}$ 1,1-Bis[2-(1-adamantyl)ethyl]-3-[3-(4-pyridyl)propyl]urea (Compound No. 1-56)

IR (neat): 3358, 2901, 2845, 1625, 1530 cm$^{-1}$
mp: 80° C.

1-[2-(1-Adamantyl)ethyl]-1-butyl-3-[3-(4-pyridyl)propyl]urea (Compound No. 1-57)

IR (KBr): 3315, 2901, 1618, 1534 cm$^{-1}$
mp: 109.5-118.0° C.

1,1-Bis(2-hydroxypropyl)-3-[3-(4-pyridyl)propyl]urea hydrochloride (Compound No. 1-58)

IR (neat): 3350, 1688, 1638, 1538 cm$^{-1}$

1-[Bis(t-butoxycarbonylaminomethyl)]methyl-1-isopentyl-3-[3-(4-pyridyl)propyl]urea (Compound No. 1-59)

IR (neat): 3326, 2960, 1698, 1631, 1525 cm$^{-1}$

1-Cyclohexyl(phenyl)methyl-1-(3-phenylpropyl)-3-[3-(4-pyridyl)propyl]urea (Compound No. 1-60)

IR (KBr): 3352, 2931, 1619, 1522 cm$^{-1}$
mp: 107.0-112.0° C.

1,1-Dicyclohexyl-3-[3-(4-pyridyl)propyl]urea (Compound No. 1-61)

IR (KBr): 3304, 2930, 2848, 1638, 1602, 1533 cm$^{-1}$
mp: 143.0-145.5° C.

1-[2-[N-(t-Butoxycarbonyl)-N-methylamino]ethyl]-1-phenethyl-3-[3-(4-pyridyl)propyl]urea (Compound No. 1-62)

IR (neat): 3350, 1694, 1633, 1532, 1166 cm$^{-1}$

1-[2-[N-(t-Butoxycarbonyl)-N-methylamino]ethyl]-1-pentyl-3-[3-(4-pyridyl)propyl]urea (Compound No. 1-63)

IR (neat): 3350, 1694, 1632, 1537, 1167 cm$^{-1}$

1-[2-(N-Benzyloxycarbonyl-N-methylamino)ethyl]-1-phenethyl-3-[3-(4-pyridyl)propyl]urea (Compound No. 1-64)

IR (neat): 3350, 1698, 1632, 1531 cm$^{-1}$

1-[3-(1-Adamantyl)propyl]-1-pentyl-3-[3-(4-pyridyl)propyl]urea (Compound No. 1-65)

IR (KBr): 3333, 2901, 2844, 1623, 1602, 1543 cm$^{-1}$

1-[2-(1-Adamantyl)ethyl]-3-pentyl-1-[3-(4-pyridyl)propyl]urea (Compound No. 1-66)

IR (KBr): 3370, 3322, 2903, 2846, 1618, 1534 cm$^{-1}$
mp: 47.0-50.0° C.

3-[2-(1-Adamantyl)ethyl]-1-[2-(t-butoxycarbonyl)ethyl]-1-[3-(4-pyridyl)propyl]urea (Compound No. 1-67)

IR (neat): 3348, 2902, 2846, 1726, 1627, 1538, 1367, 1152 cm$^{-1}$

1-[2-(1-Adamantyl)ethyl]-1-isopropyl-3-[3-(4-pyridyl)propyl]urea (Compound No. 1-68)

IR (KBr): 3330, 2903, 2845, 1614, 1533 cm$^{-1}$
mp: 132.0-134.0° C.

1-[2-(1-Adamantyl)ethyl]-1-[2-(t-butoxycarbonyl)ethyl]-3-[3-(4-pyridyl)propyl]urea (Compound No. 1-69)

IR (KBr): 3356, 2903, 1720, 1622, 1538, 1156 cm$^{-1}$
mp: 124.5-127.0° C.

1-[2-(1-Adamantyl)ethyl]-1-cyclopentyl-3-[3-(4-pyridyl)propyl]urea (Compound No. 1-70)

IR (KBr): 3297, 2906, 2844, 1618, 1544 cm$^{-1}$
mp: 135.5-137.5° C.

1-[2-(1-Adamantyl)ethyl]-1-(t-butoxycarbonylamino)-3-[3-(4-pyridyl)propyl]urea (Compound No. 1-71)

IR (neat): 3231, 2903, 1732, 1650 cm$^{-1}$

1-[2-(1-Adamantyl)ethyl]-1-pentyl-3-(2-pyridyl)methylurea (Compound No. 1-72)

IR (KBr): 3333, 2900, 2844, 1625, 1535 cm$^{-1}$
mp: 87.5-92.0° C.

1-[2-(1-Adamantyl)ethyl]-1-pentyl-3-(3-pyridyl)methylurea (Compound No. 1-73)

IR (KBr): 3328, 2901, 2846, 1622, 1530 cm$^{-1}$
mp: 88.5-101.5° C.

1-[2-(1-Adamantyl)ethyl]-1-pentyl-3-(4-pyridyl)methylurea (Compound No. 1-74)

IR (KBr): 3331, 2900, 2845, 1626, 1538 cm$^{-1}$
mp: 96.5-108.0° C.

1-[2-(1-Adamantyl)ethyl]-1-pentyl-3-[2-(2-pyridyl)ethyl]urea (Compound No. 1-75)

IR (KBr): 3346, 2904, 2845, 1622, 1539 cm$^{-1}$
mp: 80.0-100.0° C.

1-[2-(1-Adamantyl)ethyl]-1-pentyl-3-[2-(3-pyridyl)ethyl]urea (Compound No. 1-76)

IR (KBr): 3334, 2900, 2845, 1618, 1541 cm$^{-1}$
mp: 112.5-114.5° C.

1-(2-Cyclohexylethyl)-1-(2-methoxyethyl)-3-(4-pyridyl)methylurea (Compound No. 1-77)

IR (neat): 3350, 2922, 2850, 1633, 1603, 1534 cm$^{-1}$

1-[2-(N-Benzyloxycarbonyl-N-methylamino)ethyl]-1-pentyl-3-[3-(4-pyridyl)propyl]urea (Compound No. 1-78)

IR (neat): 3358, 2930, 1701, 1633, 1534 cm$^{-1}$
1-Ethyl-3-[3-(4-pyridyl)propyl]-1-(3,4,5-trimethoxyphenethyl)urea (Compound No. 1-79)
IR (neat): 3350, 2936, 1626, 1590, 1530, 1239 cm$^{-1}$ 1-[2-(1-Adamantyl)ethyl]-1-pentyl-3-[2-(4-pyridyl)ethyl]urea (Compound No. 1-80)

IR (KBr): 3346, 2901, 2844, 1622, 1538 cm$^{-1}$
mp: 107-118° C.

1-[2-(1H-5-Imidazolyl)ethyl]-1-isopentyl-3-[3-(4-pyridyl)propyl]urea (Compound No. 1-81)

IR (neat): 3117, 2954, 1606, 1537 cm$^{-1}$

1-Cyclohexyl-1-(3,4-dimethoxyphenethyl)-3-[3-(4-pyridyl)propyl]urea (Compound No. 1-82)

IR (neat): 3353, 2931, 1621, 1515, 1236, 1029 cm$^{-1}$

1-[2-(1-Adamantyl)ethyl]-1-pentyl-3-[3-(2-pyridyl)propyl]urea (Compound No. 1-83)

IR (KBr): 3324, 2900, 2845, 1622, 1538 cm$^{-1}$
mp: 84.4-85.7° C.

1-[2-(1-Adamantyl)ethyl]-1-pentyl-3-[3-(3-pyridyl)propyl]urea (Compound No. 1-84)

IR (KBr): 3355, 2902, 2845, 1615, 1526 cm$^{-1}$
mp: 99.9-105.2° C.

1-Cyclopropyl-3-[3-(4-pyridyl)propyl]-1-(3,4,5-trimethoxyphenethyl)urea (Compound No. 1-85)

IR (neat): 3400, 2938, 1644, 1590, 1510, 1239, 1128 cm$^{-1}$

1-[2-(1-Adamantyl)ethyl]-3-(4-dimethylamino)phenethyl-1-pentylurea (Compound No. 1-86)

IR (KBr): 3341, 2900, 2845, 1619, 1526 cm$^{-1}$
mp: 115.8-118.1° C.

1-[2-(1-Adamantyl)ethyl]-1-pentyl-3-[4-(4-pyridyl)butyl]urea (Compound No. 1-87)

IR (KBr): 3354, 2900, 2844, 1618, 1538 cm$^{-1}$
mp: 74.1-78.1° C.

1-[2-(1-Adamantyl)ethyl]-3-(t-butoxycarbonyl)-1-pentyl-3-[2-(4-pyridyl)oxyethyl]urea (Compound No. 1-88)

IR (neat): 2903, 2847, 1704, 1590 cm$^{-1}$

1-[2-(1-Adamantyl)ethyl]-1-[3-[N-(t-butoxycarbonyl)-N-methylamino]propyl]-3-[3-(4-pyridyl)propyl]urea (Compound No. 1-89)

IR (neat): 3350, 2903, 2847, 1694, 1632, 1531 cm$^{-1}$

1-Cyclohexyl(phenyl)methyl-1-[3-(4-methoxyphenoxy)propyl]-3-[3-(4-pyridyl)propyl]urea (Compound No. 1-90)

IR (neat): 3369, 2930, 1626, 1510, 1231 cm$^{-1}$

1-[2-(1-Adamantyl)ethyl]-1-pentyl-3-[3-(4-quinolyl)propyl]urea (Compound No. 1-91)

IR (KBr): 3354, 2902, 2845, 1622, 1534 cm$^{-1}$
mp: 80.2-102.0° C.

1-[2-(1-Adamantyl)ethyl]-1-[2-[N-(1-imidazolylcarbonyl)-N-methylamino]ethyl]-3-[3-(4-pyridyl)propyl]urea (Compound No. 1-92)

IR (neat): 3366, 2902, 2846, 1695, 1635, 1604, 1531 cm$^{-1}$

1-Diphenylmethyl-1-(3-phenylpropyl)-3-[3-(4-pyridyl)propyl]urea (Compound No. 1-93)

IR (KBr): 3334, 3026, 2927, 1621, 1522 cm$^{-1}$
mp: 123.0-124.8° C.

1,1-Di-(5-hexenyl)-3-[3-(4-pyridyl)propyl]urea (Compound No. 1-94)

IR (neat): 3350, 3074, 2930, 2859, 1621, 1538 cm$^{-1}$ 1,1-Di-(7-octenyl)-3-[3-(4-pyridyl)propyl]urea (Compound No. 1-95)

IR (neat): 3349, 3074, 2927, 2856, 1625, 1537 cm$^{-1}$

4-[2-[3-[2-(1-Adamantyl)ethyl]-3-pentyl]ureidoethyl]benzene sulfonamide (Compound No. 1-96)

IR (KBr): 3423, 2906, 2847, 1598, 1540, 1161 cm$^{-1}$
mp: 85.0-120.7° C.

1-[2-(1-Adamantyl)ethyl]-3-(1-imidazolyl)propyl-1-pentylurea (Compound No. 1-97)

IR (KBr): 3340, 2902, 2845, 1618, 1534 cm$^{-1}$
mp: 97.0-100.0° C.

1-[2-(1-Adamantyl)ethyl]-3-(4-hydroxyphenethyl)-1-pentylurea (Compound No. 1-98)

IR (KBr): 3392, 2902, 2845, 1614, 1535, 1515 cm$^{-1}$
mp: 96.3-99.4° C.

1-[2-(1-Adamantyl)ethyl]-1-[2-(3-t-butyl-1-methylureido)ethyl]-3-[3-(4-pyridyl)propyl]urea (Compound No. 1-99)

IR (neat): 3310, 2903, 1632, 1537 cm$^{-1}$

1-[2-(1-Adamantyl)ethyl]-3-[2-methyl-3-(4-pyridyl)propyl]-1-pentylurea (Compound No. 1-100)

IR (KBr): 3347, 2957, 2902, 2846, 1621, 1604, 1539 cm$^{-1}$
mp: 105.3-112.3° C.

1-[2-(1-Adamantyl)ethyl]-1-[2-(1-methyl-3-propylureido)ethyl]-3-[3-(4-pyridyl)propyl]urea (Compound No. 1-101)

IR (neat): 3316, 2902, 1631, 1537 cm$^{-1}$

1-Pentyl-1-(3-phenylpropyl)-3-[3-(4-pyridyl)propyl]urea (Compound No. 1-102)

IR (neat): 3348, 2929, 1625, 1537 cm$^{-1}$

1-[2-(Acetylamino)ethyl]-1-[2-(1-adamantyl)ethyl]-3-[3-(4-pyridyl)propyl]urea (Compound No. 1-103)

IR (neat): 3291, 2902, 2846, 1632, 1556, 753 cm$^{-1}$

1-[2-(1-Adamantyl)ethyl]-1-pentyl-3-[3-(4-pyridyl)butyl]urea (Compound No. 1-104)

IR (KBr): 3346, 2901, 2845, 1618, 1601, 1539 cm$^{-1}$
mp: 93.0-98.0° C.

1-[2-(1-Adamantyl)ethyl]-3-[3-(4-pyridyl)propyl]-1-(4,4,4-trifluorobutyl)urea (Compound No. 1-105)

IR (KBr): 3317, 2901, 2846, 1618, 1538, 1255, 1123 cm$^{-1}$
mp: 142.6-145.0° C.

1-[2-(1-Adamantyl)ethyl]-3-[3-(4-pyridyl)propyl]-1-(5,5,5-trifluoropentyl)urea (Compound No. 1-106)

IR (KBr): 3333, 2900, 2846, 1618, 1534, 1259, 1140 cm$^{-1}$
mp: 116.9-118.9° C.

1-[2-(1-Adamantyl)ethyl]-1-[2-[N-(t-butoxycarbonyl)-N-methylamino]ethyl-3-[2-methyl-3-(4-pyridyl)propyl]urea (Compound No. 1-107)

IR (neat): 3350, 2902, 2846, 1694, 1672, 1633, 1603, 1537 cm$^{-1}$

1-[2-(1-Adamantyl)ethyl]-1-pentyl-3-[2-(4-pyridylmethyl)butyl]urea (Compound No. 1-108)

IR (KBr): 3347, 2900, 2845, 1622, 1538 cm$^{-1}$
mp: 72.0-77.0° C.

1-[2-(1-Adamantyl)ethyl]-3-[2-benzyl-3-(4-pyridyl)propyl]-1-pentylurea (Compound No. 1-109)

IR (KBr): 3329, 2902, 2846, 1622, 1544 cm$^{-1}$
mp: 111.0-116.0° C.

1-[2-(1-Adamantyl)ethyl]-3-[2,2-bis(4-pyridylmethyl)ethyl]-1-pentylurea (Compound No. 1-110)

IR (KBr): 3330, 2905, 2845, 1619, 1602, 1534 cm$^{-1}$
mp: 124.0-136.0° C.

(Z)-1-[2-(1-Adamantyl)ethyl]-1-pentyl-3-[3-(4-pyridyl)-2-propenyl]urea (Compound No. 1-111)

IR (neat): 3338, 2901, 2846, 1625, 1596, 1530 cm$^{-1}$ (E)-1-[2-(1-Adamantyl)ethyl]-1-pentyl-3-[3-(4-pyridyl)-2-propenyl]urea (Compound No. 1-112)

IR (KBr): 3315, 2900, 2845, 1623, 1526 cm$^{-1}$
mp: 90-118° C.

1-Isopentyl-3-[3-(4-pyridyl)propyl]-1-(3,3,3-trifluoropropyl)urea (Compound No. 1-113)

IR (neat): 3342, 2956, 1628, 1604, 1539 cm$^{-1}$

1-[2-(1-Adamantyl)ethyl]-3-[3-(4-pyridyl)propyl]-1-(2,2,2-trifluoroethyl)urea (Compound No. 1-114)

IR (KBr): 3346, 2901, 2847, 1630, 1604, 1544, 1145, 1108 cm$^{-1}$
mp: 106.2-107.3° C.

3-[2-Methyl-3-(4-pyridyl)propyl]-1-pentyl-1-phenethylurea (Compound No. 1-115)

IR (KBr): 3352, 2927, 2858, 1622, 1530, 1496, 1453, 1416, 1276 cm$^{-1}$
mp: 49.0-50.0° C.

1,1-Dibutyl-3-[2-methyl-3-(4-pyridyl)propyl]urea (Compound No. 1-116)

IR (neat): 3347, 2957, 2929, 1624, 1534 cm$^{-1}$

1-[2-(1-Adamantyl)ethyl]-3-[2-methyl-3-(4-pyridyl)propyl]-1-(3,3,3-trifluoropropyl)urea (Compound No. 1-117)

IR (KBr): 3354, 2901, 2847, 1626, 1540 cm$^{-1}$
mp: 81.1-84.1° C.

1-(2-Cyclohexylethyl)-3-[2-methyl-3-(4-pyridyl)propyl]-1-pentylurea (Compound No. 1-118)

IR (neat): 3346, 2923, 2852, 1625, 1533 cm$^{-1}$ 1-(3-Cyclohexylpropyl)-1-propyl-3-[3-(4-pyridyl)propyl]urea (Compound No. 1-119)

IR (neat): 3346, 2922, 1626, 1537 cm$^{-1}$ (−)-1-[2-(1-Adamantyl)ethyl]-3-[2-methyl-3-(4-pyridyl)propyl]-1-pentylurea (Compound No. 1-120)

IR (KBr): 3337, 2900, 1616, 1526 cm$^{-1}$
mp: 103.0-104.0° C.
[α]$^{20}_D$: −4.6° (MeOH, C1.0)

(+)-1-[2-(1-Adamantyl)ethyl]-3-[2-methyl-3-(4-pyridyl)propyl]-1-pentylurea (Compound No. 1-121)

IR (KBr): 3336, 2900, 1616, 1526 cm$^{-1}$
mp: 102.9-103.5° C.
[α]$^{20}_D$: +4.2° (MeOH, C1.0)

1-[3-(1-Adamantyl)propyl]-1-butyl-3-[3-(4-pyridyl)propyl]urea (Compound No. 1-122)

IR (KBr): 3323, 2954, 2904, 2846, 1624, 1603, 1548 cm$^{-1}$
mp: 79.8-80.4° C.

1-[3-(1-Adamantyl)propyl]-3-[3-(4-pyridyl)propyl]-1-(2,2,2-trifluoroethyl)urea (Compound No. 1-123)

IR (KBr): 3355, 2902, 2848, 1627, 1605, 1545, 1145, 1112 cm$^{-1}$
mp: 88.9-90.0° C.

1-[4-(1-Adamantyl)butyl]-1-ethyl-3-[3-(4-pyridyl)propyl]urea (Compound No. 1-124)

IR (KBr): 3352, 2897, 2847, 1626, 1604, 1539 cm$^{-1}$
mp: 92.7-93.7° C.

1-[4-(1-Adamantyl)butyl]-1-propyl-3-[3-(4-pyridyl)propyl]urea (Compound No. 1-125)

IR (KBr): 3343, 2900, 2847, 1625, 1604, 1544 cm$^{-1}$
mp: 110.0-110.5° C.

1-[2-(1-Adamantyl)ethyl]-1-pentyl-3-[2-(4-pyridylamino)ethyl]urea (Compound No. 1-126)

IR (KBr): 3301, 2904, 2848, 1628, 1602, 1527 cm$^{-1}$
mp: 133.9-134.5° C.

(+)-1-[3-(1-Adamantyl)propyl]-3-[2-methyl-3-(4-pyridyl)propyl]-1-propylurea (Compound No. 1-127)

IR (neat): 3350, 2902, 2846, 1625, 1534 cm$^{-1}$
$[\alpha]^{20}_D$: +4.2° (MeOH, C0.51)

1-[3-(1-Adamantyl)propyl]-1-propyl-3-(4-pyridyl)methylurea (Compound No. 1-128)

IR (KBr): 3319, 2902, 1630, 1604, 1537 cm$^{-1}$
mp: 96.0-98.0° C.

1-[3-(1-Adamantyl)propyl]-1-propyl-3-[2-(4-pridyl)ethyl]urea (Compound No. 1-129)

IR (neat): 3345, 2901, 1634, 1538 cm$^{-1}$

1-[3-(1-Adamantyl)propyl]-1-ethyl-3-[3-(4-pyridyl)propyl]urea (Compound No. 1-130)

IR (KBr): 3345, 2969, 2905, 2845, 1622, 1605, 1535 cm$^{-1}$
mp: 97.5-98.2° C.

1-[2-(1-Adamantyloxy)ethyl]-1-propyl-3-[3-(4-pyridyl)propyl]urea (Compound No. 1-131)

IR (neat): 3344, 2911, 2853, 1642, 1603, 1534 cm$^{-1}$ 1-(1-Adamantyl)aminocarbonylmethyl-1-propyl-3-[3-(4-pyridyl)propyl]urea (Compound No. 1-132)

IR (KBr): 3335, 3261, 2910, 2853, 1662, 1622, 1543 cm$^{-1}$
mp: 132.0-132.5° C.

1-[3-(1-Adamantyl)propyl]-1-propyl-3-[4-(4-pyridyl)butyl]urea (Compound No. 1-133)

IR (neat): 3350, 2901, 1623, 1532 cm$^{-1}$

1-[3-(1-Adamantyl)propyl]-1-[2-[N-(t-butoxycarbonyl)-N-methylamino]ethyl]-3-[3-(4-pyridyl)propyl]urea (Compound No. 1-134)

IR (neat): 3347, 2902, 2846, 1696, 1632, 1603, 1534, 1167 cm$^{-1}$

1-[2-(1-Adamantyl)ethyl]-3-[2,2-dimethyl-3-(4-pyridyl)propyl]-1-pentylurea (Compound No. 1-135)

IR (KBr): 3338, 2905, 1620, 1600, 1541 cm$^{-1}$
mp: 82.5-84.9° C.

1-[3-(1-Adamantyl)propyl]-3-[3-(4-pyridyl)propyl]-1-(3,3,3-trifluoropropyl)urea (Compound No. 1-136)

IR (neat): 3349, 2902, 1628, 1538 cm$^{-1}$

1-[2-(1-Adamantyl)ethyl]-3-[1-methyl-3-(4-pyridyl)propyl]-1-pentylurea (Compound No. 1-137)

IR (KBr): 3338, 2902, 2847, 1615, 1533 cm$^{-1}$
mp: 128.5-129.0° C.

1-[2-(1-Adamantyl)ethyl]-3-[3-(t-butyldimethylsilyloxy)-3-(4-pyridyl)propyl]-1-pentylurea (Compound No. 1-138)

IR (neat): 3355, 2904, 2849, 1628, 1600, 1532, 1099 cm$^{-1}$ (+)-1-[2-(1-Adamantyl)ethyl]-1-[2-[N-(t-butoxycarbonyl)-N-methylamino]ethyl]-3-[2-methyl-3-(4-pyridyl)propyl]urea (Compound No. 1-139)

IR (KBr): 3345, 2910, 2848, 1693, 1622, 1602, 1538, 1248 cm$^{-1}$
mp: 122.7-123.7° C.
$[\alpha]^{20}_D$: +2.8° (MeOH, C1.0)

1-[2-(1-Adamantyl)aminoethyl]-1-propyl-3-[3-(4-pyridyl)propyl]urea (Compound No. 1-140)

IR (neat): 3275, 2908, 2849, 1636, 1536 cm$^{-1}$

1-[2-(1-Adamantyl)ethyl]-1-(2-butynyl)-3-[3-(4-pyridyl)propyl]urea (Compound No. 1-141)

IR (neat): 3351, 2903, 2847, 2290, 2221, 1630, 1605, 1538 cm$^{-1}$

1-[2-(1-Adamantyl)ethyl]-3-[1,2-dimethyl-3-(4-pyridyl)propyl]-1-pentylurea (Compound No. 1-142)

IR (neat): 3354, 2904, 2847, 1623, 1604, 1525 cm$^{-1}$

1-[2-(1-Adamantyl)ethyl]-3-[1-ethyl-3-(4-pyridyl)propyl]-1-pentylurea (Compound No. 1-143)

IR (neat): 3352, 2904, 2847, 1622, 1605, 1529 cm$^{-1}$

1-[2-(1-Adamantyl)ethyl]-3-[3-(t-butyldiphenylsilyloxy)-3-(4-pyridyl)propyl]-1-pentylurea (Compound No. 1-144)

IR (neat): 3360, 3072, 3050, 2903, 2849, 1634, 1602, 1532, 1428 cm$^{-1}$

Present Compound Preparation Example 2

5-(4-Pyridyl)valeric acid N-[2-(1-adamantyl)ethyl]-N-propylamide (Compound No. 2-1)

N,N-Dimethylformamide (8.4 ml) was added to a mixture of 2-(1-adamantyl)-N-propylethylamine (Intermediate No. 1-6, 0.37 g, 1.7 mmol) and 5-(4-pyridyl)valeric acid (Intermediate No. 5-1, 0.30 g, 1.7 mmol), and the whole was stirred at room temperature. N-Methylmorpholine (0.27 ml, 2.5 mmol) and 1-ethyl-3-(3-dimethylaminopropyl)carbodiimide hydrochloride (0.38 g, 2.0 mmol) were added thereto successively, and the whole was stirred overnight. The reaction mixture was concentrated under reduced pressure, ethyl acetate (20 ml) was added to the residue, and the whole was washed with a saturated aqueous sodium hydrogencarbonate solution (20 ml) and saturated brine (5 ml) successively. The organic layer was dried over sodium sulfate, and ethyl acetate was evaporated under reduced pressure. The residue was purified by basic silica gel column chromatography to give the target compound (0.21 g, 33%) as a colorless oily matter.

IR (neat): 2092, 2846, 1644, 1602 cm$^{-1}$

The following compounds were obtained in a manner similar to Present Compound Preparation Example 2.

5-(4-Pyridyl)valeric acid N-(1-adamantyl)methyl-N-propylamide (Compound No. 2-2)

IR (neat): 3067, 2903, 2847, 1644, 1602 cm$^{-1}$ 5-(4-Pyridyl)valeric acid N-(1-adamantyl)methyl-N-pentylamide (Compound No. 2-3)

IR (neat): 2903, 2847, 1644, 1601, 1454 cm$^{-1}$ 5-(4-Pyridyl)valeric acid N,N-dibutylamide (Compound No. 2-4)

IR (neat): 2958, 2932, 1641, 1602 cm$^{-1}$ 5-(4-Pyridyl)valeric acid N,N-diisopentylamide (Compound No. 2-5)

IR (neat): 2956, 2870, 1639, 1603 cm$^{-1}$ 5-(4-Pyridyl)valeric acid N-[2-(1-adamantyl)ethyl]-N-(2-butenyl)amide (Compound No. 2-6)

IR (neat): 2903, 2847, 1642, 1602 cm$^{-1}$ 5-(4-Pyridyl)valeric acid N-[2-(1-adamantyl)ethyl]-N-[2-[N'-(t-butoxycarbonyl)-N'-methylamino]ethyl]amide (Compound No. 2-7)

IR (neat): 2904, 2847, 1695, 1644, 1602 cm$^{-1}$ 5-(4-Pyridyl)valeric acid N-[3-(1-adamantyl)propyl]-N-propylamide (Compound No. 2-8)

IR (neat): 2902, 2846, 1643, 1602 cm$^{-1}$ 5-(4-Pyridyl)valeric acid N-pentyl-N-phenethylamide (Compound No. 2-9)

IR (neat): 2930, 2860, 1642, 1602 cm$^{-1}$ 5-(4-Pyridyl)valeric acid N-[2-(1-adamantyl)ethyl]-N-(2-dimethylaminoethyl)amide (Compound No. 2-10)

IR (neat): 2903, 2847, 1639, 1605 cm$^{-1}$ 5-(4-Pyridyl)valeric acid N-(2-cyclhexylethyl)-N-pentylamide (Compound No. 2-11)

IR (neat): 2924, 2853, 1644, 1601 cm$^{-1}$ 5-(4-Pyridyl)valeric acid N,N-bis[2-(1-adamantyl)ethyl]amide (Compound No. 2-12)

IR (neat): 2901, 2846, 1643, 1602 cm$^{-1}$ 5-(4-Pyridyl)valeric acid N-[2-(1-adamantyl)ethyl]-N-(3,3,3-trifluoropropyl)amide (Compound No. 2-13)

IR (neat): 2904, 2848, 1647, 1602 cm$^{-1}$ 5-(4-Pyridyl)valeric acid N-[2-(1-adamantyl)ethyl]-N-pentylamide (Compound No. 2-14)

IR (neat): 2903, 2847, 1736, 1643, 1602 cm$^{-1}$ 3-(4-Pyridylmethylthio)propionic acid N-[2-(1-adamantyl)ethyl]-N-pentylamide (Compound No. 2-15)

IR (neat): 2903, 1643, 1599 cm$^{-1}$

2-Methyl-3-(4-pyridylmethylthio)propionic acid N-[2-(1-adamantyl)ethyl]-N-pentylamide (Compound No. 2-16)

IR (neat): 2903, 1639, 1600 cm$^{-1}$ 2-(t-Butoxycarbonyl)amino-3-(4-pyridylmethylthio)propionic acid N-[2-(1-adamantyl)ethyl]N-pentylamide (Compound No. 2-17)

IR (neat): 3284, 2903, 1705, 1644 cm$^{-1}$

2-[2-(4-Pyridyl)ethylthio]acetic acid N-[2-(1-adamantyl)ethyl]-N-pentylamide (Compound No. 2-18)

IR (neat): 2902, 1635, 1602 cm$^{-1}$ (2R)-2-(t-Butoxycarbonyl)amino-3-[2-(4-pyridyl)ethylthio]propionic acid N-[2-(1-adamantyl)ethyl]-N-pentylamide (Compound No. 2-19)

IR (neat): 3287, 2903, 1705, 1644, 1602 cm$^{-1}$
[α]$^{20}_D$: −19.0° (MeOH, C0.43)

6-(4-Pyridyl)caproic acid N-[2-(1-adamantyl)ethyl]-N-pentylamide (Compound No. 2-20)

IR (neat): 2903, 1644, 1602 cm$^{-1}$ 4-(4-Pyridyl)butyric acid N-[2-(1-adamantyl)ethyl]-N-pentylamide (Compound No. 2-21)

IR (neat): 2903, 1644, 1602 cm$^{-1}$

Present Compound Preparation Example 3

1-[2-(1-Adamantyl)ethyl]-1-(2-methylaminoethyl)-3-[3-(4-pyridyl)propyl]urea dihydrochloride (Compound No. 3-1)

Methanol (4.4 ml) was added to 1-[2-(1-adamantyl)ethyl]-1-[2-[N-(t-butoxycarbonyl)-N-methylamino]ethyl]-3-[3-(4-pyridyl)propyl]urea (Compound No. 1-26, 0.30 g, 0.60 mmol), and the mixture was stirred at room temperature in a vessel equipped with a calcium chloride tube. A 10% solution of hydrogen chloride in methanol (4.4 ml) was added to the mixture, and the whole was stirred for one day and then concentrated under reduced pressure to give the target compound (0.30 g, quantitatively) as pale yellow amorphous powder.

IR (neat): 3351, 2904, 2846, 1634, 1538 cm$^{-1}$

The following compounds were obtained in a manner similar to Present Compound Preparation Example 3.

1-(2-Cyclohexylethyl)-1-(2-methylaminoethyl)-3-(4-pyridyl)methylurea dihydrochloride (Compound No. 3-2)

IR (neat): 3323, 2923, 2850, 1638, 1529, 1449 cm$^{-1}$

1-[2-(1-Adamantyl)ethyl]-1-amino-3-[3-(4-pyridyl)propyl]urea dihydrochloride (Compound No. 3-3)

IR (KBr): 3410, 2902, 1637 cm$^{-1}$
mp: ca. 100° C.

2-Amino-3-(4-pyridylmethylthio)propionic acid N-[2-(1-adamantyl)ethyl]-N-pentylamide dihydrochloride (Compound No. 3-4)

IR (neat): 3402, 2901, 1638, 1608, 1503 cm$^{-1}$ 5-(4-Pyridyl)valeric acid N-[2-(1-adamantyl)ethyl]-N-(2-methylaminoethyl)amide (Compound No. 3-5)

IR (neat): 3312, 2902, 2846, 1643, 1602, 1450, 1416 cm$^{-1}$ (2R)-2-Amino-3-[2-(4-pyridyl)ethylthio]propionic acid N-[2-(1-adamantyl)ethyl]-N-pentylamide dihydrochloride (Compound No. 3-6)

IR (KBr): 3423, 2902, 1638, 1609 cm$^{-1}$
$[\alpha]^{20}_D$: −4.9° (H$_2$O, C0.52)

1-[2-(1-Adamantyl)ethyl]-1-pentyl-3-[2-(4-pyridyl)oxyethyl]urea (Compound No. 3-7)

IR (neat): 3246, 2903, 2846, 1698, 1604 cm$^{-1}$

Present Compound Preparation Example 4

4-[3-[3-[2-(1-Adamantyl)ethyl]-3-pentylureido]propyl]-1-methylpyridinium iodide (Compound No. 4-1)

Methyl iodide (90 µl, 1.5 mmol) was added to a solution of 1-[2-(1-adamantyl)ethyl]-1-pentyl-3-[3-(4-pyridyl)propyl]urea (Compound No. 1-1, 0.30 g, 0.73 mmol) in acetone (1.5 ml) at room temperature, and the mixture was stirred overnight. The reaction mixture was concentrated under reduced pressure, and the precipitated crystals were filtered off with ethyl acetate to give the target compound (389 mg, 96%).

IR (KBr): 3374, 2926, 2900, 1616, 1526 cm$^{-1}$
mp: 168.0-171.0° C.

The following compounds were obtained in a manner similar to Present Compound Preparation Example 4.

4-[3-[3-[2-(1-Adamantyl)ethyl]-3-[2-[N-(t-butoxycarbonyl)-N-methylamino]ethyl]ureido]propyl]-1-methylpyridinium iodide (Compound No. 4-2)

IR (neat): 3342, 2903, 2846, 1682, 1644, 1520, 1235, 1166 cm$^{-1}$

4-[3-[3-[2-(1-Adamantyl)ethyl]-3-[2-[N-(t-butoxycarbonyl)amino]ethyl]ureido]propyl]-1-benzylpyridinium bromide (Compound No. 4-3)

IR (KBr): 3312, 2907, 2846, 1714, 1694, 1625, 1534, 1246, 1171 cm$^{-1}$
mp: 97° C.

Present Compound Preparation Example 5

3-(4-pyridyl)propyl N-[2-(1-adamantyl)ethyl]-N-pentylcarbamate (Compound No. 5-1)

4-Pyridinepropanol (528 mg, 3.85 mmol) was dissolved in acetonitrile (20 ml) at room temperature, and then triethylamine (1.61 ml, 11.6 mmol) was added to the solution. Further, N,N'-disuccinimidyl carbonate (1.48 g, 5.87 mmol) was added to the mixture, and the whole was stirred for 2.5 hours. The reaction mixture was concentrated under reduced pressure, and ethyl acetate (100 ml) and a saturated aqueous sodium hydrogencarbonate solution (50 ml) were added to the residue. After separation, the organic layer was washed with a saturated aqueous sodium chloride solution (50 ml) and dried over anhydrous sodium sulfate. The solvent was evaporated under reduced pressure. The residue was dried under reduced pressure and dissolved in anhydrous methylene chloride (10 ml). Next, a solution of 2-(1adamantyl)-N-pentylethylamine hydrochloride (Intermediate No. 1-1, 1.32 g, 4.62 mmol) and triethylamine (0.80 ml, 5.7 mmol) in methylene chloride (90 ml) was added thereto, and the mixture was stirred for 1.5 hours. The reaction mixture was washed with a saturated aqueous sodium hydrogencarbonate solution (50 ml) and a saturated aqueous sodium chloride solution (50 ml) successively and dried over anhydrous sodium sulfate. The solvent was evaporated under reduced pressure, and the residue was purified by silica gel column chromatography to give the target compound (1.54 g, 97%) as an oily matter.

IR (neat): 2903, 2847, 1742, 1698 cm$^{-1}$

The following compounds were obtained in a manner similar to Present Compound Preparation Example 5.

1-[2-(1-Adamantyl)ethyl]-1-[2-(N-cyclohexyloxy-
carbonyl-N-methylamino)ethyl]-3-[3-(4-pyridyl)
propyl]urea (Compound No. 5-2)

IR (neat): 3350, 2904, 2847, 1682, 1633, 1604, 1531 cm$^{-1}$ 3-(4-Pyridyl)propyl N-[3-(1-adamantyl)propyl]-N-
propylcarbamate (Compound No. 5-3)

IR (neat): 2901, 2846, 1740, 1695, 1645, 1602, 1451, 1423 cm−1

3-(4-Pyridyl)propyl N-[2-(1-adamantyl)ethyl]-N-(3,
3,3-trifluoropropyl)carbamate (Compound No. 5-4)

IR (neat): 2903, 2847, 1705, 1603, 1482, 1451, 1425 cm$^{-1}$ 3-(4-Pyridyl)propyl N-[2-(1-adamantyl)ethyl]-N-[2-
[N'-(t-butoxycarbonyl)-N'-methylamino]ethyl]car-
bamate (Compound No. 5-5)

IR (neat): 2903, 2847, 1699, 1603, 1480, 1424 cm$^{-1}$

2-Methyl-3-(4-pyridyl)propyl N-[2-(1-adamantyl)
ethyl]-N-pentylcarbamate (Compound No. 5-6)

IR (neat): 2904, 2847, 1701, 1602, 1450, 1424, 1381 cm$^{-1}$

Present Compound Preparation Example 6

1-[2-(1-Adamantyl)ethyl]-3-[3-(4-pyridyl)propyl]
hexahydro-2,4-pyrimidinedione hydrochloride
(Compound No. 6-1)

A 4 N solution of hydrogen chloride in 1,4-dioxane (2.5 ml) was added to 1-[2-(1-adamantyl)ethyl]-1-[2-(t-butoxycarbonyl)ethyl]-3-[3-(4-pyridyl)propyl]urea (Compound No. 1-69, 0.23 g, 0.49 mmol), and the mixture was stirred at room temperature overnight. The reaction mixture was concentrated under reduced pressure, and a 1 N aqueous sodium hydroxide solution (20 ml) and ethyl acetate (30 ml) were added to the residue. After separation, the ethyl acetate layer was washed with water (20 ml) and a saturated aqueous sodium chloride solution (20 ml) successively, dried over anhydrous magnesium sulfate and concentrated under reduced pressure. The obtained oily matter was dissolved in diethyl ether (20 ml), a 4 N solution of hydrogen chloride in ethyl acetate (0.50 ml, 2.00 mol) was added thereto under ice-cooling, the reaction mixture was concentrated under reduced pressure, and the precipitated solid was filtered off to give the target compound (0.17 g, 79%).

IR (KBr): 2902, 2437, 1710, 1666 cm$^{-1}$
mp: 177.0-178.5° C.

The following compounds were obtained in a manner similar to Present Compound Preparation Example 6.

1-[2-(Cyclohexyl)ethyl]-3-(4-pyridyl)methylhexahy-
dro-2,4-pyrimidinedione hydrochloride (Compound
No. 6-2)

IR (KBr): 2925, 2850, 1718, 1671, 1600, 1493, 1450 cm$^{-1}$
mp: 64.0-74.5° C.

3-[2-(1-Adamantyl)ethyl]-1-[3-(4-pyridyl)propyl]
hexahydro-2,4-pyrimidinedione hydrochloride
(Compound No. 6-3)

IR (KBr): 2906, 2845, 1716, 1696, 1658, 1486 cm$^{-1}$
mp: 170° C.

Present Compound Preparation Example 7

1-[2-(1-Adamantyl)ethyl]-1-pentyl-3-[3-(4-pyridyl)
propyl]thiourea (Compound No. 7-1)

A solution of 4-(3-aminopropyl)pyridine (Intermediate No. 2-1, 0.24 g, 1.8 mmol) in anhydrous tetrahydrofuran (10 ml) was added to 1,1'-thiocarbonyldiimidazole (0.31 g, 1.8 mmol) under a nitrogen atmosphere, and the mixture was stirred at room temperature. After one hour, a solution of 2-(1-adamantyl)-N-pentylethylamine hydrochloride (Intermediate No. 1-1, 0.50 g, 1.8 mmol) in anhydrous tetrahydrofuran (10 ml) was added to the mixture, and the whole was refluxed for 2.5 hours. The reaction mixture was allowed to stand, and then ethyl acetate (50 ml) and a saturated aqueous sodium hydrogencarbonate solution (50 ml) were added to the reaction mixture. After separation, the ethyl acetate layer was washed with a saturated aqueous sodium chloride solution (50 ml), dried over anhydrous magnesium sulfate and concentrated under reduced pressure. Then the obtained concentrate was purified by silica gel column chromatography to give the target compound (0.18 g, 24%).

IR (neat): 3304, 2902, 2846, 1603, 1530, 1345 cm$^{-1}$

The following compound was obtained in a manner similar to Present Compound Preparation Example 7.

1-(2-Hydroxyethyl)-1-phenethyl-3-[3-(4-pyridyl)
propyl]thiourea (Compound No. 7-2)

IR (KBr): 3022, 2920, 2876, 1606, 1585 cm$^{-1}$
mp: 105.6-107.1° C.

Present Compound Preparation Example 8

1-Phenethyl-3-[3-(4-pyridyl)propyl]-2-imidazolidi-
nethione (Compound No. 8-1)

Anhydrous tetrahydrofuran (2.5 ml) was added to a mixture of 1-(2-hydroxyethyl)-1-phenethyl-3-[3-(4-pyridyl)propyl]thiourea (Compound No. 7-2, 601 mg, 1.75 mmol) and triphenylphosphine (913 mg, 3.49 mmol), and the whole was stirred under ice/methanol-cooling. A solution of diisopropyl azodicarboxylate (710 mg, 3.49 mmol) in anhydrous tetrahydrofuran was added dropwise thereto, and after 10 minutes, ethyl acetate (100 ml) was added to the reaction mixture. The whole was washed with a saturated aqueous sodium hydrogencarbonate solution (40 ml) and saturated brine (40 ml) successively, and the organic layer was dried over sodium sulfate and concentrated under reduced pressure. The residue was purified by silica gel column chromatography, and the obtained solid was filtered off with hexane to give the target compound (107 mg, 19%) as crystals.

IR (KBr): 3064, 3018, 2926, 2858, 1601, 1560, 1498, 1456 cm$^{-1}$
mp: 99.5-104.0° C.

Present Compound Preparation Example 9

1-[2-(1-Adamantyl)ethyl]-3-[3-(4-pyridyl)propyl] hexahydropyrimidin-2-one (Compound No. 9-1)

To a solution of 1-adamantaneacetic acid (1.50 g, 7.72 mmol) in anhydrous methylene chloride (30.0 ml) were added 1-hydroxybenzotriazole (1.15 g, 8.49 mmol), β-alanine ethyl ester hydrochloride (1.30 g, 8.49 mmol), 1-ethyl-3-(3-dimethylaminopropyl)carbodiimide hydrochloride (1.63 g, 8.49 mmol) and N-methylmorpholine (2.05 ml, 18.7 mmol) under ice-cooling, and the mixture was stirred at room temperature overnight. The reaction mixture was concentrated under reduced pressure, and ethyl acetate (50 ml) was added to the residue. The whole was washed with a 10% aqueous citric acid solution (50 ml), water (50 ml), a saturated aqueous sodium hydrogencarbonate solution (50 ml), water (50 ml) and a saturated aqueous sodium chloride solution (50 ml) successively. The organic layer was dried over anhydrous magnesium sulfate and concentrated under reduced pressure to give ethyl 3-[1-(adamantyl)methylcarboxamido]propionate (2.48 g, quantitatively) as a white solid.

Next, ethyl 3-[(1-adamantyl)methylcarboxamido]propionate (2.40 g, 8.18 mmol) was dissolved in ethanol (5 ml), a 2 N aqueous sodium hydroxide solution (4.50 ml, 9.00 mmol) was added to the mixture under ice-cooling, and then the whole was stirred at room temperature for two hours. Under ice-cooling, 2 N hydrochloric acid (15 ml) was added to the reaction mixture to weakly acidify it, and the whole was extracted with ethyl acetate (70 ml). The organic layer was washed with water (50 ml) and a saturated aqueous sodium chloride solution (50 ml) successively, dried over anhydrous magnesium sulfate and concentrated under reduced pressure. The precipitated solid was filtered off with diethyl ether to give 3-[(1-adamantyl)methylcarboxamido]propionic acid (1.43 g, 70.1%).

Next, to a solution of 3-[(1-adamantyl)-methylcarboxamido]propionic acid (1.4 g, 5.6 mmol) in anhydrous methylene chloride (10 ml) were added 1-hydroxybanzotriazole (0.83 g, 6.2 mmol), 1-ethy-3-(3-dimethylaminopropyl)carbodiimide hydrochloride (1.2 g, 6.2 mmol), 4-(3-aminopropyl)pyridine (Intermediate No. 2-1, 0.80 g, 5.9 mmol) and N-methylmorpholine (0.68 ml, 6.2 mmol) under ice-cooling, and then the mixture was stirred at room temperature overnight. The reaction mixture was concentrated under reduced pressure, ethyl acetate (50 ml) was added to the residue, and the whole was washed with a saturated aqueous sodium hydrogencarbonate solution (30 ml), water (30 ml) and a saturated aqueous sodium chloride solution (30 ml) successively. The organic layer was dried over anhydrous magnesium sulfate and concentrated under reduced pressure. The precipitated solid was filtered off with diethyl ether to give 3-[(1-adamantyl)methylcarboxamido]propionic acid 3-(4-pyridyl)propylamide (1.9 g, 88%).

Anhydrous diethyl ether (20 ml) was added to lithium aluminum hydride (0.45 g, 12 mmol) under ice-cooling. Then a solution of the obtained 3-[(1-adamantyl)-methylcarboxamido]propionic acid 3-(4-pyridyl)propylamide (0.50 g, 1.3 mmol) in anhydrous tetrahydrofuran (10 ml) was added dropwise to the mixture over 15 minutes, and then the whole was stirred at room temperature overnight and further refluxed for 4.5 hours. Then a 2 N aqueous sodium hydroxide solution (30 ml) and ethyl acetate (30 ml) were added to the reaction mixture carefully under ice-cooling. After separation, the ethyl acetate layer was washed with water (30 ml) and a saturated aqueous sodium chloride solution (30 ml) successively, dried over anhydrous magnesium sulfate and concentrated under reduced pressure. The residue was purified by silica gel column chromatography to give N-[2-(1-adamantyl)ethyl]-N'-[3-(4-pyridyl)propyl]-1,3-propanediamine (0.05 g, 10%).

A solution of the obtained N-[2-(1-adamantyl)ethyl]-N'-[3-(4-pyridyl)propyl]-1,3-propanediamine (80 mg, 0.23 mmol) in anhydrous methylene chloride (10 ml) and a solution of 1,1'-carbonyldiimidazole (40 mg, 0.26 mmol) in anhydrous methylene chloride (10 ml) were simultaneously added dropwise to anhydrous methylene chloride (60 ml) at room temperature with stirring over 20 minutes. The mixture was stirred overnight, then the reaction mixture was concentrated under reduced pressure, and the residue was purified by silica gel column chromatography to give the target compound (8.0 mg, 9.4%).

IR (neat): 3400, 2902, 2846, 1625, 1531, 1451 cm$^{-1}$

Present Compound Preparation Example 10

1-Acetylamino-1-[2-(1-adamantyl)ethyl]-3-[3-(4-pyridyl)propyl]urea (Compound No. 10-1)

Pyridine (2.0 ml) and acetic anhydride (1.0 ml) were added to 1-[2-(1-adamantyl)ethyl]-1-amino-3-[3-(4-pyridyl)propyl]urea dihydrochloride (Compound No. 3-3, 0.20 g, 0.47 mmol) at room temperature, and the mixture was stirred for 15 minutes. The reaction mixture was concentrated under reduced pressure, and the concentrate was distributed between ethyl acetate (10 ml) and water (10 ml). The organic layer was washed with a saturated aqueous sodium hydrogencarbonate solution (10 ml) and saturated brine (10 ml) successively and dried over anhydrous magnesium sulfate. The solvent was evaporated under reduced pressure, and the residue was purified by silica gel column chromatography to give the target compound (0.11 g, 58%).

IR (KBr): 3374, 3163, 2907, 1694, 1638 cm$^{-1}$ mp: 140.0-146.0° C.

The following compounds were obtained in a manner similar to Present Compound Preparation Example 10. Acid chlorides were used, if necessary.

1-[2-(N-Acetyl-N-methylamino)ethyl]-1-[2-(1-adamantylethyl)-3-[3-(4-pyridyl)propyl]urea (Compound No. 10-2)

IR (neat): 3337, 2902, 1632, 1535, 1492 cm$^{-1}$

1-[2-(1-Adamantyl)ethyl]-1-[2-(N-isonicotinoyl-N-methylamino)ethyl]-3-[3-(4-pyridyl)propyl]urea (Compound No. 10-3)

IR (neat): 3350, 2902, 2846, 1633, 1531, 1450, 1408 cm$^{-1}$

1-[2-(1-Adamantyl)ethyl]-1-[2-[N-methyl-N-(methylsulfonyl)amino]ethyl]-3-[3-(4-pyridyl)propyl]urea (Compound No. 10-4)

IR (KBr): 3319, 2902, 2845, 1616, 1540, 1326, 1142 cm$^{-1}$ mp: 164.9-167.2° C.

1-[2-(1-Adamantyl)ethyl]-1-[2-[N-methyl-N-(p-tolylsulfonyl)amino]ethyl]-3-[3-(4-pyridyl)propyl] urea (Compound No. 10-5)

IR (neat): 3358, 2902, 2846, 1633, 1603, 1531, 1343, 1161 cm$^{-1}$

1-[2-(1-Adamantyl)ethyl]-1-[2-[N-(3,3-dimethylbutyryl)-N-methylamino]ethyl]-3-[3-(4-pyridyl)propyl]urea (Compound No. 10-6)

IR (KBr): 3325, 2906, 2845, 1652, 1616, 1534 cm$^{-1}$
mp: 101.4-102.4° C.

1-[2-(1-Adamantyl)ethyl]-1-[2-N-ethoxycarbonyl-N-methylamino]ethyl]-3-[3-(4-pyridyl)propyl]urea (Compound No. 10-7)

IR (neat): 3350, 2902, 2846, 1698, 1633, 1532 cm$^{-1}$

1-[2-(1-Adamantyl)ethyl]-1-[2-[N-(t-butoxycarbonyl)amino]ethyl]-3-[3-(4-pyridyl)propyl]urea (Compound No. 10-8)

IR (KBr): 3312, 2905, 2845, 1710, 1637, 1606, 1534, 1269, 1249, 1174 cm$^{-1}$
mp: 158.0-160.5° C.

1-[2-(1-Adamantyl)ethyl]-1-[2-[N-(t-butoxycarbonyl)-N-ethylamino]ethyl]-3-[3-(4-pyridyl)propyl]urea (Compound No. 10-9)

IR (neat): 3349, 2902, 2846, 1693, 1667, 1633, 1603, 1531, 1452, 1416 cm$^{-1}$

1-[2-(1-Adamantyl)ethyl]-1-[2-[N-(1,1-dimethyl-2,2,2-trichloroethoxycarbonyl)-N-methylamino}ethyl]-3-[3-(4-pyridyl)propyl]urea (Compound No. 10-10)

IR (neat): 3359, 2903, 2846, 1707, 1636, 1603, 1534 cm$^{-1}$
mp: 47.0-52.0° C.

1-[2-(1-Adamantyl)ethyl]-1-[2-[N-(1,1-dimethylpropoxycarbonyl)-N-methylamino]ethyl]-3-[3-(4-pyridyl)propyl]urea (Compound No. 10-11)

IR (neat): 3349, 2972, 2902, 2846, 1695, 1631, 1603, 1534, 1226, 1159 cm$^{-1}$

1-[2-(1-Adamantyl)ethyl]-1-[2-(N-isopropoxycarbonyl-N-methylamino)ethyl]-3-[3-(4-pyridyl)propyl]urea (Compound No. 10-12)

IR (neat): 3350, 2903, 2846, 1696, 1632, 1603, 1530 cm$^{-1}$ (−)-1-[2-(1-Adamantyl)ethyl]-1-[2-(N-menthoxycarbonyl-N-methylamino)ethyl]-3-[3-(4-pyridyl)propyl]urea (Compound No. 10-13)

IR (neat): 3350, 2904, 2847, 1694, 1633, 1603, 1530 cm$^{-1}$
$[\alpha]^{20}_D$: −27.5° (MeOH, C1.0)

1-[2-(1-Adamantyl)ethyl]-1-[2-[N-(3,3-dimethylbutyryl)-N-methylamino]ethyl]-3-[2-methyl-3-(4-pyridyl)propyl]urea (Compound No. 10-14)

IR (neat): 3324, 2902, 2846, 1633, 1537 cm$^{-1}$ 5-(4-Pyridyl)valeric acid N-[2-(1-adamantyl)ethyl]-N-[2-(N-isopropoxycarbonyl-N-methylamino)ethyl]amide (Compound No. 10-15)

IR (neat): 3553, 2978, 2903, 2847, 1697, 1646 cm$^{-1}$ 5-(4-Pyridyl)valeric acid N-[2-(1-adamantyl)ethyl]-N-[2-(N-benzyloxycarbonyl-N'-methylamino)ethyl]amide (Compound No. 10-16)

IR (neat): 3387, 3030, 2903, 2847, 1701, 1646, 1602, 1453, 1422 cm$^{-1}$ 5-(4-Pyridyl)valeric acid N-[2-(1-adamantyl)ethyl]-N-[2-[N-(3,3-dimethylbutyryl)-N'-methylamino]ethyl]amide (Compound No. 10-17)

IR (neat): 3501, 2903, 2847, 1645, 1603, 1455, 1417 cm$^{-1}$

Present Compound Preparation Example 11

1-[2-(1-Adamantyl)ethyl]-1,3-dimethyl-3-[3-(4-pyridyl)propyl]urea (Compound No. 11-1)

A solution of triphosgene (190 mg, 0.640 mmol) in dichloromethane (6.0 ml) was stirred at room temperature under a nitrogen atmosphere. A solution of 2-(1-adamantyl)-N-methylethylamine (Intermediate No. 3-1, 330 mg, 1.71 mmol) and diisopropylethylamine (0.357 ml, 2.05 mmol) in dichloromethane (6.0 ml) was added dropwise thereto over 17 minutes. After eight minutes, a solution of N-methyl-3-(4-pyridyl)propylamine (Intermediate No. 3-3, 264 mg, 1.78 mmol) and diisopropylethylamine (0.357 ml, 2.05 mmol) in dichloromethane (5.1 ml) was added to the mixture all at once, and the whole was stirred for 20 hours. The reaction mixture was diluted with diethyl ether (40 ml), the whole was washed with a saturated aqueous sodium hydrogencarbonate solution (40 ml) twice and a saturated aqueous sodium chloride solution (40 ml) successively, and the organic layer was dried over magnesium sulfate. The solvent was evaporated under reduced pressure, and the residue was purified by silica gel column chromatography to give the target compound (335 mg, 54%).

IR (neat): 2903, 2846, 1638, 1602, 1492 cm$^{-1}$

Present Compound Preparation Example 12

1-[2-(1-Adamantyl)ethyl]-1-hydroxy-3-[3-(4-pyridyl)propyl]urea (Compound No. 12-1)

Two normality hydrochloric acid (4.0 ml) was added to a solution of 1-[2-(1-adamantyl)ethyl]-1-benzyloxy-3-[3-(4-pyridyl)propyl]urea (Compound No. 1-28, 438 mg, 0.978 mmol) in methanol (9.78 ml), and a nitrogen gas was bubbled through the mixture. Ten percent palladium on carbon (43 mg) was added to the mixture, and the whole was stirred under hydrogen at one atm for three days. The palladium on carbon was filtered out, the filtrate was concentrated under reduced pressure, and the concentrate was diluted with diethyl ether (30 ml). The whole was washed with a saturated aqueous sodium hydrogencarbonate solution (30 ml) and a saturated aqueous sodium chloride solution (30 ml) successively, and the organic layer was dried over magnesium sulfate. The solvent was evaporated under reduced pressure, and the residue was purified by silica gel column chromatography to give the target compound (119 mg, 34%).

IR (KBr): 3438, 3152, 2903, 2847, 1650 cm$^{-1}$ mp: 101.0-102.59° C.

Present Compound Preparation Example 13

1-[2-(1-Adamantyl)ethyl]-1-pentyl-3-[3-(4-pyridyl)propyl]urea hydrochloride (Compound No. 13-1)

A 4 N solution of hydrogen chloride in ethyl acetate (0.400 ml, 1.60 mmol) was added to a solution of 1-[2-(1-adamantyl)ethyl]-1-pentyl-3-[3-(4-pyridyl)propyl]urea (Compound No. 1-1, 200 mg, 0.486 mmol) in chloroform (0.3 ml). The solvent was evaporated under reduced pressure, and the precipitated solid was washed with ethyl acetate and filtered off. The obtained crude crystals were recrystallized from 2-butanone (5.0 ml) to give the target compound (94 mg, 43%).

IR (KBr): 3322, 3050, 2902, 2496, 1621, 1534, 1450 cm$^{-1}$
mp: 157.0-158.0° C.

The following compounds were obtained in a manner similar to Present Compound Preparation Example 13.

1-[2-(1-Adamantyl)ethyl]-1-propyl-3-[3-(4-pyridyl)propyl]urea hydrochloride (Compound No. 13-2)

IR (neat): 3338, 2901, 2845, 1620, 1450 cm$^{-1}$ 1-(2-Cyclohexylethyl)-3-(4-pyridyl)methyl-1-(2-thienyl)methylurea hydrochloride (Compound No. 13-3)

IR (KBr): 3296, 2923, 1635, 1599, 1518 cm$^{-1}$
mp: 161.8-164.4° C.

1-[2-(1-Adamantyl)ethyl]-1-butyl-3-[3-(4-pyridyl)propyl]urea hydrochloride (Compound No. 13-4)

IR (neat): 3331, 2901, 2845, 1754, 1636, 1537 cm$^{-1}$ 1,1-Bis[2-(1-adamantyl)ethyl]-3-[3-(4-pyridyl)propyl]urea hydrochloride (Compound No. 13-5)

IR (KBr): 3289, 2900, 2844, 1637, 1560 cm$^{-1}$
mp: 120.0-122.5° C.

1-[2-(1-Adamantyl)ethyl]-1-(2-aminoethyl)-3-[3-(4-pyridyl)propyl]urea dihydrochloride (Compound No. 13-6)

IR (neat): 3358, 2902, 2846, 1634, 1538, 756 cm$^{-1}$

2-[2-(4-Pyridyl)ethylamino]acetic acid N-[2-(1-adamantyl)ethyl]-N-pentylamide dihydrochloride (Compound No. 13-7)

IR (KBr): 3424, 2902, 1651 cm$^{-1}$
mp: 133.7-137.0° C.

3-[N'-Methyl-N'-(4-pyridylmethyl)amino]propionic acid N-[2-(1-adamantyl)ethyl]-N-pentylamide dihydrochloride (Compound No. 13-8)

IR (KBr): 3424, 2901, 2846, 1641 cm$^{-1}$ 1,1-Diisopentyl-3-[3-(4-pyridyl)propyl]urea hydrochloride (Compound No. 13-9)

IR (KBr): 3082, 2956, 2869, 2614, 1626, 1526 cm$^{-1}$
mp: 120.5-131.7° C.

1-[3-(1-Adamantyl)propyl]-1-propyl-3-[3-(4-pyridyl)propyl]urea phosphate (Compound No. 13-10)

IR (KBr): 3517, 3423, 1642, 1594, 1539, 1508 cm$^{-1}$
mp: 148.0-149.0° C.

Present Compound Preparation Example 14

1-[2-(1-Adamantyl)ethyl]-3-[3-hydroxy-3-(4-pyridyl)propyl]-1-pentylurea (Compound No. 14-1)

A solution of 1-[2-(1-adamantyl)ethyl]-3-[3-(t-butyldimethylsilyloxy)-3-(4-pyridyl)propyl]-1-pentylurea (Compound No. 1-138, 136 mg, 0.250 mmol) in 10% hydrogen chloride-methanol (2.3 ml) was stirred at room temperature for three days. The solvent was evaporated under reduced pressure, and the residue was distributed between ethyl acetate (50 ml), water (30 ml) and a 1 N aqueous sodium hydroxide solution (20 ml). The organic layer was washed with a saturated aqueous sodium chloride solution (40 ml) and dried over anhydrous sodium sulfate. The solvent was evaporated under reduced pressure, and the residue was purified by silica gel column chromatography to give the target compound (59.2 mg, colorless amorphous powder, 55.3%).

IR (neat): 3339, 2904, 2847, 1622, 1605, 1532 cm$^{-1}$

Present Compound Preparation Example 15 cis-1-[2-(1-adamantyl)ethyl]-1-pentyl-3-[2-(4-pyridyl)cyclopropylmethyl]urea (Compound No. 15-1)

A 1.0 M solution of diethylzinc in hexane (3.1 ml, 3.1 mmol) and chloroiodomethane (0.44 ml, 6.1 mol) were added to a solution of (Z)-1-[2-(1-adamantyl)ethyl]-1-pentyl-3-[3-(4-pyridyl)-2-propenyl]urea (Compound No. 1-111, 0.25 g, 0.61 mmol) in anhydrous 1,2-dichloroethane (3 ml) under a nitrogen atmosphere and ice-cooling, and the mixture was stirred for one hour. A saturated aqueous ammonium chloride solution (10 ml) was added to the reaction mixture under ice-cooling, and the whole was stirred at room temperature for 20 minutes and then distributed between ethyl acetate (20 ml) and a saturated aqueous ammonium chloride solution (10 ml). The organic layer was washed with a saturated aqueous sodium chloride solution (10 ml) and dried over anhydrous magnesium sulfate. The solvent was evaporated under reduced pressure, and the obtained residue was purified by silica gel column chromatography to give the target compound (9.0 mg, 3.5%) as colorless crystals.

IR (KBr): 3340, 3025, 2903, 2847, 1617, 1603, 1525 cm$^{-1}$
mp: 128.0-130.0° C.

Present Compound Preparation Example 16

4-[3-[3-[2-(1-Adamantyl)ethyl]-3-pentylureido]propyl]pyridine N-oxide (Compound No. 16-1)

m-Chloroperbenzoic acid (2.5 g, 15 mmol) was added to a solution of 1-[2-(1-adamantyl)ethyl]-1-pentyl-3-[3-(4-pyridyl)-urea (Compound No. 1-1, 3.0 g, 7.3 mmol) in anhydrous dichloromethane (24 ml) at room temperature under a nitrogen atmosphere, and the mixture was stirred overnight. The reaction mixture was distributed between chloroform (20 ml) and a 1 N aqueous sodium hydroxide solution (60 ml). The organic layer was washed with water (10 ml) and a saturated aqueous sodium chloride solution (10 ml) successively and dried over anhydrous magnesium sulfate. The solvent was evaporated under reduced pressure, and the obtained residue was purified by silica gel column chromatography to give the target compound (2.92 g, 94.2%).

IR (KBr): 3346, 2902, 2845, 1622, 1538, 1217, 1178 cm$^{-1}$ mp:97.8-127.0° C.

Present Compound Preparation Example 17

1-[2-(1-Adamantyl)ethyl]-1-[2-[N-(2-methoxyethyl)-N-methylamino]ethyl]-3-[3-(4-pyridyl)propyl]urea (Compound No. 17-1)

To N,N-dimethylformamide (20 ml) were added 1-[2-(1-adamantyl)ethyl]-1-(2-methylaminoethyl)-3-[3-(4-pyridyl)propyl]urea (1.50 g, 3.76 mmol), which is a free base of Compound No. 3-1, potassium carbonate (1.56 g, 11.3 mmol) and sodium iodide (1.69 g, 11.3 mmol) at room temperature, then 2-chloroethyl methyl ether (412 μl, 4.51 mmol) was added to the mixture, and the whole was heated at 80° C. and stirred overnight, then diethyl ether (50 ml) and water (100 ml) were added to the reaction mixture. After extraction, the obtained organic layer was washed with water (100 ml) and a saturated aqueous sodium chloride solution (50 ml) successively, dried over anhydrous magnesium sulfate and concentrated under reduced pressure. The residue was purified by silica gel column chromatography to give the target compound (552 mg, 32.1%) as a pale yellow oily matter.

IR (neat): 3350, 2901, 1643, 1602, 1531 cm$^{-1}$

Present Compound Preparation Example 18

2-[2-(4-Pyridyl)ethylamino]acetic acid N-[2-(1-adamantyl)ethyl]-N-pentylamide (Compound No. 18-1)

Bromoacetic acid (0.50 g, 3.6 mmol) was dissolved in anhydrous tetrahydrofuran (20 ml), and the solution was stirred at –15° C. under a nitrogen atmosphere. N-Methylmorpholine (0.40 ml, 3.6 mmol) and isobutyl chlorocarbonate (0.45 ml, 3.5 mmol) were added to the solution. Then a solution of a free base of 2-(1-adamantyl)-N-pentylethylamine hydrochloride (Intermediate No. 1-1, 1.0 g, 3.5 mmol) in anhydrous tetrahydrofuran (20 ml) was added dropwise to the mixture. The whole was stirred at 0° C. for 1.5 hours, then a saturated aqueous sodium hydrogencarbonate solution (70 ml) and ethyl acetate (70 ml) were added to the reaction mixture to distribute it. The ethyl acetate layer was washed with water (70 ml) and a saturated aqueous sodium chloride solution (70 ml) successively, dried over anhydrous magnesium sulfate and concentrated under reduced pressure to give 2-bromoacetic acid N-[2-(1-adamantyl)ethyl]-N-pentylamide (1.3 g, quantitatively) as an oily matter.

Next, 2-bromoacetic acid N-[2-(1-adamantyl)ethyl]-N-pentylamide (1.3 g, 3.5 mmol) was dissolved in anhydrous N,N-dimethylformamide (30 ml), potassium carbonate (1.5 g, 11 mmol), methyl iodide (1.6 g, 11 mmol) and 4-(2-aminoethyl)pyridine (0.43 g, 3.5 mmol) were added to the solution, and the mixture was stirred at an external temperature of 75° C. overnight. Water (100 ml) and diethyl ether (100 ml) were added to the reaction mixture to distribute it. The diethyl ether layer was washed with water (70 ml) twice and a saturated aqueous sodium chloride solution (120 ml) once successively, dried over anhydrous magnesium sulfate, and concentrated under reduced pressure. Then the obtained concentrate was purified by silica gel column chromatography to give the target compound (0.6 g, 40%) as an oily matter.

IR (neat): 3312, 2902, 2846, 1651, 1602, 1454 cm$^{-1}$

The following compounds were obtained in a manner similar to Present Compound Preparation Example 18.

3-[N'-Methy-N'-(4-pyridylmethyl)]aminopropionic acid N-[2-(1-adamantyl)ethyl]-N-pentylamide (Compound No. 18-2)

IR (neat): 2902, 2846, 1643 cm$^{-1}$

2-[2-(4-Pyridyl)ethoxy]acetic acid N-[2-(1-adamantyl)ethyl]-N-pentylamide (Compound No. 18-3)

IR (neat): 2902, 2846, 1650, 1602, 1451, 1113 cm$^{-1}$

Present Compound Preparation Example 19

(R)-1-[2-(4-Pyridyl)ethyl]-2-pyrrolidinecarboxylic acid N-[2-(1-adamantyl)ethyl]-N-pentylamide hydrochloride (Compound No. 19-1)

N-t-Butoxycarbonyl-L-proline (1.7 g, 8.0 mmol) was dissolved in anhydrous tetrahydrofuran (20 ml), and the solution was stirred at –15° C. under a nitrogen atmosphere. N-Methylmorpholine (0.90 ml, 8.0 mmol) and isobutyl chlorocarbonate (1.0 ml, 8.0 mmol) were added to the solution. After 10 minutes, a solution of a free base (2.0 g, 8.0 mmol) of Intermediate No. 1-1 in anhydrous tetrahydrofuran (20 ml) was added dropwise to the mixture over five minutes. The whole was stirred at 0° C. for 45 minutes and then at room temperature overnight. A saturated aqueous sodium hydrogencarbonate solution (50 ml) and ethyl acetate (50 ml) were added to the reaction mixture to distribute it. The ethyl acetate layer was washed with a 10% aqueous citric acid solution (50 ml), water (50 ml) and a saturated aqueous sodium chloride solution (50 ml) successively, dried over anhydrous magnesium sulfate and concentrated under reduced pressure. Then the obtained concentrate was purified by silica gel column chromatography to give intended (R)-1-(t-butoxycarbonyl)-2-pyrrolidinecarboxylic acid N-[2-(1-adamantyl)ethyl]-N-pentylamide (1.9 g, 52%) as an oily matter.

Next, 4 N hydrogen chloride/dioxane (20 ml, 81 mmol) was added to (R)-1-(t-butoxycarbonyl)-2-pyrrolidinecarboxylic acid N-[2-(1-adamantyl)ethyl]-N-pentylamide (1.8 g, 4.0 mmol), and then the mixture was stirred at room temperature for 1.5 hours. The reaction mixture was concentrated under reduced pressure to give (R)-2-pyrrolidinecarboxylic acid N-[2-(1-adamantyl)ethyl]-N-pentylamide hydrochloride (1.5 g, quantitatively) as an amorphous substance.

Next, (R)-2-pyrrolidinecarboxylic acid N-[2-(1-adamantyl)ethyl]-N-pentylamide hydrochloride (1.4 g, 3.7 mmol) was dissolved in anhydrous N,N-dimethylformamide (40 ml), potassium carbonate (2.6 g, 19 mmol), methyl iodide (1.7 g, 11 mmol) and 4-(2-chloroethyl)pyridine hydrochloride (0.70 g, 3.7 mmol) were added to the solution, and the mixture was stirred at an external temperature of 80° C. overnight. A 2 N aqueous sodium hydroxide solution (70 ml) and diethyl ether (70 ml) were added to the reaction mixture to distribute it. The diethyl ether layer was washed with water (70 ml) and a saturated aqueous sodium chloride solution (70 ml) successively, dried over anhydrous magnesium sulfate and concentrated under reduced pressure. Then the obtained concentrate was purified by silica gel column chromatography to give the target compound (0.80 g, 47%) as an oily matter.

IR (neat): 2902, 2846, 1644 cm$^{-1}$
$[\alpha]^{20}_D$: −48.1° (MeOH, C1.0)

The following compound was obtained in a manner similar to Present Compound Preparation Example 19.

(S)-1-[2-(4-Pyridyl)ethyl]-2-pyrrolidinecarboxylic acid N-[2-(1-adamantyl)ethyl]-N-pentylamide hydrochloride (Compound No. 19-2)

IR (neat): 2902, 2846, 1644, 1601 cm$^{-1}$
$[\alpha]^{20}_D$: +41.6° (MeOH, C1.0)

Present Compound Preparation Example 20

1-[2-(1-Adamantyl)ethyl]-1-[2-(N-ethylamino) ethyl]-3-[3-(4-pyridyl)propyl]urea (Compound No. 20-1)

Lithium aluminum hydride (890 mg, 23.5 mmol) was suspended in anhydrous diethyl ether (10 ml) under a nitrogen atmosphere, a solution of 1-[2-(acetylamino)ethyl]-1-[2-(1-adamantyl)ethyl]-3-[3-(4-pyridyl)propyl]urea (Compound No. 1-103, 4.86 g, 11.4 mmol) in anhydrous tetrahydrofuran (60 ml) was added dropwise to the suspension under ice-cooling with stirring over two hours, and the mixture was stirred at room temperature for 70 hours. Ethyl acetate (25 ml) was added to the reaction mixture under ice-cooling, then a 1 N aqueous sodium hydroxide solution (25 ml) was added thereto, and the resulting insoluble. matter was filtered out with Celite. The filtrate was distributed between ethyl acetate (25 ml) and water (25 ml). The organic layer was washed with a saturated aqueous sodium chloride solution (20 ml) and dried over anhydrous magnesium sulfate. The solvent was evaporated under reduced pressure, and the residue was purified by silica gel column chromatography to give the target compound (2.33 g, colorless crystals, 49.8%).

IR (KBr): 3309, 2901, 2845, 1615, 1534 cm$^{-1}$
mp: 96.8-104.9° C.

Present Compound Preparation Example 21

3-(4-Pyridylmethylideneamino)propionic acid N-[2-(1-adamantyl)-ethyl]-N-pentylamide (Compound No. 21-1)

3-(t-Butoxycarbonylamino)propionic acid (1.0 g, 5.3 mmol) was dissolved in anhydrous tetrahydrofuran (15 ml), N-methylmorpholine (0.6 ml, 5.5 mmol) was added to the solution, the mixture was stirred at −15° C., and isobutyl chlorocarbonate (0.7 ml, 5.4 mmol) was added to the mixture. Then a solution of a free base of 2-(1-adamantyl)-N-pentylethylamine hydrochloride (Intermediate No. 1-1, 1.5 g, 5.3 mmol) in anhydrous tetrahydrofuran (15 ml) was added thereto at −18° C. The whole was stirred at 0° C. for 1.5 hours, then ethyl acetate (100 ml) and a saturated aqueous sodium hydrogencarbonate solution (100 ml) were added to the reaction mixture to distribute it. The organic layer was washed with a 10% aqueous citric acid solution (100 ml), water (100 ml) and a saturated aqueous sodium chloride solution (100 ml) successively, dried over anhydrous magnesium sulfate and concentrated under reduced pressure. Then the obtained concentrate was purified by silica gel column chromatography to give 3-(t-butoxycarbonylamino)propionic acid N-[2-(1-adamantyl)ethyl]-N-pentylamide (1.9 g, 85%) as an oily matter.

A 4.0 N hydrogen chloride/1,4-dioxane solution (22 ml, 88 mmol) was added to 3-(t-butoxycarbonylamino)propionic acid N-[2-(1-adamantyl)ethyl]-N-pentylamide (1.9 g, 4.4 mmol) under ice-cooling, and then the mixture was stirred at room temperature for one hour and 15 minutes. The reaction mixture was concentrated under reduced pressure to give the intended hydrochloride (1.4 g, 89%). A 1 N aqueous sodium hydroxide solution (80 ml) was added to the hydrochloride, and the whole was extracted with chloroform (80 ml). The chloroform layer was washed with a saturated aqueous sodium chloride solution (80 ml), dried over anhydrous magnesium sulfate and concentrated under reduced pressure to give 3-aminopropionic acid N-[2-(1-adamantyl)ethyl]-N-pentylamide as an oily matter.

3-Aminopropionic acid N-[2-(1-adamantyl)ethyl]-N-pentylamide (1.3 g, 3.9 mmol) was dissolved in anhydrous tetrahydrofuran (10 ml), and the solution was stirred under ice-cooling. 4-Pyridinecarboxyaldehyde (0.42 ml, 4.3 mmol) was added to the solution, and then the mixture was stirred at room temperature for three hours. The reaction mixture was concentrated under reduced pressure to give the target compound (1.7 g, quantitatively) as an oily matter.

IR (neat): 2901, 1713, 1644, 1454 cm$^{-1}$

Present Compound Preparation Example 22

3-(4-Pyridylmethylamino)propionic acid N-[2-(1-adamantyl)ethyl]-N-pentylamide (Compound No. 22-1)

3-(4-Pyridylmethylideneamino)propionic acid N-[2-(1-adamantyl)ethyl]-N-pentylamide (Compound No. 21-1, 1.6 g, 3.9 mmol) was dissolved in methanol, 10% palladium on carbon (catalytic amount) was added to the solution, and the mixture was stirred at room temperature under hydrogen at 1 atm for seven hours. The 10% palladium on carbon was filtered out, the filtrate was concentrated under reduced pressure, and the concentrate was purified by silica gel column chromatography to give the target compound (0.58 g, 36%) as an oily matter.

IR (neat): 3313, 2902, 2846, 1636, 1451 cm$^{-1}$

Present Compound Preparation Example 23

1-[2-(1-Adamantyl)ethyl]-3-[3-[4-(2-cyano)pyridyl] propyl]-1-pentylurea (Compound No. 23-1)

Trimethylsilyl cyanide (1.2 ml, 9.4 mmol) and triethylamine (0.65 ml, 4.7 mmol) were added to a solution of 4-[3-[3-[2-(1-adamantyl)ethyl]-3-pentylureido]propyl]pyridine N-oxide (Compound No. 16-1, 1.0 g, 2.3 mmol) in anhydrous acetonitrile (1.5 ml) at room temperature under a nitrogen atmosphere, and the mixture was refluxed overnight. The reaction mixture was distributed between chloroform (40 ml) and a saturated aqueous sodium hydrogencarbonate solution (40 ml). The organic layer was washed with a saturated aqueous sodium chloride solution (10 ml) and dried over anhydrous magnesium sulfate. The solvent was evaporated under reduced pressure, and the obtained residue was filtered off with diisopropyl ether to give the target compound (730 mg, 73.0%) as crystals.

IR (KBr): 3334, 2900, 2845, 2234, 1621, 1534 cm$^{-1}$
mp: 112.0-123.0° C.

Present Compound Preparation Example 24

1-[2-(1-Adamantyl)ethyl]-3-[3-[4-(2-aminomethyl)pyridyl]propyl]-1-pentylurea (Compound No. 24-1)

Under a nitrogen atmosphere, 10% palladium on carbon (catalytic amount) was added to a solution of 1-[2-(1-adamantyl)ethyl]-3-[3-[4-(2-cyano)pyridyl]propyl]-1-pentylurea (Compound No. 23-1, 0.20 g, 0.46 mmol) in methanol (2.0 ml) at room temperature, and the mixture was stirred under a hydrogen atmosphere overnight. The reaction mixture was filtered with Celite, the solvent was evaporated under reduced pressure, and the obtained residue was distributed between diethyl ether (50 ml) and water (50 ml). A 2 N aqueous sodium hydroxide solution (10 ml) was added to the aqueous layer, and the whole was further extracted with diethyl ether (50 ml). The combined organic layer was washed with a saturated aqueous sodium chloride solution (10 ml) and dried over anhydrous magnesium sulfate. The solvent was evaporated under reduced pressure, and the obtained residue was filtered off with diisopropyl ether to give the target compound (151 mg, 74.4%) as crystals.

IR (KBr): 3346, 2901, 2845, 1621, 1538 cm$^{-1}$
mp: 88.0-95.0° C.

Present Compound Preparation Example 25

1-[2-(1-Adamantyl)ethyl]-3-[3-[4-(2-carboxy)pyridyl]propyl]-1-pentylurea (Compound No. 25-1)

Six normality hydrochloric acid (1.5 ml, 9.2 mmol) was added to 1-[2-(1-adamantyl)ethyl]-3-[3-[4-(2-cyano)pyridyl]propyl]-1-pentylurea (Compound No. 23-1, 0.20 g, 0.46 mmol) at room temperature, and the mixture was refluxed overnight. The reaction mixture was concentrated under reduced pressure, and the resulting crystals were filtered off with acetone. The crystals were dissolved in chloroform (40 ml), and the solution was washed with water (40 ml) and a saturated aqueous sodium chloride solution (10 ml) successively. The organic layer was dried over anhydrous magnesium sulfate, and the solvent was evaporated under reduced pressure to give the target compound (132 mg, 63.0%).

IR (KBr): 3326, 2905, 2848, 1704, 1621, 1539 cm$^{-1}$
mp: 130° C.

Present Compound Preparation Example 26

1-[2-(1-Adamantyl)ethyl]-3-[3-[4-(2-hydroxymethyl)pyridyl]propyl]-1-pentylurea (Compound No. 26-1)

A 1.0 M solution of a borane-tetrahydrofuran complex in tetrahydrofuran (0.66 ml, 0.66 mmol) was added to a solution of 1-[2-(1-adamantyl)ethyl]-3-[3-[4-(2-carboxy)pyridyl]propyl]-1-pentylurea (Compound No. 25-1, 0.10 g, 0.22 mmol) in anhydrous tetrahydrofuran (0.7 ml) under a nitrogen atmosphere and ice-cooling, and the mixture was stirred at room temperature for 4.5 hours. Water (3 ml) was added to the reaction mixture under ice-cooling, and then the whole was distributed between ethyl acetate (15 ml) and a 0.1% aqueous sodium hydroxide solution (10 ml). The organic layer was washed with a saturated aqueous sodium chloride solution (10 ml) and dried over anhydrous magnesium sulfate. The solvent was evaporated under reduced pressure, and the obtained residue was purified by silica gel column chromatography to give a borane complex salt (53 mg) of the target compound as an oily matter.

IR (neat): 3342, 2904, 1630, 1531 cm$^{-1}$

Present Compound Preparation Example 27

1-[2-(1-Adamantyl)ethyl]-3-[3-[4-(2-methyl)pyridyl]propyl]-1-pentylurea (Compound No. 27-1)

p-Toluenesulfonyl chloride (23 mg, 0.12 mmol) was added to a solution of 1-[2-(1-adamantyl)ethyl]-3-[3-[4-(2-hydroxymethyl)-pyridyl]propyl]-1-pentylurea (Compound No. 26-1, 50 mg, 0.11 mmol) and triethylamine (20 µl, 0.13 mmol) in anhydrous dichloromethane (1.0 ml) at room temperature, and the mixture was stirred at room temperature overnight. The reaction mixture was distributed between chloroform (9 ml) and water (10 ml), and the organic layer was dried over anhydrous magnesium sulfate. The solvent was evaporated under reduced pressure, and the obtained residue was purified by silica gel column chromatography. Ten percent palladium on carbon (catalytic amount) was added to a solution of the obtained p-toluenesulfonyl body in methanol (1 ml), and the mixture was stirred under a hydrogen atmosphere for seven days to give the target compound (18 mg, 38%) as an oily matter.

IR (neat): 3345, 2903, 2847, 1624, 1534 cm$^{-1}$

Present Compound Preparation Example 28

1-[2-(1-Adamantyl)ethyl]-1-(2-aminoethyl)-3-[3-(4-pyridyl)propyl]urea (Compound No. 28-1)

Under ice-cooling, 6 N hydrochloric acid (15 ml) was added to a solution of 1-[2-(acetylamino)ethyl]-1-[2-(1-adamantyl)ethyl]-3-[3-(4-pyridyl)propyl]urea (Compound No. 1-103, 1.02 g, 2.39 mmol) in methanol (10 ml), and the mixture was heated at 90° C. with stirring for three days. The reaction mixture was neutralized with a 1 N aqueous sodium hydroxide solution (10 ml), and the whole was distributed between chloroform (50 ml) and water (10 ml). The organic layer was washed with a saturated aqueous sodium chloride solution (50 ml) and dried over anhydrous magnesium sulfate, and the solvent was evaporated under reduced pressure. The residue was purified by silica gel column chromatography to give the target compound (200 mg, 21.7%) as an oily matter.

IR (neat): 3306, 2902, 2846, 1629, 1605, 1537, 753 cm$^{-1}$

Present Compound Preparation Example 29

4-[2-[N-[2-(1-Adamantyl)ethyl]-N-pentylcarbonylmethoxy]ethoxy]pyridine N-oxide (Compound No. 29-1)

2-(1-Adamantyl)-N-pentylethylamine hydrochloride (Intermediate No. 1-1, 0.50 g, 1.7 mmol) was added to a solution of diglycolyl chloride (0.31 ml, 2.6 mmol) and triethylamine (0.70 ml, 5.1 mmol) in anhydrous dichloromethane (6 ml) under ice-cooling, and the mixture was stirred at room temperature overnight. Methanol (5 ml) was added to the reaction mixture, and the whole was stirred for three hours. The solvent was evaporated under reduced pressure, the residue was distributed between ethyl acetate (15 ml) and water (15 ml), and the organic layer was washed with a saturated aqueous sodium chloride solution (5 ml) and dried over anhydrous magnesium sulfate. The solvent was evaporated under reduced pressure, and the obtained residue was purified by silica gel column chromatography to give 2-methoxycarbonylmethoxyacetic acid N-[2-(1-adamantyl)ethyl]-1-pentylamide (0.39 g, 60%) as an oily matter.

Next, sodium borohydride (0.18 g, 4.8 mmol) was added to a solution of N-[2-(1-adamantyl)ethyl]-1-pentylamide (0.37 g, 0.96 mmol) in methanol (3 ml) under ice-cooling, and the mixture was stirred at room temperature overnight. Water (10 ml) was added to the reaction mixture, and the whole was stirred for 10 minutes and then distributed between water (20 ml) and ethyl acetate (30 ml). The organic layer was washed with a saturated aqueous sodium chloride solution (10 ml) and dried over anhydrous magnesium sulfate. The solvent was evaporated under reduced pressure, and the obtained residue was purified by silica gel column chromatography to give 2-(2-hydroxyethoxy)acetic acid N-[2-(1-adamantyl) ethyl]-1-pentylamide (74 mg, 22%) as an oily matter.

Next, 4-nitropyridine N-oxide (24 mg, 0.17 mmol) and potassium carbonate (28 mg, 0.20 mmol) were added to a solution of 2-(2-hydroxyethoxy)acetic acid N-[2-(1-adamantyl)ethyl]-1-pentylamide (60 mg, 0.17 mmol) in N,N-dimethylformamide (0.4 ml) at room temperature, and the mixture was stirred at 60° C. for two days. The reaction mixture was concentrated under reduced pressure, and the obtained residue was purified by silica gel column chromatography to give the target compound (39 mg) as an oily matter.

$^1$H-NMR (400MHz, CDCl$_3$) δ 0.87-0.93 (m, 3H), 1.20-1.40 (m, 6H), 1.47-1.60 (m, 8H), 1.61-1.67 (m, 3H), 1.68-1.76 (m, 3H), 1.97 (brs, 3H), 3.10-3.19 (m, 2H), 3.25-3.36 (m, 2H), 3.94-3.98 (m, 2H), 4.20-4.27 (m, 4H), 6.81-6.86 (m, 2H), 8.10-8.15 (m, 2H)

Present Compound Preparation Example 30

2-[2-(4-Pyridyloxy)ethoxy]acetic acid N-[2-(1-adamantyl)ethyl]-N-pentylamide (Compound No. 30-1)

Under a nitrogen atmosphere, 10% palladium on carbon (catalytic amount) was added to a solution of 4-[2-[N-[2-(1-adamantyl)ethyl]-N-pentylcarbonylmethoxy)ethoxy]pyridine N-oxide (Compound No. 29-1, 39 mg, 0.088 mmol) and acetic anhydride (20 μl, 0.18 mmol) in a mixed solvent of methanol (0.4 ml) and acetic acid (0.1 ml) at room temperature, and the mixture was stirred under a hydrogen atmosphere for four days. The reaction mixture was filtered with Celite, the filtrate was concentrated under reduced pressure, and the concentrate was distributed between ethyl acetate (20 ml) and a saturated aqueous sodium hydrogencarbonate solution (20 ml). The organic layer was washed with a saturated aqueous sodium chloride solution (10 ml) and dried over anhydrous magnesium sulfate. The solvent was evaporated, and the obtained residue was purified by silica gel column chromatography to give the target compound (16 mg, 42%) as an oily matter.

IR (neat): 2903, 1651, 1592 cm$^{-1}$

Present Compound Preparation Example 31

1-[2-(1-Adamantyl)ethyl]-3-[3-oxo-3-(4-pyridyl) propyl]-1-pentylurea (Compound No. 31-1)

1,1,1-Triacetoxy-1,1-dihydro-1,2-benziodoxol-3(1H)-one (221 mg, 0.520 mmol) was added to a solution of 1-[2-(1-adamantyl)ethyl]-3-[3-hydroxy-3-(4-pyridyl)propyl]-1-pentylurea (Compound No. 14-1, 100 mg, 0.234 mmol) in anhydrous dichloromethane (2 ml) under ice-cooling, and the mixture was stirred at room temperature for one hour. The reaction mixture was cooled with ice again, ethyl acetate (10 ml), a saturated aqueous sodium sulfite solution (5 ml) and a saturated aqueous sodium hydrogencarbonate solution (5 ml) were added to the reaction mixture, and the whole was stirred for 15 minutes. The whole was distributed between ethyl acetate (50 ml) and water (10 ml). The organic layer was washed with a saturated aqueous sodium sulfite solution (5 ml), a saturated aqueous sodium hydrogencarbonate solution (5 ml) and a saturated aqueous sodium chloride solution (25 ml) successively and dried over anhydrous magnesium sulfate. The solvent was evaporated under reduced pressure to give the target compound (87.3 mg, 87.8%) as colorless crystals.

IR (KBr): 3328, 2901, 2847, 1710, 1619, 1540 cm$^{-1}$
mp: 103.5-104.0° C.

[C] FORMULATION EXAMPLE

One example of ophthalmic solution formulation of the present compound is shown below.

| Formulation 1 (in 100 ml) | |
| --- | --- |
| Present compound | 100 mg |
| Sodium chloride | 900 mg |
| Polysorbate 80 | quantum sufficit |
| Sodium hydroxide | quantum sufficit |
| Hydrochloric acid | quantum sufficit |
| Sterile purified water | quantum sufficit |

Desired ophthalmic solutions can be obtained by appropriately changing the mixing ratio of the present compound to the additives.

[D] PHARMACOLOGICAL TESTS (1) Angiogenesis Inhibition Tests Using Human Endothelial Cells The effects of the present compounds on the in vitro angiogenesis were evaluated by using vascular endothelial growth factor (VEGF)-induced normal human umbilical vein endotherial cells (HUVEC) proliferation system (Cancer Res., 59, 99-106 (1999)), wherein inhibitory effects of drugs on cell growth reactions induced by treating HUVEC with VEGF as an in vitro angiogenesis evaluation model.

Preparation of Test Compound Solutions

The present compound was dissolved in DMSO and then diluted with a medium to prepare 40 μM test compound solution.

Experimental Method $2 \times 10^3$ cells/well of HUVEC was seeded onto a type I collagen coated 96-well plate. After one day, 25 μl of the 40 μM test compound solution and a 0.8% DMSO solution as a control were added to each well (final concentration; 10 μM of the test compound and 0.2% of DMSO). One hour after adding the test compound, 25 μl of 40 ng/ml VEGF solution was added to each well(final concentration; 10 ng/ml of VEGF). Three days after adding VEGF, a WST-8 assay reagent (manufactured by Dojin Chemical Co., Ltd.) was added to each well in an amount of 10 μl, and absorbance at 450 nm was measured.

Evaluation Results of Angiogenesis

Calculating cell growth inhibitory rates (%) to the control, angiogenesis inhibitory rates of almost all of the test compounds were 80% or higher. These results are shown in Table 1.

TABLE 1

| Test substance | Inhibitory rate (%) |
| --- | --- |
| Compound No. 1-1 | 83.4 |
| Compound No. 1-24 | 82.1 |
| Compound No. 1-25 | 83.2 |
| Compound No. 1-26 | 79.2 |
| Compound No. 1-35 | 83.7 |
| Compound No. 1-100 | 83.0 |
| Compound No. 1-107 | 83.2 |
| Compound No. 1-111 | 83.1 |
| Compound No. 1-112 | 83.2 |
| Compound No. 1-118 | 81.6 |
| Compound No. 1-120 | 83.1 |
| Compound No. 1-137 | 83.3 |
| Compound No. 1-139 | 83.1 |
| Compound No. 2-14 | 83.4 |
| Compound No. 2-15 | 83.3 |
| Compound No. 2-18 | 82.2 |
| Compound No. 2-20 | 82.5 |

(2) Angiogenesis Inhibition Tests by Using Oxygen-Induced Retinal Angiogenesis Model The effects of the present compounds on the in vivo angiogenesis were evaluated by using oxygen-induced retinal angiogenesis model (Arch Ophthalmol., 114, 1210-1217 (1996)), wherein angiogenesis inhibitory effects of drugs induced by exposing new-born baby rats to high concentration oxygen were measured.

Preparation of Test Compound Suspensions

The present compound was suspended in a phosphate buffer (PBS) containing 0.4% Tween 80 to prepare a 10 mg/ml test compound suspension.

Experimental Method

The new-born baby rats (no more than a few hours after birth) were put with their mothers into the oxygen container maintained at an 80% oxygen condition for 11 days, and the condition was returned to an ordinary breeding condition on 11th day postbirth. (The condition was returned to the ordinary breeding condition for 30 minutes once a day during a high oxygen exposure period.).

The test compound (200 μg/20 μl/eye) was administered subconjunctivally under avertin anesthesia for seven days from 11th day postbirth. The rats were sucrificed by Nembutal overdose on 18th day postbirth (P18), and eyeballs were enucleated. The enucleated eyeball was fixed with 4% paraformaldehyde, and then a retina was separated. The separated retina was stained with ADPase, and degrees of angiogenesis were evaluated by the following angiogenesis evaluation method. PBS (2 μl/eye) containing 0.4% Tween 80 was administered subconjunctivally instead of the test compound as a control of the model rats, and the same operation as mentioned above was carried out.

The retina stained with ADPase was divided into quadrants and observed with a light microscope to evaluate it. The evaluation was carried out by marking each quadrant according to the following evaluation criteria.

Evaluation Criteria

0: No neovascular bud or continuous neovascular ridge was observed.
1: Five or less neovascular buds were observed.
2: Six or more neovascular buds or short neovascular ridges were observed.
3: Neovascular ridges extending less than halfway across a quadrant were observed.
4: Neovascular ridges exceeding halfway across a quadrant were observed.

Evaluation Results of Angiogenesis

Calculating angiogenesis inhibitory rates [%] from total scores obtained by adding scores of each quadrant (the angiogenesis inhibitory rates were the average of nine to 12 samples respectively), the angiogenesis inhibitory rates of many test compounds were 40% or higher.

INDUSTRIAL APPLICABILITY

The above-mentioned results of the pharmacological tests explicitly show that since the present compounds have excellent angiogenesis inhibitory actions in both in vitro and in vivo tests, the present compounds can be applied as preventives and therapeutic agents for diseases in which angiogenesis participates, particularly diabetic retinopathy, retinopathy of prematurity, macular degeneration, neovascular glaucoma, retinal vein occlusion, retinal artery occlusion, pterygium, rubeosis, corneal neovasculature, solid tumors, hemangioma, proliferation and transfer of tumors, and the like.

The invention claimed is:

1. An angiogenesis inhibitor comprising 1-[2-(1-adamantyl)ethyl]-1-pentyl-3-[3-(4-pyridyl)propyl]urea or a salt thereof as an active ingredient.

2. A composition for treating diabetic retinopathy, retinopathy of prematurity, macular degeneration, neovascular glaucoma, retinal vein occlusion, retinal artery occlusion, pterygium, rubeosis or corneal neovasculature comprising a pharmaceutically effective amount of 1-[2-(1-adamantyl)ethyl]-1-pentyl-3-[3-(4-pyridyl)propyl]urea or a salt thereof as an active ingredient in combination with a pharmaceutically acceptable carrier.

* * * * *